(12) United States Patent
Takahashi et al.

(10) Patent No.: US 6,300,514 B1
(45) Date of Patent: *Oct. 9, 2001

(54) ARYL (SULFIDE, SULFOXIDE AND SULFONE) DERIVATIVES AND DRUGS CONTAINING THE SAME AS THE ACTIVE INGREDIENT

(75) Inventors: Kanji Takahashi; Tsuneyuki Sugiura, both of Mishima-gun (JP)

(73) Assignee: Ono Pharmaceutical Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,116
(22) PCT Filed: Jun. 25, 1997
(86) PCT No.: PCT/JP97/02200
§ 371 Date: Jan. 15, 1999
§ 102(e) Date: Jan. 15, 1999
(87) PCT Pub. No.: WO97/49679
PCT Pub. Date: Dec. 31, 1997
(51) Int. Cl.[7] .................. C07C 321/00; C07D 317/44
(52) U.S. Cl. .................. 560/17; 560/11; 560/12; 560/14; 549/447; 562/429; 562/430; 562/431; 564/162; 546/342
(58) Field of Search .................. 549/447; 546/342; 564/162; 560/11, 12, 14, 17; 562/429, 430, 431

(56) References Cited

U.S. PATENT DOCUMENTS

| | | | |
|---|---|---|---|
| 3,321,483 | 5/1967 | Crenshaw | 260/293.4 |
| 3,849,574 | 11/1974 | Suh | 424/319 |
| 4,065,584 | 12/1977 | Lafon | 424/316 |
| 4,207,329 | 6/1980 | Williams et al. | 424/274 |
| 4,271,170 | 6/1981 | Ianouchi et al. | 514/263 |
| 4,461,905 | 7/1984 | Iizuka et al. | 548/341 |
| 4,632,934 | 12/1986 | Lizuka et al. | 514/399 |
| 4,666,916 | 5/1987 | Schneider | 514/291 |
| 4,780,469 | 10/1988 | Toda et al. | 514/382 |
| 4,994,479 | 2/1991 | Mase et al. | 514/381 |
| 5,214,191 | 5/1993 | Kirschenheuter et al. | 514/231.8 |
| 5,216,022 | 6/1993 | Oleksyszya et al. | 514/533 |
| 5,240,956 | 8/1993 | Kirschenheuter | 514/419 |
| 5,455,258 | 10/1995 | MacPherson et al. | 514/357 |
| 5,468,722 | 11/1995 | Shibata et al. | 504/282 |
| 5,554,553 | 9/1996 | Hui et al. | 514/605 |
| 5,569,665 | 12/1996 | Porter et al. | 514/357 |
| 5,648,368 | 7/1997 | Egbertson et al. | 514/331 |
| 5,665,777 | 9/1997 | Fesik et al. | 514/575 |
| 5,821,262 | 10/1998 | Crimmin et al. | 514/445 |
| 5,854,277 | 12/1998 | Kluender et al. | 514/448 |
| 5,932,595 | 8/1999 | Bender et al. | 514/317 |
| 6,022,898 | 2/2000 | Miller et al. | 514/576 |
| 6,037,472 | 3/2000 | Castelhano et al. | 546/269.7 |
| 6,057,369 | 5/2000 | Groneberg et al. | 514/575 |

OTHER PUBLICATIONS

International Search Report dated Sep. 30, 1997 (PCT/JP97/02200).

"Synthesis of Potential Amoebacides. Part XXIV", A. B. Sen and S. B. Singh; J. Indian Chem. Soc. (1966) vol. 43, No. 2. 521–525.

"10C –Carbohydrates, Amino Acids, Proteins", Chemical Abstracts; (1959) pp. 14957–14960.

Chemical Abstracts; (1965) pp. 1547–1548.

National Library of Medicine; Pub/Med; "The C–S lysis of L–cysteinw conjugates by asparate by asparate and alanine aminotrasfer enzymes"; Hum Exp. Toxicol 1995 May; 14(5):422–7.

Enviroment Chemistry; vol. 14, No. 2; Mar. 1995, pp. 134–139.

(List continued on next page.)

Primary Examiner—Amelia Owens
(74) Attorney, Agent, or Firm—Stevens Davis Miller & Moshner, L.L.P.

(57) ABSTRACT

Pharmaceutical composition containing aryl (sulfide, sulfoxide, sulfone) derivatives of the formula (1) and the salts thereof as active ingredient (wherein $R^1$ is H, alkyl; $R^2$ is $COOR^7$, $CONHOR^8$; E is —$CONR^9$—, —$NR^9CO$—, —OCO—, —COO—, —$CH_2$—O—, —$(CH_2)_2$—, vinylene, ethynylene; J is bond, alkylene; A is H, alkyl, Ar, alkyl-OH; $R^3$, $R^4$ is H, alkyl, $COOR^{19}$, hydroxy, —$NR_{20}R^{21}$,

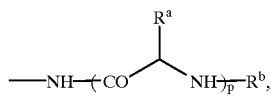

$Ar_1$ etc.); $R^5$, $R^6$ is H, methyl) and the novel aryl (sulfide, sulfoxide, sulfone) derivatives of the formula (I).

(I)

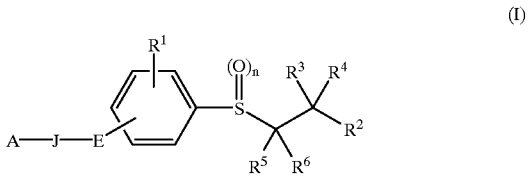

The compounds of the formula (I) have inhibitory activity against matrix metalloproteinases, therefore, the compounds of the formula (I) are useful for prevention and/or treatment of rheumatoid diseases, arthrosteitis, unusual bone resorption, osteoporosis, periodontitis, interstitial nephritis, arteriosclerosis, pulmonary emphysema, cirrhosis, cornea injury, autoimmune diseases, diseases caused by vascular emigration or infiltration of leukocytes, arterialization etc.

10 Claims, No Drawings

OTHER PUBLICATIONS

"Formation of Phenol and Thiocatechol Metabolites from Bromobenzene Premercapturic Acids Through Pyridoxal Phosphate–Dependen C–S Lyase Activity", Khingkan Letratangkoon and Douglas Denney; Biochemical Pharmacology, vol. 45, No. 12, pp. 2513–2525, 1993.

"Role of Glutathione in Prevension of Acetaminophen–Induced Hepatotoxicity by N–Acetyl–Cysteine in Vivo: Studies with N–Acetyl–D–Cysteine in Mice"; The Journal of Pharmacology and Experimental Therapeutics; 1986; vol. 238, No. 1.

Fenbufen, a New Anti–Inflammatory Analgesci: Synthesis and Structure–Activity Relationships of Analogs; Journal of Pharmaceutical Sciences, vol. 66, No. 4 Apr. 1977; pp. 466–476.

Rapid Communication A Novel Pathway for Formation of Thiol Metabolites and Cysteine Conjugates from Cysteine Sulphoxides; Biochemical Pharmology, vol. 46, No. 7; pp. 1113–1117, 1993.

Nonsteroidal Antiandrogens. Synthesis and Structure – Activity a Relationships 3–Substituted Derivatives of 2–Hydroxypropionanilides; J. Med. Chem. 1988, 31, 954–959.

Biocatalyic Resolution of Sulfinylalknoates: A facile Route to Optically Active Sulfoxides: J. Org. Chem 1992, 57, 1290–1295.

The Synthesis of 4–S–Cysteinyl–[U–14 C]phenol, an Experimental Antimelanoma Agent; Techincal Note; Appl. Radiat. Isot. vol. 40, No. 5, pp. 539–540, 1989.

Chemcial Abstracts; (1964) 15955–15956. vol. 61.

The Oxidation of Aminocyclopropyl Sulfides; J. Org. Chem. vol. 40, No. 16, 1975.

Chemical Abstracts ; 1968, 86143h, Steriochemistry of Vinyl carbanions.

ARYL (SULFIDE, SULFOXIDE AND SULFONE) DERIVATIVES AND DRUGS CONTAINING THE SAME AS THE ACTIVE INGREDIENT

This application is a 371 of PCT/JP97/02200 filed Jun. 25, 1997.

FIELD OF THE INVENTION

This invention relates to aryl (sulfide, sulfoxide, sulfone) derivatives, processes for the preparation thereof, and matrix metalloproteinases inhibitors containing them as active ingredient.

More particularly, this invention relates to matrix metalloproteinases inhibitors containing aryl (sulfide, sulfoxide, sulfone) derivatives of the formula (I)

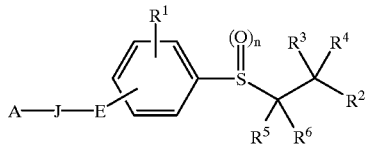

(I)

(wherein all the symbols are the same meanings as hereinafter described.), non-toxic salts thereof, as active ingredient, and the above-mentioned novel aryl (sulfide, sulfoxide, sulfone) derivatives of the formula (I), non-toxic salts thereof, and processes for the preparation thereof.

BACKGROUND OF THE INVENTION

The matrix metalloproteinases (hereinafter abbreviated as MMP) are neutral metalloproteinases and zinc (hereinafter abbreviated as $Zn^{2+}$) is essential in the active site for their activation They degrade collagen, laminin, proteoglycans, fibronectin, elastin, gelatin etc. under physiological conditions and, therefore, are effective on growth and tissue remodeling of articulation tissue, bone tissue and connective tissue. At least 10 classes of MMP which differ in primary structure are identified.

As common characteristics of these enzymes, MMP
(1) have $Zn^{2+}$ in the active site and the activity depends on calcium ($Ca^{2+}$),
(2) are secreted as an inactive proenzyme and activated outside of cells,
(3) have high homology on amino acid sequence,
(4) have an ability to degrade various extracellular matrix components in vivo,
(5) are regulated by tissue inhibitors of metalloproteinases (TIMP) which are specific to MMP.

MMP inhibitors are useful for prevention and/or treatment of various diseases induced by overexpression or excess activation of MMP. Such diseases are, for example, rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune diseases (e.g. Crohn's disease, Sjogren's syndrome), diseases caused by vascular emigration or infiltration of leukocytes, arterialization etc.

Some compounds possessing inhibitory activity against matrix metalloproteinases are known. A sequence in the vicinity of the cleavage site of collagen (Gly-Ile-Ala-Gly or Gly-Leu-Ala-Gly) has high affinity for collagenase. Much research and development on substrate analogous matrix metalloproteinases inhibitors, which are chemically modified so as to have zinc affinity groups on a cleavage site of the substrate, has energetically been carried out [Inhibitors of matrix metalloproteinases (MMP's), Nigel RA Beeley, Phillip R J Ansell, Andrew J P Docherty et al., Curr. Opin. Ther. Patents, 4, 7–16 (1994), Current Drugs Ltd ISSN 0962-2594]. However, these substrate-analogous inhibitors might have various problems. Therefore, it is desired to obtain a non-peptide inhibitor and some compounds are reported.

For example, (1) in the specification of EP 606046, arylsulfonamide derivatives of the formula (X)

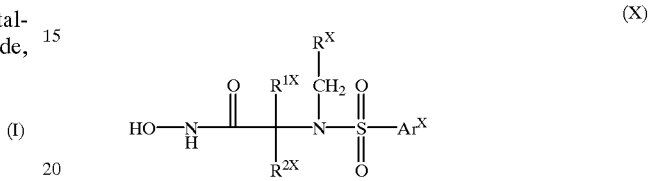

(X)

(wherein (a) $Ar^X$ is carbocyclic or heterocyclic aryl; $R^X$ is hydrogen, lower alkyl, carbocyclic aryl-lower alkyl etc.; $R^{1X}$ is hydrogen, lower alkyl, carbocyclic aryl-lower alkyl etc.; $R^{2X}$ is hydrogen, lower alkyl; or (b) $R^X$ and $R^{1X}$ taken together with the chain to which they are attached form 1,2,3,4-tetrahydro-isoquinoline, piperidine etc.; $Ar^X$ and $R^{2X}$ are as defined in (a); or (c) $R^{1X}$ and $R^{2X}$ taken together with the carbon to which they are attached form C3-7 cycloalkane, oxa-cyclohexane, thia-cyclohexane etc. which is unsubstituted or substituted by lower alkyl; and $Ar^X$ and $R^{2X}$ are as defined in (a).) are disclosed to have inhibitory activity against matrix metalloproteinase.

(2) In the specification of WO 9535276, the compounds of the formula (Y)

(Y)

(wherein $X^Y$ is COOH, CONHOH; $R^{1Y}$ is α-amino acid; $R^{2Y}$ is $Z^{1Y}Q^YW^Y$; $Z^{1Y}$ is hydrogen, aryl etc.; (i) $Q^YW^Y$ together form bond, (ii) $Q^Y$ is O, S, $W^Y$ is C1-20 alkyl etc., (iii) $Q^Y$ is bond, $W^Y$ is C9-20 alkyl etc., (iv) $Q^Y$ is bond, $W^Y$ is C1-8 alkyl; $Y^Y$ is $SO_2$; $Z^Y$ is aryl, heteroaryl.)
are disclosed to have inhibitory activity against matrix metalloproteinase.

(3) In the specification of WO 9615096, the compounds of the formula (Z)

(Z)

(wherein $(T^Z)x^ZA^Z$ is unsubstituted or substituted various aromatic ring or aromatic hetero ring; $B^Z$ is various aromatic ring or aromatic hetero ring; $D^Z$ is —CO—, —CH(OH)—, —$CH_2$— etc.; $E^Z$ is Cn carbon chain optionally having $R^{6Z}$ (in which $R^{6Z}$ is —$(CH_2)v^ZZ^ZR^{8Z}$ (in which $v^Z$ is 0, integer of 1≠4; $Z^Z$ is —S—, —SO—, —$SO_2$— etc.; $R^{8Z}$ is optionally substituted C6-10 aryl etc.)); $G^Z$ is carboxyl, alkoxycarbonyl.)
are disclosed to have inhibitory activity against matrix metalloproteinase.

(4) In the specification of WO 9509841, the compounds of the formula (E)

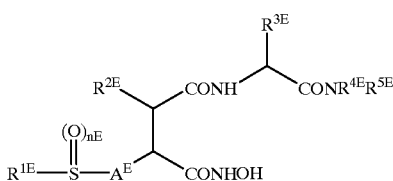

(wherein $R^{1E}$ is phenyl optionally having substituent etc.; $R^{2E}$ is hydrogen, C1-6 alkyl etc.; $R^{3E}$ is amino acid residue optionally having substituent; $R^{4E}$ is hydrogen, C1-6 alkyl etc.; $R^{5E}$ is hydrogen, methyl; $n^E$ is 0, 1, 2; $A^E$ is C1-6 hydrocarbon chain.)
are disclosed to have inhibitory activity against the liberation of TNF, and inhibitory activity against matrix metalloproteinase.

(5) In the specification of WO 9324449, the compounds of the formula (F)

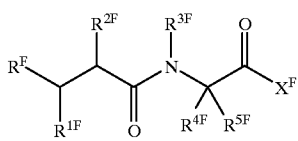

(wherein RF is —CONHOH, carboxyl, esterified carboxyl etc.; $R^{1F}$ is hydrogen, optionally substituted alkyl, alkenyl, aryl, aralky, heteroaralkyl, heteroarylthioalkyl; $R^{2F}$ is optionally substituted arylthio, arylthioalkyl etc.; $R^{3F}$ is hydrogen, alkyl; $R^{4F}$ is hydrogen, alkyl; $R^{5F}$ is optionally substituted alkyl etc.) are disclosed to have inhibitory activity against matrix metalloproteinase.

(6) In the specification of WO 9616027, the compounds of the formula (G)

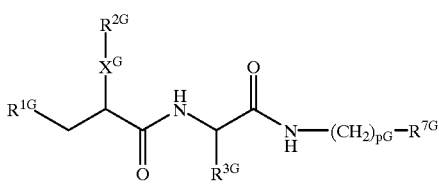

(wherein $R^{1G}$ is —CONHOH, carboxyl, alkoxycarbonyl, aryloxycarbonyl, benzyloxycarbonyl etc.; $R^{2G}$ is aryl etc.; $R^{3G}$ is alkyl etc.; $R^{7G}$ is aryl etc.; $X^G$ is —(CH$_2$)m$^G$Y$^G$(CH$_2$)n$^G$ (in which Y$^G$ is S etc.; m$^G$, n$^G$, p$^G$ is 0~4.)
are disclosed to have inhibitory activity against matrix metalloproteinase.

Also, (7) in the specification of Japanese Patent Kokai No. 4-226939 and (8) Japanese Patent Kokai No. 4-293576, each of the compound of the formula (W-1)

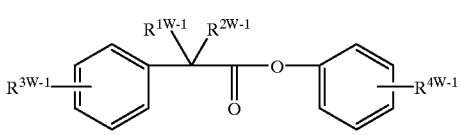

(wherein $R^{1W-1}$, $R^{2W-1}$ is hydrogen, C1-6 alkyl, C3-6 cycloalkyl, or together form methylene, ethylene, polymethylene; $R^{3W-1}$ is hydrogen, halogen, haloalkyl, C1-12 alkyl, C1-12 alkoxy etc.; $R^{4W-1}$ is hydrogen, halogen, nitro, —C(O)CH$_3$, S(O)$_p$R$^{9W-1}$ (in which p is 0, 1, 2, $R^{9W-1}$ is hydroxy, —ONa, optionally substituted C1-12 alkyl, cycloalkyl)), and the compounds of the formula (W-2)

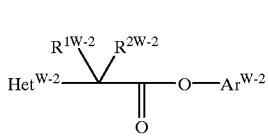

(wherein $R^{1W-2}$, $R^{2W-2}$ is hydrogen, C1-4 alkyl, C3-6 cycloalkyl, or together form methylene, ethylene, polymethylene; Ar$^{W-2}$ is optionally substituted phenyl; HET$^{W-2}$ is hetero ring containing nitrogen, sulfur or oxygen atom over 1 atom.) are disclosed to have inhibitory activity against elastase.

(9) In the specification of EP 0173516, the compounds of the formula (J)

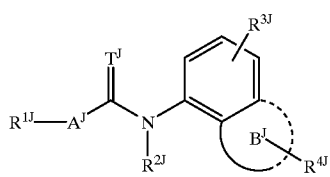

(wherein $B^J$ is —SCH$_2$— etc.; $T^J$ is oxygen etc.; $R^{1J}$ is optionally substituted phenyl, naphthyl by $R^{5J}$, $R^{6J}$, or C1-20 alkyl, alkenyl, alkynyl; $R^{2J}$ is hydrogen, C1-6 alkyl; $R^{3J}$ is hydrogen, alkyl etc.; $R^{4J}$ is —(CH$_2$)p$^J$—COOR$^{8J}$ (in which p$^J$ is 0~10; $R^{8J}$ is hydrogen, C1-6 alkyl.)

are disclosed to have SRS antagonistic activity or 5a-reductase inhibitory activity.

(10) In the specification of British Patent 2031408, the compounds of the formula (K)

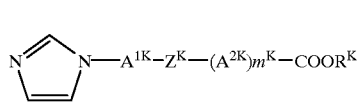

(wherein $R^K$ is hydrogen, alkyl; $A^{1K}$, $A^{2K}$ is alkylene, alkenylene; $m^K$ is 0, 1; $Z^K$ is

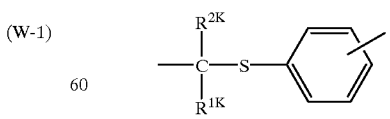

etc.; $R^{1K}$, $R^{2K}$ is hydrogen, alkyl.)

are disclosed to have inhibitory activity against TXA$_2$ synthetase.

(11) In the specification of British Patent 2039903, the compounds of the formula (L)

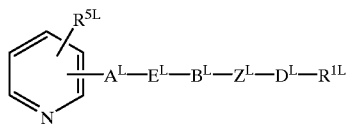

(wherein $A^L$ is C1-5 alkylene optionally substituted by hydroxy; $E^L$ is

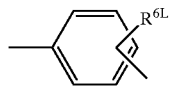

etc.; $B^L$ is sulfur etc.; $Z^L$ is bond, C≡C,

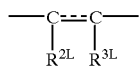

$D^L$ is bond, C1-5 alkylene; $R^{1L}$ is $COOR^{4L}$ etc.; $R^{4L}$ is hydrogen, C1-12 alkyl etc.)
are disclosed to have inhibitory activity against $TXA_2$ synthetase.

(12) In the specification of U.S. Pat. No. 4,461,905, the compounds of the formula (M)

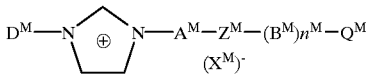

(wherein $A^M$, $B^M$ is C1-8 alkylene, alkenylene; $D^M$ is C2-10 acyl, C2-7 alkoxycarbonyl etc.; $Q^M$ is C2-7 alkoxycarbonyl etc.; $X^M$ is halogen; $n^M$ is 0, 1; $Z^M$ is

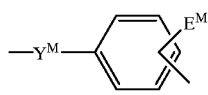

;EM is hydrogen, C1-6 alkyl etc.; $Y^M$ is sulfur etc.)
are disclosed to have inhibitory activity against $TXA_2$ synthetase.

(13) In the specification of WO 865779, the compounds of the formula (N)

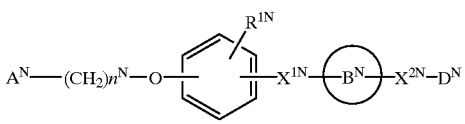

(wherein $X^{1N}$ is —$CH_2CH_2$—, —CH=CH—, —$CH_2$—$Y^{1N}$—, —$Y^{1N}$—$CH_2$—, —$COY^{2N}$—, —$Y^{2N}$—CO— (in which $Y^{1N}$ is oxygen etc.; $Y^{2N}$ is —NH—, —$CH_2Y^{1N}$, —$Y^{1N}CH_2$—);

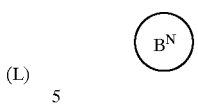

is phenylene etc.; $X^{2N}$ is $Y^{3N}$—$Y^{4N}$— (in which $Y^{3N}$ is sulfur etc.; $Y^{4N}$ is C1-6 alkylene); $D^N$ is —COOH, lower alkoxycarbonyl etc.; $R^{1N}$ is hydrogen, lower alkyl; $n^N$ is 3~10; $A^N$ is hydrogen, phenyl, phenoxy.)
are disclosed to have SRS antagonistic activity.

(14) in the specification of EP 181568, the compounds of the formula (P)

(wherein $Ar^P$ is phenyl etc.; $Z^P$ is C1-10 alkylene optionally containing 0~2 double bonds, and it may be attached to $Ar^P$ through sulfur etc.; $R^P$ is carboxy, alkoxycarbonyl etc.; $n^P$ is 0, 1; $X^P$ is —CH=CH—, ethynylene, —COO—, —$CONR^{1P}$— etc.; $Ar_1^P$ is phenyl, hetero ring containing N, S, O atom.) are disclosed to have 5-lipoxygenase inhibitory activity.

Also, the following compounds are already known. However, it is not disclosed that each compounds have inhibitory activity against matrix metalloproteinases, and it is not disclosed to suggest that these compounds have the activity thereof (the figure in the parentheses represents Chemical Abstract number.).

(1) 3-(4-methylphenylsulfonyl)propionic acid isopropyl ester (122-323393),
(2) 3-(4-methylphenylsulfonyl)propionic acid phenyl ester (095-006058),
(3) 3-(4-methylphenylsulfonyl)propionic acid sodium salt (094-174529),
(4) 3-(4-methylphenylsulfonyl)propionic acid methyl ester (122-323393),
(5) 3-(4-methylphenylsulfonyl)propionic acid ethyl ester (122-323393),
(6) 3-(4-methylphenylsulfonyl)propionic acid (121-009456),
(7) 3-(4-ethylphenylsulfonyl)propionic acid (100-200853),
(8) 3-(4-methoxyphenylsulfonyl)propionic acid phenyl ester (095-006058),
(9) 3-(4-methoxyphenylsulfonyl)propionic acid,
(10) 3-(4-nitrophenylsulfonyl)propionic acid methyl ester (122-323393),
(11) 3-(4-nitrophenylsulfonyl)propionic acid isopropyl ester (122-323393),
(12) 3-(4-nitrophenylsulfonyl)propionic acid,
(13) 3-(4-aminophenylsulfonyl)propionic acid ethyl ester (115-072840),
(14) 3-(4-aminophenylsulfonyl)propionic acid (085-048254),
(15) 3-(4-hydroxyphenylsulfonyl)propionic acid,
(16) 3-(4-hydroxyphenylsulfonyl)propionic acid phenyl ester (111-164337),
(17) 3-(4-bromophenylsulfonyl)propionic acid methyl ester (066-104778),
(18) 3-(4-bromophenylsulfonyl)propionic acid ethyl ester (066-104778),
(19) 3-(4-bromophenylsulfonyl)propionic acid phenyl ester (095-006058),
(20) 3-(4-chlorophenylsulfonyl)propionic acid methyl ester (066-104778),
(21) 3-(4-chlorophenylsulfonyl)propionic acid ethyl ester (066-104778),
(22) 3-(4-chlorophenylsulfonyl)propionic acid t-butyl ester (122-323393),

(23) 3-(4-chlorophenylsulfonyl)propionic acid isopropyl ester (1 22-323393),
(24) 3-(4-chlorophenylsulfonyl)propionic acid (101-006755),
(25) 3-(4-chlorophenylsulfonyl)propionic acid phenyl ester (095-006058),
(26) 3-(4-iodophenylsulfonyl)propionic acid ethyl ester (066-104778),
(27) 3-(4-iodophenylsulfonyl)propionic acid methyl ester (066-104778),
(28) 3-(4-acetylaminophenylsulfonyl)propionic acid methyl ester (114-014686),
(29) 3-(4-acetylaminophenylsulfonyl)propionic acid ethyl ester (115-072840),
(30) 3-(4-vinylphenylsulfonyl)propionic acid sodium salt (094-174529),
(31) 3-(4-carboxyphenylsulfonyl)propionic acid,
(32) 3-(4-cyanophenylsulfonyl)propionic acid ethyl ester,
(33) 3-(4-formylphenylsulfonyl)propionic acid ethyl ester,
(34) 3-(4-biphenylsulfonyl)propionic acid methyl ester (093-061046),
(35) 2-amino-3-(2-methylphenylsulfonyl)propionic acid (53-14959g),
(36) 2-amino-3-(3-methylphenylsulfonyl)propionic acid (53-149599),
(37) 2-amino-3-(4-methylphenylsulfonyl)propionic acid (53-14959g),
(38) 2-amino-3-(4-fluorophenylsulfonyl)propionic acid (53-14959g),
(39) 2-t-butoxycarbonylamino-3-(4-fluorophenylsulfonyl) propionic acid (124-289512),
(40) 2-amino-3-(4-chlorophenylsulfonyl)propionic acid (53-14959g),
(41) 2-t-butoxycarbonylamino-3-(4-chlorophenylsulfonyl) propionic acid (124-117961),
(42) 2-amino-3-(3-trifluoromethylphenylsulfonyl)propionic acid (53-14959h),
(43) 2-amino-3-(4-nitrophenylsulfonyl)propionic acid (119-95106),
(44) 2-amino-3-(2-nitrophenylsulfonyl)propionic acid (119-95106),
(45) 2-amino-3-(4-aminophenylsulfonyl)propionic acid (119-95106),
(46) 2-amino-3-(2-aminophenylsulfonyl)propionic acid (119-95106),
(47) 2,2-dimethyl-3-(4-hydroxyphenylthio)propionic acid ,
(48) 4-(2-carboxy-2-methylpropylmercapto)phenyl 2-phenylbutylate,
(49) 4-(2-carboxy-2-methylpropylsulfinyl)phenyl 2-phenylbutylate,
(50) 4-(2-carboxy-2-methylpropylsulfonyl)phenyl 2-phenylbutylate,
(51) 4-(2-carboxy-2-methylpropylmercapto)phenyl 2-(4-methoxyphenyl)isobutylate,
(52) 4-(2-carboxy-2-methylpropylmercapto)phenyl 2-(3,4-diethylphenyl)isobutyric acid,
(53) 4-(2-carboxy-2-methylpropylmercapto)phenyl 2-(1,2, 3,4-tetrahydro-6-naphthyl)butyrate,
(54) 4-(2-carboxy-2-methylpropylmercapto)phenyl 2-(1-methyl-2-pyrrole)butyrate,
(55) 4-(2-carboxy-2-methylpropylsulfinyl)phenyl 2-(1-methyl-2-pyrrole)butyrate,
(56) 3-(4-bromophenylthio)propionic acid,
(57) N-t-butoxy-3-(4-bromophenylthio)propionamide,
(58) N-t-butoxy-3-(4-biphenylthio)propionamide Compound (47)~(49) and Compound (50)~(55), respectively, are described in the above-mentioned (7) Japanese Patent Kokai 4-226939 and (8) Japanese Patent Kokai 4-283576.

DISCLOSURE OF THE INVENTION

Energetic investigations have been carried out in order to make a matrix metalloproteinase inhibitor. As a result, the present inventors have found that the purpose may be achieved with aryl (sulfide, sulfoxide, sulfone) derivatives of the formula (I).

Most of aryl (sulfide, sulfoxide, sulfone) derivatives of the formula (I) are not known and are novel compounds.

Further, the present inventors have also found that the compounds of the present invention may have a particularly inhibitory activity against matrix metalloproteinases, especially, class of gelatinases.

The present invention relates to
1) matrix metalloproteinases inhibitors containing aryl (sulfide, sulfoxide, sulfone) of the formula (I)

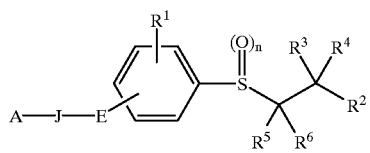

(wherein
$R^1$ is hydrogen, or C1-4 alkyl,
$R^2$ is —COOR$^7$ or —CONHOR$^8$,
$R^7$ is hydrogen, C1-8 alkyl, phenyl, or
C1-4 alkyl substituted by phenyl, —OCOR$^{23}$ (in which R$^{23}$ is C1-4 alkyl.), or —CONR$^{24}$R$^{25}$ (in which R$^{24}$ and R$^{25}$, each independently, is hydrogen or C1-4 alkyl.),
$R^8$ is hydrogen, C1-8 alkyl, phenyl, or C1-4 alkyl substituted by phenyl,
E is —CONR$^9$—, —NR$^9$CO—, —OCO—, —COO—, —CH$_2$—O—, —CO—CH$_2$—, —(CH$_2$)$_2$—, —CH═CH— or —C≡C— (in which R$^9$ is hydrogen, C1-4 alkyl, phenyl, or C1-4 alkyl substituted by phenyl. With proviso that left side of each groups is attached to J group.),
J is bond or C1-8 alkylene,
A is
1) hydrogen,
2) C1-8 alkyl,
3) Ar group (Ar group is carbocyclic ring or heterocyclic ring optionally substituted by 1~3 of
  i) C1-15 alkyl,
  ii) C1-15 alkoxy,
  iii) halogen,
  iv) nitro,
  v) cyano,
  vi) guanidino,
  vii) amidino,
  viii) hydroxy,
  ix) benzyloxy,
  x) NR$^{12}$R$^{13}$ (in which R$^{12}$ and R$^{13}$, each independently, is hydrogen, C1-4 alkyl or —COOR$^{14}$ (in which R$^{14}$ is C1-4 alkyl or benzyloxy.).),
  xi) —COOR$^{15}$ (in which R$^{15}$ is hydrogen, C1-4 alkyl, phenyl, or C1-4 alkyl substituted by phenyl.),
  xii) trifluoromethyl,
  xiii) carbocyclic ring,
  xiv) heterocyclic ring or
  xv) C1-4 alkyl substituted by hydroxy, C1-4 alkoxy, NR$^{12}$R$^{13}$ (in which

9

$R^{12}$ and $R^{13}$ are the same meanings as hereinbefore described.), —COOR$^{15}$ (in which $R^{15}$ is the same meaning as hereinbefore described.), carbocyclic ring or heterocyclic ring.) or 4) C1-4 alkyl substituted by hydroxy or C1-4 alkoxy, or A, J and E taken together, represents methyl, halogen, trifluoromethyl, nitro, cyano, formyl, phenyl, hydroxy, NR$^{16}$R$^{17}$ (in which R$^{16}$ and R$^{17}$, each independently, is hydrogen, C1-4 alkyl, —COOR$^{18}$ (in which R$^{18}$ is C1-4 alkyl or benzyl.).), or heterocyclic ring (this heterocyclic ring may be optionally substituted by 1~4 of C1-4 alkyl, C1-4 alkoxy, halogen, trifluoromethyl, hydroxy, carboxyl, C1-8 alkoxycarbonyl, nitro, NR$^{24}$R$^{25}$ (in which R$^{24}$ and R$^{25}$ are the same meanings as hereinbefore described.) or CONR$^{24}$R$^{25}$ (in which R$^{24}$ and R$^{25}$ are the same meanings as hereinbefore described.).), $R^3$ and $R^4$, each independently, is (1) hydrogen, (2) C1-8 alkyl (with proviso that one of the carbon atom in C1-8 alkyl may be replaced by a sulfur atom.), (3) —COOR$^{19}$ (in which R$^{19}$ is hydrogen, C1-8 alkyl, phenyl, or C1-4 alkyl substituted by phenyl.), (4) Ar$_1$ group (Ar$_1$ group is carbocyclic ring or heterocyclic ring optionally substituted by 1~3 of C1-4 alkyl, C1-4 alkoxy, halogen, hydroxy or trifluoromethyl.), (5) hydroxy, (6) —NR$^{20}$R$^{21}$ (in which R$^{20}$ and R$^{21}$, each independently, is hydrogen, C1-4 alkyl, —COOR$^{22}$ or —COR$^{22}$ (in which R$^{22}$ is C1-4 alkyl or benzyl.), (7)

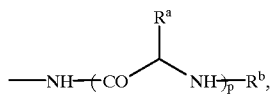

(in which R$^a$ is hydrogen or phenyl, R$^b$ is hydrogen, —COOR$^{22}$ or —COR$^{22}$ (in which R$^{22}$ is the same meaning as hereinbefore described.), p is 1 or 2.), or (8) C1-8 alkyl substituted by substituent selected from the following (a)~(f) (with proviso that one of the carbon atom in C1-8 alkyl may be replaced by a sulfur atom.);

(a) —COOR$^{19}$ (in which R$^{19}$ is the same meaning as hereinbefore described.)

(b) C1-4 alkoxy, (c) hydroxy, (d) benzyloxy, (e) —NR$^{20}$R$^{21}$ (in which R$^{20}$ and R$^{21}$ are the same meanings as hereinbefore described.), or (f) Ar$_1$ group (in which Ar$_1$ is the same meaning as hereinbefore described.)

or $R^3$ and $R^4$ taken together with the carbon to which they are attached, form C3-7 cycloalkyl, $R^5$ and $R^6$ is hydrogen or methyl, or $R^3$ and $R^5$ taken together, form bond, $R^4$ and $R^6$ are the same meanings as hereinbefore described, n is 0, 1 or 2.

With proviso that:

when A, J and E taken together, form phenyl, and $R^2$ is CONHOH, then n is 1 or 2.)

or non-toxic salts thereof, as active ingredient, 2) aryl (sulfide, sulfoxide, sulfone) derivatives of the formula (I)

10

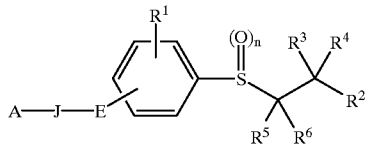

(wherein $R^1$ is hydrogen, or C1-4 alkyl, $R^2$ is —COOR$^7$ or —CONHOR$^8$, $R^7$ is hydrogen, C1-8 alkyl, phenyl, or C1-4 alkyl substituted by phenyl, —OCOR$^{23}$ (in which R$^{23}$ is C1-4 alkyl.), or —CONR$^{24}$R$^{25}$ (in which R$^{24}$ and R$^{25}$ each independently, is hydrogen or C1-4 alkyl.), $R^8$ is hydrogen, C1-8 alkyl, phenyl, or C1-4 alkyl substituted by phenyl, E is —CONR$^9$—, —NR$^9$CO—, —OCO—, —COO, —CH$_2$—O—, CO—CH$_2$—, —(CH$_2$)$_2$—, —CH═CH— or —C≡C— (in which R$^9$ is hydrogen, C1-4 alkyl, phenyl, or C1-4 alkyl substituted by phenyl. With proviso that left side of each groups is attached to J group.), J is bond or C1-8 alkylene, A is 1) hydrogen, 2) C1-8 alkyl, 3) Ar group (Ar group is carbocyclic ring or heterocyclic ring optionally substituted by 1~3 of i) C1-1 5 alkyl, ii) C1-15 alkoxy, iii) halogen, iv) nitro, v) cyano, vi) guanidino, vii) amidino, viii) hydroxy, ix) benzyloxy, x) NR$^{12}$R$^{13}$ (in which R$^{12}$ and R$^{13}$, each independently, is hydrogen, C1-4 alkyl or —COOR$^{14}$ (in which R$^{14}$ is C1-4 alkyl or benzyloxy.).), xi) —COOR$^{15}$ (in which R$^{15}$ is hydrogen, C1-4 alkyl, phenyl, or C1-4 alkyl substituted by phenyl.), xii) trifluoromethyl, xiii) carbocyclic ring, xiv) heterocyclic ring or xv) C1-4 alkyl substituted by hydroxy, C1-4 alkoxy, NR$^{12}$R$^{13}$ (in which R$^{12}$ and R$^{13}$ are the same meanings as hereinbefore described.), —COOR$^{15}$ (in which R$^{15}$ is the same meaning as hereinbefore described.), carbocyclic ring or heterocyclic ring.) or 4) C1-4 alkyl substituted by hydroxy or C1-4 alkoxy, or A, J and E taken together, represents methyl, halogen, trifluoromethyl, nitro, cyano, formyl, phenyl, hydroxy, NR$^{16}$R$^{17}$ (in which R$^{18}$ and R$^{17}$, each independently, is hydrogen, C1-4 alkyl, —COOR$^{18}$ (in which R$^{18}$ is C1-4 alkyl or benzyl.).), or heterocyclic ring (this heterocyclic ring may be optionally substituted by 1~4 of C1-4 alkyl, C1-4 alkoxy, halogen, trifluoromethyl, hydroxy, carboxyl, C1-8 alkoxycarbonyl, nitro, NR$^{24}$R$^{25}$ (in which R$^{24}$ and R$^{25}$ are the same meanings as hereinbefore described.) or CONR$^{24}$R$^{25}$ (in which R$^{24}$ and R$^{25}$ are the same meanings as hereinbefore described.).), $R^3$ and $R^4$, each independently, is (1) hydrogen,
(2) C1-8 alkyl (with proviso that one of the carbon atom in C1-8 alkyl may be replaced by a sulfur atom.),
(3) —COOR$^{19}$ (in which R$^{19}$ is hydrogen, C1-8 alkyl, phenyl, or C1-4 alkyl substituted by phenyl.),
(4) Ar$_1$ group (Ar$_1$ group is carbocyclic ring or heterocyclic ring optionally substituted by 1~3 of C1-4 alkyl, C1-4 alkoxy, halogen, hydroxy or trifluoromethyl.),
(5) hydroxy,
(6) —NR$^{20}$R$^{21}$ (in which R$^{20}$ and R$^{21}$, each independently, is hydrogen, C1-4 alkyl, —COOR$^{22}$ or —COR$^{22}$ (in which R$^{22}$ is C1-4 alkyl or benzyl.),
(7)

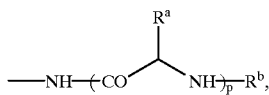

(in which R$^a$ is hydrogen or phenyl, R$^b$ is hydrogen, —COOR$^{22}$ or —COR$^{22}$ (in which R$^{22}$ is the same meaning as hereinbefore described.), p is 1 or 2.), or (8) C1-8 alkyl substituted by substituent selected from the following (a)~(f) (with proviso that one of the carbon atom in C1-8 alkyl may be replaced by a sulfur atom.);
  (a) —COOR$^{19}$ (in which R$^{19}$ is the same meaning as hereinbefore described.)
  (b) C1-4 alkoxy,
  (c) hydroxy,
  (d) benzyloxy,
  (e) —NR$^{20}$R$^{21}$ (in which R$^{20}$ and R$^{21}$ are the same meanings as hereinbefore described.), or
  (f) Ar$_1$ group (in which Ar$_1$ is the same meaning as hereinbefore described.)
or R$^3$ and R$^4$ taken together with the carbon to which they are attached, form C3-7 cycloalkyl,
R$^5$ and R$^6$ is hydrogen or methyl, or R$^3$ and R$^5$ taken together, form bond, R$^4$ and R$^6$ are the same meanings as hereinbefore described,
n is 0, 1 or 2.
With proviso that:
(a) when A, J and E taken together, form phenyl, and R$^2$ is CONHOH, then n is 1 or 2.
(b) when R$^2$ is —COOR$^7$, R$^7$ is hydrogen, C1-8 alkyl, phenyl or C1-4 alkyl substituted by phenyl, then A, J and E taken together, do not represent methyl, halogen, trifluoromethyl, nitro, cyano, hydroxy, NR$^{16}$R$^{17}$ (in which R$^{16}$ and R$^{17}$, each independently, is hydrogen.)
(c) when R$^2$ is —COOR$^7$, R$^7$ is hydrogen, C1-8 alkyl, phenyl or C14 alkyl substituted by phenyl, A is hydrogen or C1-8 alkyl, J is bond or C1-8 alkyl, then E do not represent —CH$_2$—O— or —CH$_2$)$_2$O—.
(d) the following (1)~(16) compounds are excluded.
(1) 3-(4-acetylaminophenylsulfonyl)propionic acid methyl ester,
(2) 3-(4-acetylaminophenylsulfonyl)propionic acid ethyl ester,
(3) 3-(4-vinylphenylsulfonyl)propionic acid sodium salt,
(4) 3-(4-carboxyphenylsulfonyl)propionic acid,
(5) 3-(4-formylphenylsulfonyl)propionic acid ethyl ester,
(6) 3-(4-biphenylsulfonyl)propionic acid methyl ester,
(7) 4-(2-carboxy-2-methylpropylmercapto)phenyl 2-phenylbutylate,
(8) 4-(2-carboxy-2-methylpropylsulfinyl)phenyl 2-phenylbutylate,
(9) 4-(2-carboxy-2-methylpropylsulfonyl)phenyl 2-phenylbutylate,
(10) 4-(2-carboxy-2-methylpropylmercapto)phenyl 2-(4methoxyphenyl)isobutylate,
(11) 4-(2-carboxy-2methylpropylmercapto)phenyl 2-(3,4-diethylphenyl)isobutylate,
(12) 4-(2-carboxy-2-methylpropylmercapto)phenyl 2-(1,2,3,4-tetraydro-6-naphthyl)butyrate,
(13) 4-(2carboxy-2-methylpropylmercapto)phenyl 2-(1-methyl-2-pyrrole)butyrate,
(14) 4-(2-carboxy-2-methylpropylsulfinyl)phenyl 21-methyl-2-pyrrole)butyrate,
(15) N-t-butoxy-3-(4bromophenylthio)propionamide,
(16) N-1-butoxy-3-(4-biphenylthio)propionamide.)
or non-toxic salts thereof, and
processes for the preparation of aryl (sulfide, sulfoxide, sulfone) derivatives and non-toxic salts thereof.

DETAILED DESCRIPTION OF THE INVENTION

Unless otherwise specified, all isomers are included in the present invention. For example, alkyl, alkoxy and alkylene include straight and branched isomers. The double bonds in the alkenylene group include E, Z and EZ mixture. Isomers produced by the existence of asymmetric carbon atoms are included in the present invention when branched-chain alkyl, alkoxy and alkylene etc. exist.

In the formula (I), C1-4 alkyl represented by R$^1$, R$^9$, R$^{10}$, R$^{11}$, R$^{12}$, R$^{13}$, R$^{14}$, R$^{15}$, R$^{16}$, R$^{17}$, R$^{18}$, R$^{20}$, R$^{21}$, R$^{22}$, R$^{23}$, R$^{24}$, R$^{25}$, or C1-4 alkyl as a substituent of Ar$_1$ group and heterocyclic ring represented by A, J and E taken together, means methyl, ethyl, propyl, butyl and the isomers thereof.

In the formula (I), C1-8 alkyl represented by R$^2$, R$^3$, R$^4$, R$^7$, R$^8$, R$^9$, A, means methyl, ethyl, propyl, butyl, pentyl, hexyl, heptyl, octyl and the isomers thereof.

In the formula (I), C1-15 alkyl as a substituent of Ar group, means methyl, ethyl, propyl, butyl, pentyl, hexyl, heptyl, octyl, nonyl, decyl, undecyl, dodecyl, tridecyl, tetradecyl, pentadecyl and the isomers thereof.

In the formula (I), C1-4 alkyl substituted by phenyl represented by R$^7$, R$^8$, R$^9$, R$^{15}$, R$^{19}$, means methyl, ethyl, propyl, butyl and the isomers substituted by one phenyl.

In the formula (I), C1-4 alkoxy in R$^3$ or R$^4$, or C1-4 alkoxy as a substituent of heterocyclic ring represented by A, J and E taken together, means methoxy, ethoxy, propoxy, butoxy and the isomers thereof.

In the formula (I), C1-15 alkyl as a substituent of Ar group, means methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy and the isomers thereof.

In the formula (I), halogen as a substituent of Ar group or Ar$_1$ group, or halogen represented by A, J and E taken together, or halogen as a substituent of heterocyclic ring represented by A, J and E taken together, means fluoro, chloro, bromo and iodo.

In the formula (I), C3-7 cycloalkyl formed by R$^3$ and R$^4$ taken together with the carbon to which they are attached, means cyclopropyl, cyclobutyl, cyclopentyl, cyclohexyl and cycloheptyl.

In the formula (I), carbocyclic ring represented by Ar group, Ar, group, means C5-10 carbocyclic aryl or the above-mentioned C3-7 cycloalkyl. For example, C5-10 carbocyclic aryl includes benzene, pentalene, indene, naphthalene, azulene etc.

In the formula (I), heterocyclic ring represented by Ar group, Ar$_1$ group, R$^3$ or R$^4$, heterocyclic ring represented by A, J and E taken together and heterocyclic ring as a substituent of Ar group, means C5-15 membered mono- or bi-heterocyclic ring containing 1–2 of nitrogen, 1 of oxygen, 1 of sulfur. The heterocyclic ring includes partially or fully saturated analogues of the above C5-15 membered mono- or bi-heterocyclic ring containing 1–2 of nitrogen, 1 of oxygen, 1 of sulfur. For example, C5-15 membered mono- or bi-heterocyclic ring containing 1–2 of nitrogen, 1 of oxygen, 1 of sulfur, includes pyrrole, imidazole, pyrazole, pyridine, pyrazine, pyrimidine, pyridazine, azepine, diazepine, furan, pyran, oxepine, oxazepine, thiophene, thiaine (thiopyran), thiepine, oxazole, isooxazole, thiazole, isothiazole, oxadiazole, oxadiazine, oxazepine, oxadiazepine, thiadiazole, thiadiazine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole etc.

Also, partially or fully saturated C5-15 membered mono- or bi-heterocyclic ring containing 1–2 of nitrogen, 1 of oxygen, 1 of sulfur, includes pyrroline, pyrrolidine, imidazoline, imidazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole etc.

[Salts]

In the present invention, non-toxic salts includes all such salts. For example, non-toxic salts includes general salts, acid addition salts, hydrate salts etc.

The compounds of the present invention of the formula (I) may be converted into the corresponding salts by known method. Non toxic and water-soluble salts are preferable.

Suitable salts include the salts of alkali metal (potassium, sodium etc.), alkaline-earth metal (calcium, magnesium etc.), ammonium salts, salts of organic amine which is pharmacologically permitted (tetramethyl ammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-gulcane etc.).

The compounds of the present invention of the formula (I) may be converted into the corresponding acid-addition salts by known method. Non toxic and water-soluble salts are preferable.

Suitable acid-addition salts include the salts with inorganic acids such as hydrochloric acid, hydrobromide, sulfate, phosphate, nitrate, and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid.

The compounds of the present invention of the formula (I) or salts thereof may be converted into a corresponding hydrate by methods known per se.

In the compounds of the present invention of formula (I), the following compounds are preferred.

the formula (I-1)

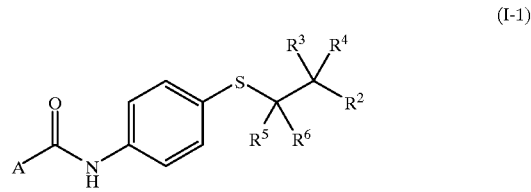

(I-1)

(wherein all symbols are the same meanings as hereinbefore described.), the formula (I-2)

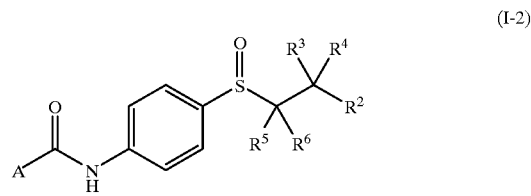

(I-2)

(wherein all symbols are the same meanings as hereinbefore described.), the formula (I-3)

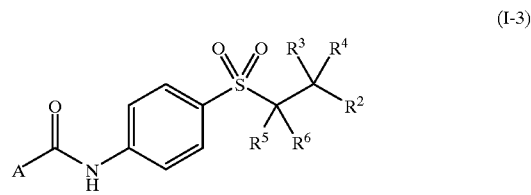

(I-3)

(wherein all symbols are the same meanings as hereinbefore described.), the formula (I-4)

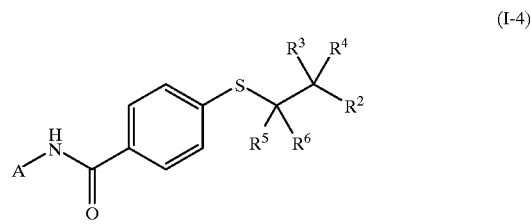

(I-4)

(wherein all symbols are the same meanings as hereinbefore described.), the formula (I-5)

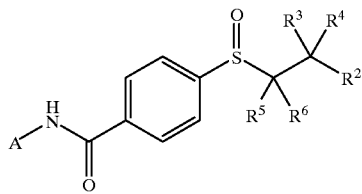
(I-5)

(wherein all symbols are the same meanings as hereinbefore described.), the formula (I-6)

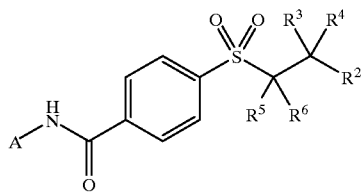
(I-6)

(wherein all symbols are the same meanings as hereinbefore described.), the formula (I-7)

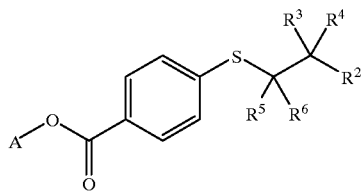
(I-7)

(wherein all symbols are the same meanings as hereinbefore described.), the formula (I-8)

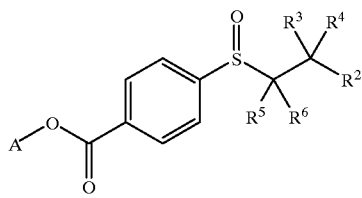
(I-8)

(wherein all symbols are the same meanings as hereinbefore described.), the formula (I-9)

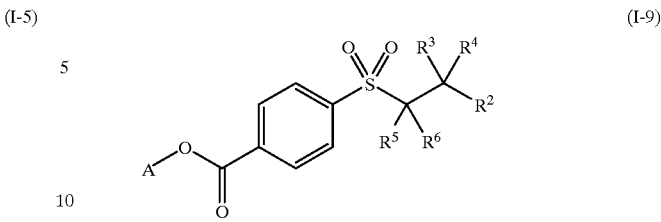
(I-9)

(wherein all symbols are the same meanings as hereinbefore described.), the formula (I-10)

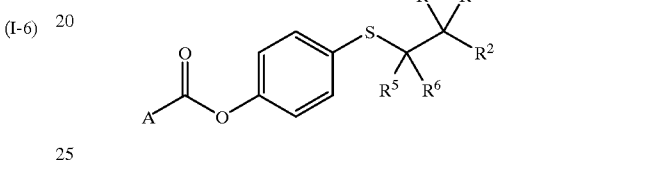
(I-10)

(wherein all symbols are the same meanings as hereinbefore described.), the formula (I-11)

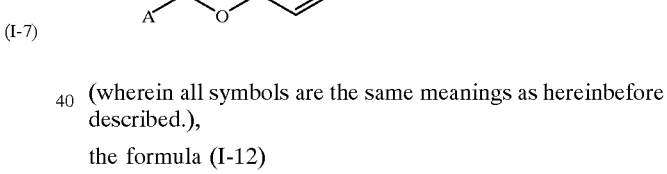
(I-11)

(wherein all symbols are the same meanings as hereinbefore described.), the formula (I-12)

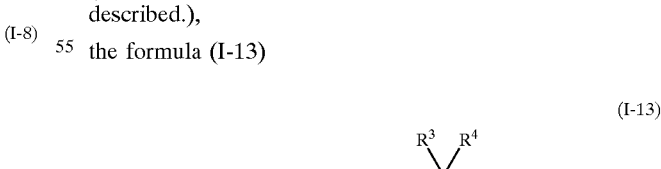
(I-12)

(wherein all symbols are the same meanings as hereinbefore described.), the formula (I-13)

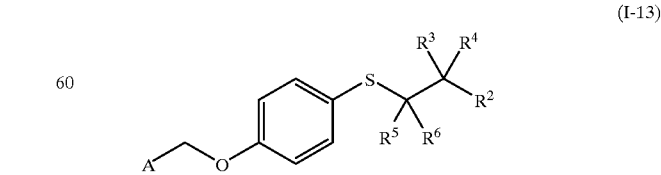
(I-13)

(wherein all symbols are the same meanings as hereinbefore described.), the formula (I-14)

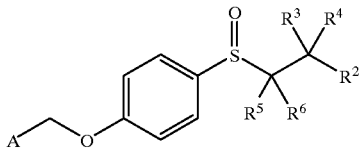
(I-14)

(wherein all symbols are the same meanings as hereinbefore described.), the formula (I-15)

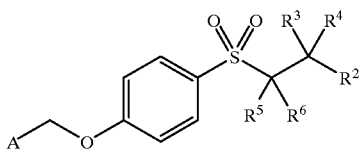
(I-15)

(wherein all symbols are the same meanings as hereinbefore described.), the formula (I-16)

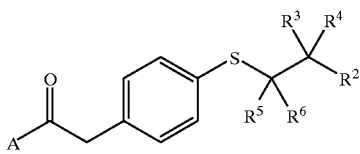
(I-16)

(wherein all symbols are the same meanings as hereinbefore described.), the formula (I-17)

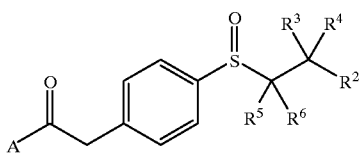
(I-17)

(wherein all symbols are the same meanings as hereinbefore described.), the formula (I-18)

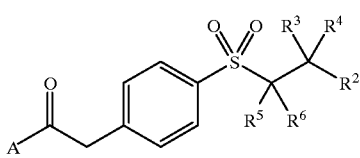
(I-18)

(wherein all symbols are the same meanings as hereinbefore described.), the formula (I-19)

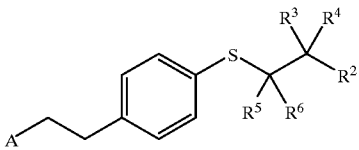
(I-19)

(wherein all symbols are the same meanings as hereinbefore described.), the formula (I-20)

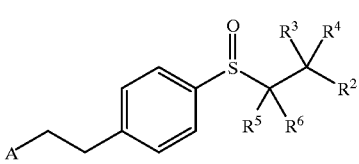
(I-20)

(wherein all symbols are the same meanings as hereinbefore described.), the formula (I-21)

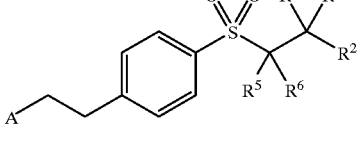
(I-21)

(wherein all symbols are the same meanings as hereinbefore described.), the formula (I-22)

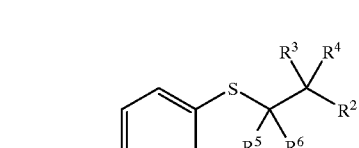
(I-22)

(wherein all symbols are the same meanings as hereinbefore described.), the formula (I-23)

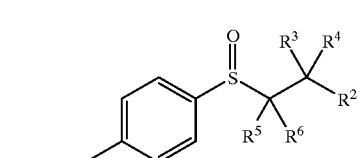
(I-23)

(wherein all symbols are the same meanings as hereinbefore described.), the formula (I-24)

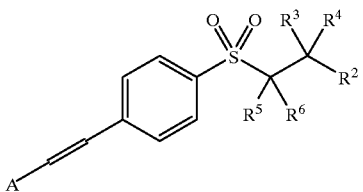
(I-24)

(wherein all symbols are the same meanings as hereinbefore described.),
the formula (I-25)

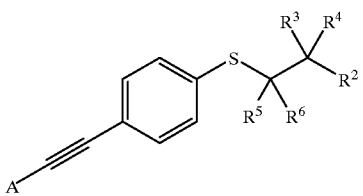
(I-25)

(wherein all symbols are the same meanings as hereinbefore described.),
the formula (I-26)

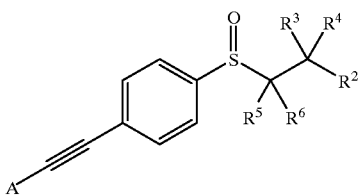
(I-26)

(wherein all symbols are the same meanings as hereinbefore described.),
the formula (I-27)

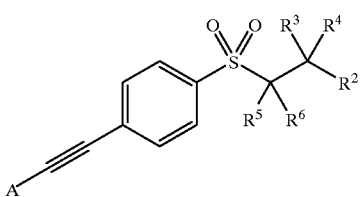
(I-27)

(wherein all symbols are the same meanings as hereinbefore described.),
the formula (I-28)

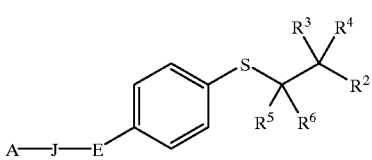
(I-28)

(wherein A, J and E taken together, represents methyl, halogen, trifluoromethyl, nitro, cyano, formyl, phenyl, hydroxy, $NR^{16}R^{17}$ (in which $R^{16}$ and $R^{17}$ are the same meanings as hereinbefore described.), heterocyclic ring (this heterocyclic ring may be optionally substituted by 1~4 of C1-4 alkyl, C1-4 alkoxy, halogen, trifluoromethyl, hydroxy, carboxyl, C1-8 alkoxycarbonyl, nitro, $NR^{24}R^{25}$ (in which $R^{24}$ and $R^{25}$ are the same meanings as hereinbefore described.) or $CONR^{24}R^{25}$ (in which $R^{24}$ and $R^{25}$ are the same meanings as hereinbefore described.).), the other symbols are the same meanings as hereinbefore described.),
the formula (I-29)

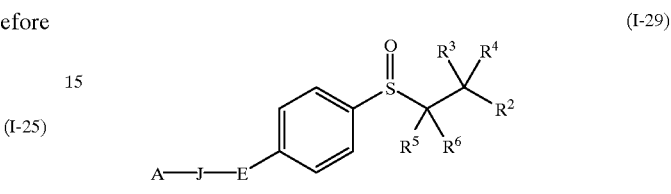
(I-29)

(wherein A, J and E taken together, represents methyl, halogen, trifluoromethyl, nitro, cyano, formyl, phenyl, hydroxy, $NR^{16}R^{17}$ (in which $R^{16}$ and $R^{17}$ are the same meanings as hereinbefore described.), heterocyclic ring (this heterocyclic ring may be optionally substituted by 1~4 of C1-4 alkyl, C1-4 alkoxy, halogen, trifluoromethyl, hydroxy, carboxyl, C1-8 alkoxycarbonyl, nitro, $NR^{24}R^{25}$ (in which $R^{24}$ and $R^{25}$ are the same meanings as hereinbefore described.) or $CONR^{24}R^{25}$ (in which $R^{24}$ and $R^{25}$ are the same meanings as hereinbefore described.).), the other symbols are the same meanings as hereinbefore described.),
the formula (I-30)

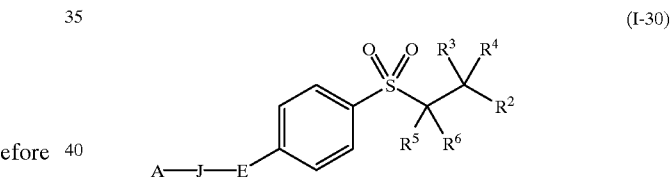
(I-30)

(wherein A, J and E taken together, represents methyl, halogen, trifluoromethyl, nitro, cyano, formyl, phenyl, hydroxy, $NR^{16}R^{17}$ (in which $R^{16}$ and $R^{17}$ are the same meanings as hereinbefore described.), heterocyclic ring (this heterocyclic ring may be optionally substituted by 1~4 of C1-4 alkyl, C1-4 alkoxy, halogen, trifluoromethyl, hydroxy, carboxyl, C1-8 alkoxycarbonyl, nitro, $NR^{24}R^{25}$ (in which $R^{24}$ and $R^{25}$ are the same meanings as hereinbefore described.) or $CONR^{24}R^{25}$ (in which $R^{24}$ and $R^{25}$ are the same meanings as hereinbefore described.).), the other symbols are the same meanings as hereinbefore described.).

The compounds wherein n is 2, that is, the above compounds of the formulae (I-3), (I-6), (I-9), (I-12), (I-15), (I-18), (I-21), (I-24), (I-27) and (I-30) are more preferred. In the more preferred compounds, the compounds in which E is —CONH—, —CH₂—O—, —CH=CH—, ethynylene, and in which A, J and E taken together, represents heterocyclic ring, that is, the above compounds of the formulae (I-3), (I-15), (I-24), (I-27) and (I-30) (with proviso that A, J and E taken together, represents heterocyclic ring.) are particularly preferred.

Examples of representative compounds are shown in the following Table and the compounds described in Example.

TABLE 1

(I-1a)

| No. | A | $R^4$ | $R^2$ |
|---|---|---|---|
| 1 | $C_5H_{11}-$ | H | COOH |
| 2 | $C_5H_{11}-$ | H | CONHOH |
| 3 | $C_5H_{11}-$ | $(H_3C)_2CH-$ (isopropyl) | COOH |
| 4 | $C_5H_{11}-$ | $(H_3C)_2CH-$ (isopropyl) | CONHOH |
| 5 | $C_5H_{11}-$ | $-CH_2OH$ | COOH |
| 6 | $C_5H_{11}-$ | $-CH_2OH$ | CONHOH |
| 7 | $C_5H_{11}-$ | benzyl | COOH |
| 8 | $C_5H_{11}-$ | benzyl | CONHOH |
| 9 | $C_5H_{11}-$ | 3-indolylmethyl | COOH |
| 10 | $C_5H_{11}-$ | 3-indolylmethyl | CONHOH |
| 11 | phenyl | H | COOH |
| 12 | phenyl | H | CONHOH |
| 13 | phenyl | $(H_3C)_2CH-$ | COOH |
| 14 | phenyl | $(H_3C)_2CH-$ | CONHOH |
| 15 | phenyl | $-CH_2OH$ | COOH |
| 16 | phenyl | $-CH_2OH$ | CONHOH |
| 17 | phenyl | benzyl | COOH |
| 18 | phenyl | benzyl | CONHOH |
| 19 | phenyl | 3-indolylmethyl | COOH |
| 20 | phenyl | 3-indolylmethyl | CONHOH |
| 21 | $H_3CO$-phenyl | H | COOH |
| 22 | $H_3CO$-phenyl | H | CONHOH |

TABLE 1-continued (I-1a)

| No. | A | R⁴ | R² |
|---|---|---|---|
| 23 | H₃CO—⟨⟩— | H₃C–CH(–)–CH₃ | COOH |
| 24 | H₃CO—⟨⟩— | H₃C–CH(–)–CH₃ | CONHOH |
| 25 | H₃CO—⟨⟩— | –CH₂CH₂OH | COOH |
| 26 | H₃CO—⟨⟩— | –CH₂CH₂OH | CONHOH |
| 27 | H₃CO—⟨⟩— | –CH₂–C₆H₅ | COOH |
| 28 | H₃CO—⟨⟩— | –CH₂–C₆H₅ | CONHOH |
| 29 | H₃CO—⟨⟩— | –CH₂-(3-indolyl) | COOH |
| 30 | H₃CO—⟨⟩— | –CH₂-(3-indolyl) | CONHOH |
| 31 | 2-thienyl– | H | COOH |

TABLE 1-continued (I-1a)

| No. | A | R⁴ | R² |
|---|---|---|---|
| 32 | 2-thienyl– | H | CONHOH |
| 33 | 2-thienyl– | H₃C–CH(–)–CH₃ | COOH |
| 34 | 2-thienyl– | H₃C–CH(–)–CH₃ | CONHOH |
| 35 | 2-thienyl– | –CH₂CH₂OH | COOH |
| 36 | 2-thienyl– | –CH₂CH₂OH | CONHOH |
| 37 | 2-thienyl– | –CH₂–C₆H₅ | COOH |
| 38 | 2-thienyl– | –CH₂–C₆H₅ | CONHOH |
| 39 | 2-thienyl– | –CH₂-(3-indolyl) | COOH |
| 40 | 2-thienyl– | –CH₂-(3-indolyl) | CONHOH |

TABLE 2

(I-2a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | $H_3C$-CH-$CH_3$ (isopropyl) | COOH |
| 4 | $C_5H_{11}-$ | $H_3C$-CH-$CH_3$ (isopropyl) | CONHOH |
| 5 | $C_5H_{11}-$ | -CH₂CH₂OH | COOH |
| 6 | $C_5H_{11}-$ | -CH₂CH₂OH | CONHOH |
| 7 | $C_5H_{11}-$ | -CH₂-Ph | COOH |
| 8 | $C_5H_{11}-$ | -CH₂-Ph | CONHOH |
| 9 | $C_5H_{11}-$ | -CH₂-(3-indolyl) | COOH |
| 10 | $C_5H_{11}-$ | -CH₂-(3-indolyl) | CONHOH |
| 11 | Ph- | H | COOH |
| 12 | Ph- | H | CONHOH |
| 13 | Ph- | $H_3C$-CH-$CH_3$ (isopropyl) | COOH |
| 14 | Ph- | $H_3C$-CH-$CH_3$ (isopropyl) | CONHOH |
| 15 | Ph- | -CH₂CH₂OH | COOH |
| 16 | Ph- | -CH₂CH₂OH | CONHOH |
| 17 | Ph- | -CH₂-Ph | COOH |
| 18 | Ph- | -CH₂-Ph | CONHOH |
| 19 | Ph- | -CH₂-(3-indolyl) | COOH |
| 20 | Ph- | -CH₂-(3-indolyl) | CONHOH |
| 21 | 4-$H_3CO$-C₆H₄- | H | COOH |
| 22 | 4-$H_3CO$-C₆H₄- | H | CONHOH |

TABLE 2-continued
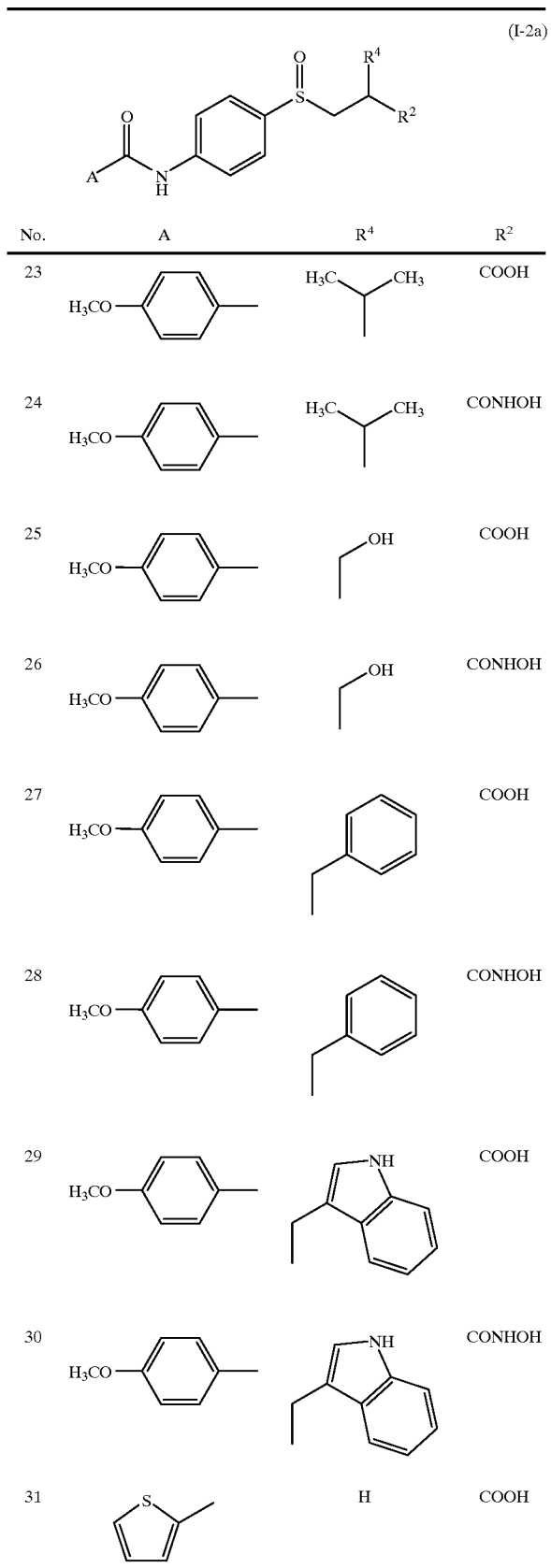
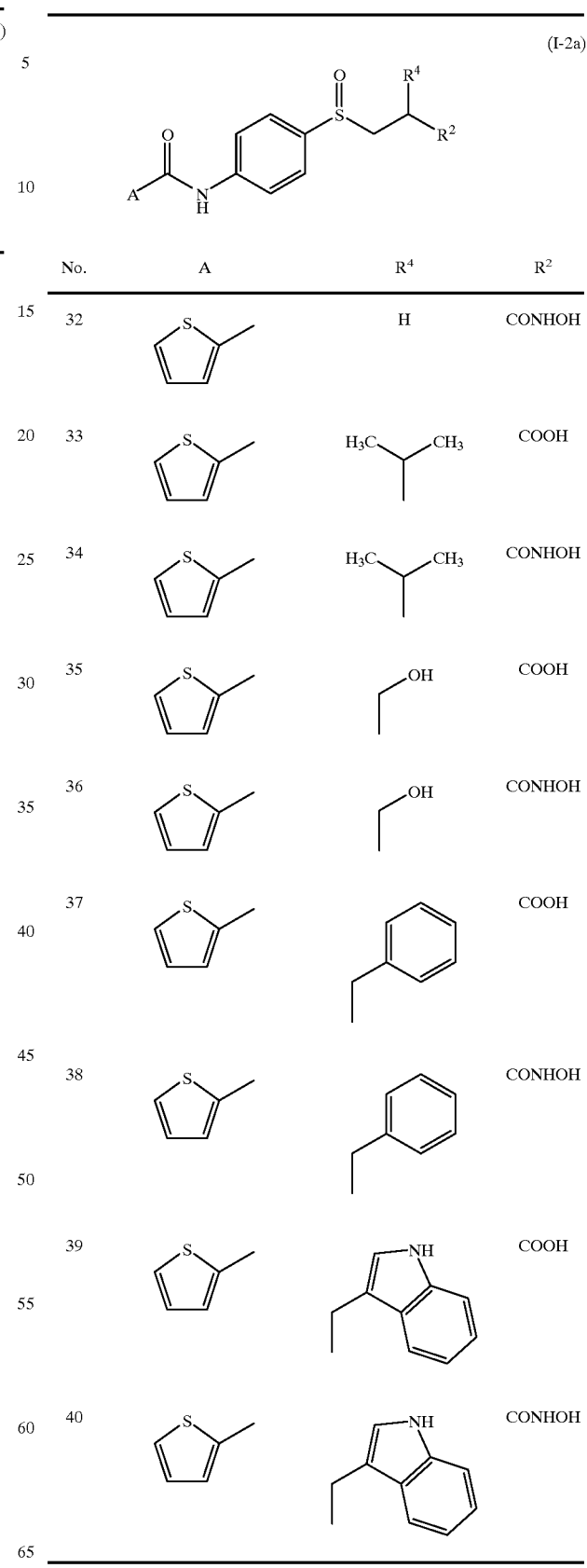

TABLE 3

(I-3a)

A-C(=O)-NH-C₆H₄-S-CH₂-CH(R⁴)(R²)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | —CH₂CH₂OH | COOH |
| 6 | C₅H₁₁— | —CH₂CH₂OH | CONHOH |
| 7 | C₅H₁₁— | benzyl (—CH₂—C₆H₅) | COOH |
| 8 | C₅H₁₁— | benzyl (—CH₂—C₆H₅) | CONHOH |
| 9 | C₅H₁₁— | 3-indolylmethyl | COOH |
| 10 | C₅H₁₁— | 3-indolylmethyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | —CH₂CH₂OH | COOH |
| 16 | phenyl | —CH₂CH₂OH | CONHOH |
| 17 | phenyl | benzyl | COOH |
| 18 | phenyl | benzyl | CONHOH |
| 19 | phenyl | 3-indolylmethyl | COOH |
| 20 | phenyl | 3-indolylmethyl | CONHOH |
| 21 | 4-methoxyphenyl (H₃CO—C₆H₄—) | H | COOH |
| 22 | 4-methoxyphenyl (H₃CO—C₆H₄—) | H | CONHOH |

TABLE 3-continued (I-3a)

Structure: A-C(=O)-NH-[phenyl]-S-CH2-C(R4)(R2)H

| No. | A | R⁴ | R² |
|-----|---|----|----|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl- | H | COOH |
| 32 | 2-thienyl- | H | CONHOH |
| 33 | 2-thienyl- | -CH(CH₃)₂ | COOH |
| 34 | 2-thienyl- | -CH(CH₃)₂ | CONHOH |
| 35 | 2-thienyl- | -CH₂OH | COOH |
| 36 | 2-thienyl- | -CH₂OH | CONHOH |
| 37 | 2-thienyl- | -CH₂-C₆H₅ | COOH |
| 38 | 2-thienyl- | -CH₂-C₆H₅ | CONHOH |
| 39 | 2-thienyl- | -CH₂-(3-indolyl) | COOH |
| 40 | 2-thienyl- | -CH₂-(3-indolyl) | CONHOH |

TABLE 4

(I-4a)

A structure showing: A-NH-C(=O)-[phenyl]-S-CH2-C(R4)(R2)

| No. | A | R⁴ | R² |
|-----|---|-----|-----|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | CH₂CH₂OH | COOH |
| 6 | C₅H₁₁— | CH₂CH₂OH | CONHOH |
| 7 | C₅H₁₁— | benzyl | COOH |
| 8 | C₅H₁₁— | benzyl | CONHOH |
| 9 | C₅H₁₁— | (1H-indol-3-yl)methyl | COOH |
| 10 | C₅H₁₁— | (1H-indol-3-yl)methyl | CONHOH |
| 11 | phenyl | H | COOH |
| 12 | phenyl | H | CONHOH |

TABLE 4-continued (I-4a)

| No. | A | R⁴ | R² |
|-----|---|-----|-----|
| 13 | phenyl | isopropyl (H₃C-CH-CH₃) | COOH |
| 14 | phenyl | isopropyl (H₃C-CH-CH₃) | CONHOH |
| 15 | phenyl | CH₂CH₂OH | COOH |
| 16 | phenyl | CH₂CH₂OH | CONHOH |
| 17 | phenyl | benzyl | COOH |
| 18 | phenyl | benzyl | CONHOH |
| 19 | phenyl | (1H-indol-3-yl)methyl | COOH |
| 20 | phenyl | (1H-indol-3-yl)methyl | CONHOH |
| 21 | 4-H₃CO-phenyl | H | COOH |
| 22 | 4-H₃CO-phenyl | H | CONHOH |

TABLE 4-continued (I-4a)

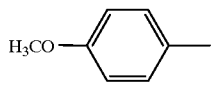

| No. | A | R⁴ | R² |
|---|---|---|---|
| 23 | H₃CO-C₆H₄- | H₃C-CH(-)-CH₃ | COOH |
| 24 | H₃CO-C₆H₄- | H₃C-CH(-)-CH₃ | CONHOH |
| 25 | H₃CO-C₆H₄- | -CH₂CH₂OH | COOH |
| 26 | H₃CO-C₆H₄- | -CH₂CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | H₃C-CH(-)-CH₃ | COOH |
| 34 | 2-thienyl | H₃C-CH(-)-CH₃ | CONHOH |
| 35 | 2-thienyl | -CH₂CH₂OH | COOH |
| 36 | 2-thienyl | -CH₂CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 5

(I-5a)

A-NH-C(=O)-C6H4-S(=O)-CH2-CH(R4)(R2)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl | COOH |
| 4 | C₅H₁₁— | isopropyl | CONHOH |
| 5 | C₅H₁₁— | CH₂OH | COOH |
| 6 | C₅H₁₁— | CH₂OH | CONHOH |
| 7 | C₅H₁₁— | CH₂-phenyl | COOH |
| 8 | C₅H₁₁— | CH₂-phenyl | CONHOH |
| 9 | C₅H₁₁— | CH₂-(1H-indol-3-yl) | COOH |
| 10 | C₅H₁₁— | CH₂-(1H-indol-3-yl) | CONHOH |
| 11 | phenyl— | H | COOH |
| 12 | phenyl— | H | CONHOH |
| 13 | phenyl— | isopropyl | COOH |
| 14 | phenyl— | isopropyl | CONHOH |
| 15 | phenyl— | CH₂OH | COOH |
| 16 | phenyl— | CH₂OH | CONHOH |
| 17 | phenyl— | CH₂-phenyl | COOH |
| 18 | phenyl— | CH₂-phenyl | CONHOH |
| 19 | phenyl— | CH₂-(1H-indol-3-yl) | COOH |
| 20 | phenyl— | CH₂-(1H-indol-3-yl) | CONHOH |
| 21 | 4-CH₃O-phenyl— | H | COOH |
| 22 | 4-CH₃O-phenyl— | H | CONHOH |

TABLE 5-continued (I-5a)

[Structure: A-NH-C(=O)-C6H4-S(=O)-CH2-CH(R4)(R2)]

| No. | A | R⁴ | R² |
|---|---|---|---|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(1H-indol-3-yl) | COOH |
| 30 | 4-H₃CO-C₆H₄- | -CH₂-(1H-indol-3-yl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(1H-indol-3-yl) | COOH |
| 40 | 2-thienyl | -CH₂-(1H-indol-3-yl) | CONHOH |

TABLE 6

(I-6a)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl | COOH |
| 4 | C₅H₁₁— | isopropyl | CONHOH |
| 5 | C₅H₁₁— | CH₂CH₂OH | COOH |
| 6 | C₅H₁₁— | CH₂CH₂OH | CONHOH |
| 7 | C₅H₁₁— | benzyl | COOH |
| 8 | C₅H₁₁— | benzyl | CONHOH |
| 9 | C₅H₁₁— | (indol-3-yl)methyl | COOH |
| 10 | C₅H₁₁— | (indol-3-yl)methyl | CONHOH |
| 11 | phenyl— | H | COOH |
| 12 | phenyl— | H | CONHOH |
| 13 | phenyl— | isopropyl | COOH |
| 14 | phenyl— | isopropyl | CONHOH |
| 15 | phenyl— | CH₂CH₂OH | COOH |
| 16 | phenyl— | CH₂CH₂OH | CONHOH |
| 17 | phenyl— | benzyl | COOH |
| 18 | phenyl— | benzyl | CONHOH |
| 19 | phenyl— | (indol-3-yl)methyl | COOH |
| 20 | phenyl— | (indol-3-yl)methyl | CONHOH |
| 21 | 4-MeO-C₆H₄— | H | COOH |
| 22 | 4-MeO-C₆H₄— | H | CONHOH |

TABLE 6-continued (I-6a)

| No. | A | R⁴ | R² |
|---|---|---|---|
| 23 | H₃CO-C₆H₄- | H₃C-CH(CH₃)- | COOH |
| 24 | H₃CO-C₆H₄- | H₃C-CH(CH₃)- | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | H₃C-CH(CH₃)- | COOH |
| 34 | 2-thienyl | H₃C-CH(CH₃)- | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 7

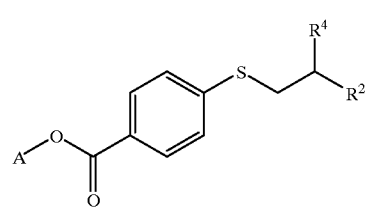
(I-7a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | $H_3C-CH(-)-CH_3$ (isopropyl) | COOH |
| 4 | $C_5H_{11}-$ | $H_3C-CH(-)-CH_3$ (isopropyl) | CONHOH |
| 5 | $C_5H_{11}-$ | -CH₂CH₂OH | COOH |
| 6 | $C_5H_{11}-$ | -CH₂CH₂OH | CONHOH |
| 7 | $C_5H_{11}-$ | benzyl (-CH₂-C₆H₅) | COOH |
| 8 | $C_5H_{11}-$ | benzyl (-CH₂-C₆H₅) | CONHOH |
| 9 | $C_5H_{11}-$ | 3-indolylmethyl | COOH |
| 10 | $C_5H_{11}-$ | 3-indolylmethyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | -CH₂CH₂OH | COOH |
| 16 | phenyl | -CH₂CH₂OH | CONHOH |
| 17 | phenyl | benzyl | COOH |
| 18 | phenyl | benzyl | CONHOH |
| 19 | phenyl | 3-indolylmethyl | COOH |
| 20 | phenyl | 3-indolylmethyl | CONHOH |
| 21 | 4-methoxyphenyl | H | COOH |
| 22 | 4-methoxyphenyl | H | CONHOH |

TABLE 7-continued
(I-7a)
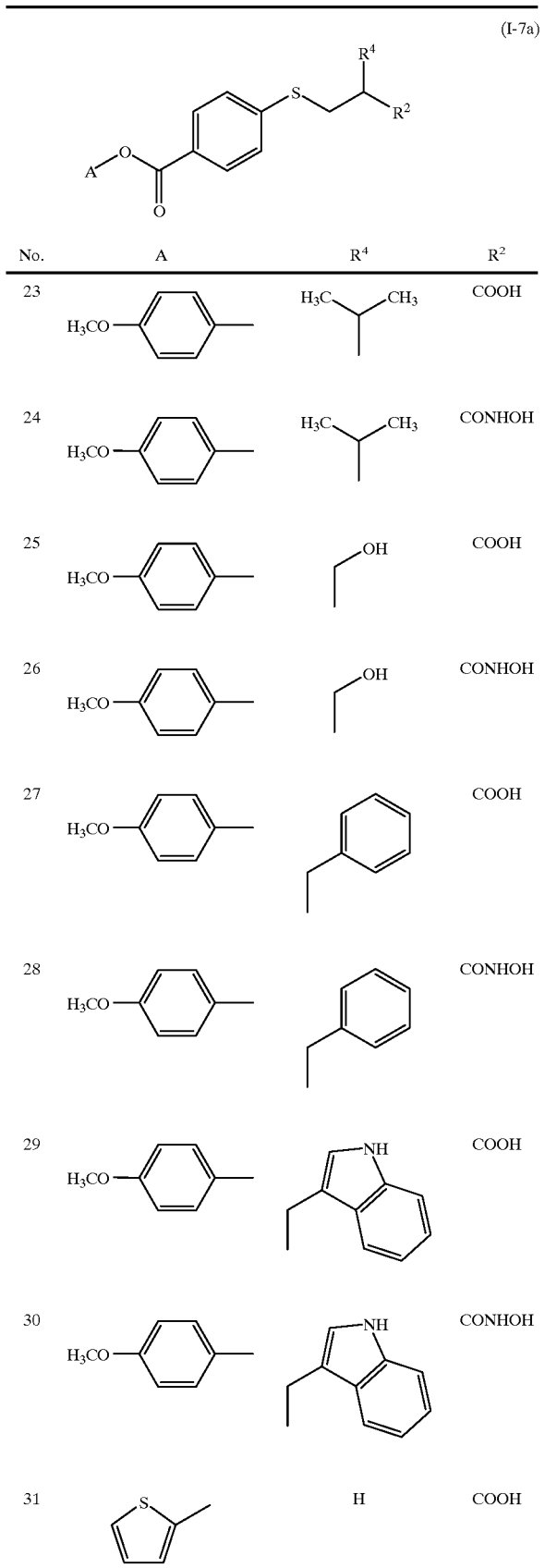
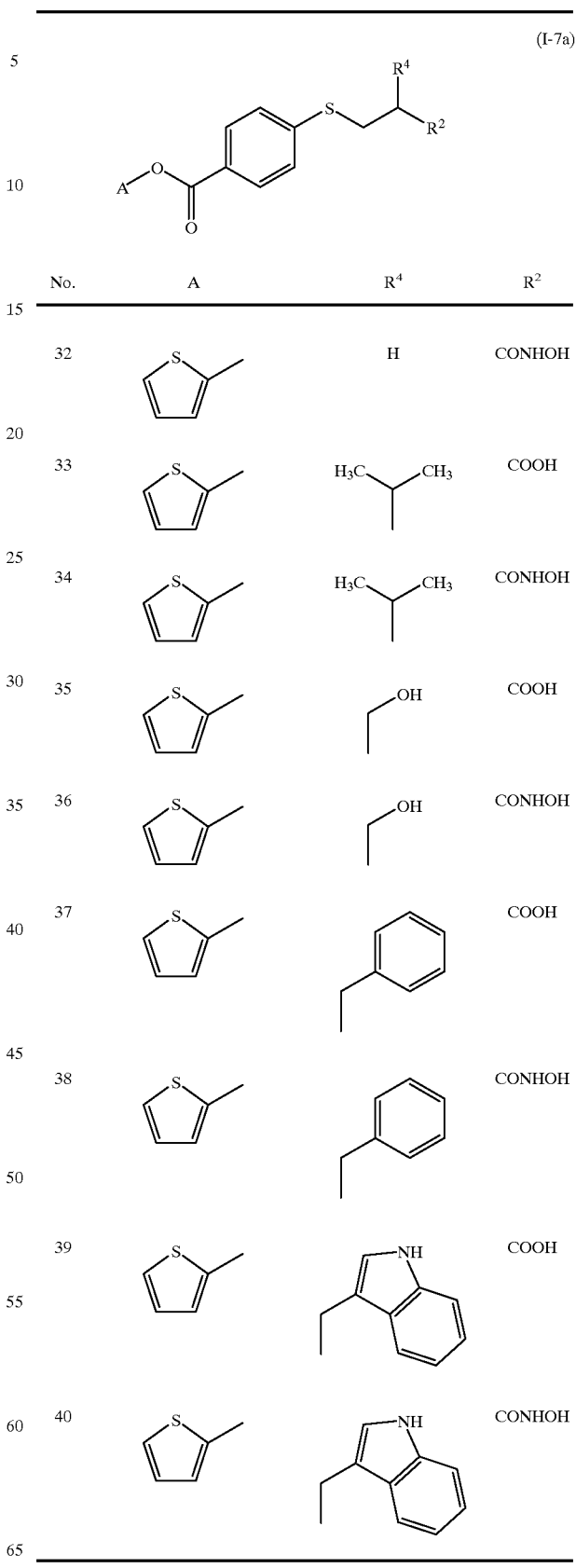

TABLE 8

(I-8a)

[Structure: A-O-C(=O)-C6H4-S(=O)-CH2-CH(R4)-R2]

| No. | A | R4 | R2 |
|---|---|---|---|
| 1 | $C_5H_{11}-$ | H | COOH |
| 2 | $C_5H_{11}-$ | H | CONHOH |
| 3 | $C_5H_{11}-$ | isopropyl (H3C-CH-CH3) | COOH |
| 4 | $C_5H_{11}-$ | isopropyl (H3C-CH-CH3) | CONHOH |
| 5 | $C_5H_{11}-$ | -CH2CH2OH | COOH |
| 6 | $C_5H_{11}-$ | -CH2CH2OH | CONHOH |
| 7 | $C_5H_{11}-$ | -CH2-C6H5 | COOH |
| 8 | $C_5H_{11}-$ | -CH2-C6H5 | CONHOH |
| 9 | $C_5H_{11}-$ | -CH2-(3-indolyl) | COOH |
| 10 | $C_5H_{11}-$ | -CH2-(3-indolyl) | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | -CH2CH2OH | COOH |
| 16 | phenyl | -CH2CH2OH | CONHOH |
| 17 | phenyl | -CH2-C6H5 | COOH |
| 18 | phenyl | -CH2-C6H5 | CONHOH |
| 19 | phenyl | -CH2-(3-indolyl) | COOH |
| 20 | phenyl | -CH2-(3-indolyl) | CONHOH |
| 21 | 4-methoxyphenyl (H3CO-C6H4-) | H | COOH |
| 22 | 4-methoxyphenyl (H3CO-C6H4-) | H | CONHOH |

TABLE 8-continued (I-8a)

Structure: A-O-C(=O)-C6H4-S(=O)-CH2-CH(R4)(R2)

| No. | A | R⁴ | R² |
|---|---|---|---|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl- | H | COOH |
| 32 | 2-thienyl- | H | CONHOH |
| 33 | 2-thienyl- | -CH(CH₃)₂ | COOH |
| 34 | 2-thienyl- | -CH(CH₃)₂ | CONHOH |
| 35 | 2-thienyl- | -CH₂OH | COOH |
| 36 | 2-thienyl- | -CH₂OH | CONHOH |
| 37 | 2-thienyl- | -CH₂-C₆H₅ | COOH |
| 38 | 2-thienyl- | -CH₂-C₆H₅ | CONHOH |
| 39 | 2-thienyl- | -CH₂-(3-indolyl) | COOH |
| 40 | 2-thienyl- | -CH₂-(3-indolyl) | CONHOH |

TABLE 9

(I-9a)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isobutyl (H₃C-CH-CH₃) | COOH |
| 4 | C₅H₁₁— | isobutyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | -CH₂-C₆H₅ | COOH |
| 8 | C₅H₁₁— | -CH₂-C₆H₅ | CONHOH |
| 9 | C₅H₁₁— | -CH₂-(3-indolyl) | COOH |
| 10 | C₅H₁₁— | -CH₂-(3-indolyl) | CONHOH |
| 11 | C₆H₅— | H | COOH |
| 12 | C₆H₅— | H | CONHOH |

TABLE 9-continued (I-9a)

| No. | A | R⁴ | R² |
|---|---|---|---|
| 13 | C₆H₅— | isobutyl (H₃C-CH-CH₃) | COOH |
| 14 | C₆H₅— | isobutyl (H₃C-CH-CH₃) | CONHOH |
| 15 | C₆H₅— | -CH₂CH₂OH | COOH |
| 16 | C₆H₅— | -CH₂CH₂OH | CONHOH |
| 17 | C₆H₅— | -CH₂-C₆H₅ | COOH |
| 18 | C₆H₅— | -CH₂-C₆H₅ | CONHOH |
| 19 | C₆H₅— | -CH₂-(3-indolyl) | COOH |
| 20 | C₆H₅— | -CH₂-(3-indolyl) | CONHOH |
| 21 | 4-H₃CO-C₆H₄— | H | COOH |
| 22 | 4-H₃CO-C₆H₄— | H | CONHOH |

TABLE 9-continued (I-9a)

[Structure: A-O-C(=O)-C6H4-S(=O)-CH2-CH(R4)(R2)]

| No. | A | R⁴ | R² |
|---|---|---|---|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 10

(I-10a)

[Structure: A-C(=O)-O-phenyl-S-CH2-CH(R4)(R2)]

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂OH | COOH |
| 6 | C₅H₁₁— | -CH₂OH | CONHOH |
| 7 | C₅H₁₁— | -CH₂-phenyl | COOH |
| 8 | C₅H₁₁— | -CH₂-phenyl | CONHOH |
| 9 | C₅H₁₁— | -CH₂-(3-indolyl) | COOH |
| 10 | C₅H₁₁— | -CH₂-(3-indolyl) | CONHOH |
| 11 | phenyl— | H | COOH |
| 12 | phenyl— | H | CONHOH |
| 13 | phenyl— | isopropyl (H₃C-CH-CH₃) | COOH |
| 14 | phenyl— | isopropyl (H₃C-CH-CH₃) | CONHOH |
| 15 | phenyl— | -CH₂OH | COOH |
| 16 | phenyl— | -CH₂OH | CONHOH |
| 17 | phenyl— | -CH₂-phenyl | COOH |
| 18 | phenyl— | -CH₂-phenyl | CONHOH |
| 19 | phenyl— | -CH₂-(3-indolyl) | COOH |
| 20 | phenyl— | -CH₂-(3-indolyl) | CONHOH |
| 21 | 4-H₃CO-phenyl— | H | COOH |
| 22 | 4-H₃CO-phenyl— | H | CONHOH |

TABLE 10-continued (I-10a)

A—C(=O)—O—[phenyl]—S—CH2—CH(R4)—R2

| No. | A | R4 | R2 |
|---|---|---|---|
| 23 | H3CO—C6H4— | CH(CH3)2 | COOH |
| 24 | H3CO—C6H4— | CH(CH3)2 | CONHOH |
| 25 | H3CO—C6H4— | CH2OH | COOH |
| 26 | H3CO—C6H4— | CH2OH | CONHOH |
| 27 | H3CO—C6H4— | CH2-C6H5 | COOH |
| 28 | H3CO—C6H4— | CH2-C6H5 | CONHOH |
| 29 | H3CO—C6H4— | CH2-(3-indolyl) | COOH |
| 30 | H3CO—C6H4— | CH2-(3-indolyl) | CONHOH |
| 31 | 2-thienyl | H | COOH |
| 32 | 2-thienyl | H | CONHOH |
| 33 | 2-thienyl | CH(CH3)2 | COOH |
| 34 | 2-thienyl | CH(CH3)2 | CONHOH |
| 35 | 2-thienyl | CH2OH | COOH |
| 36 | 2-thienyl | CH2OH | CONHOH |
| 37 | 2-thienyl | CH2-C6H5 | COOH |
| 38 | 2-thienyl | CH2-C6H5 | CONHOH |
| 39 | 2-thienyl | CH2-(3-indolyl) | COOH |
| 40 | 2-thienyl | CH2-(3-indolyl) | CONHOH |

TABLE 11

(I-11a)

Structure: A-C(=O)-O-[phenyl]-S(=O)-CH2-CH(R4)(R2)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂-OH | COOH |
| 6 | C₅H₁₁— | -CH₂-OH | CONHOH |
| 7 | C₅H₁₁— | -CH₂-phenyl | COOH |
| 8 | C₅H₁₁— | -CH₂-phenyl | CONHOH |
| 9 | C₅H₁₁— | -CH₂-(1H-indol-3-yl) | COOH |
| 10 | C₅H₁₁— | -CH₂-(1H-indol-3-yl) | CONHOH |
| 11 | phenyl- | H | COOH |
| 12 | phenyl- | H | CONHOH |
| 13 | phenyl- | isopropyl (H₃C-CH-CH₃) | COOH |
| 14 | phenyl- | isopropyl (H₃C-CH-CH₃) | CONHOH |
| 15 | phenyl- | -CH₂-OH | COOH |
| 16 | phenyl- | -CH₂-OH | CONHOH |
| 17 | phenyl- | -CH₂-phenyl | COOH |
| 18 | phenyl- | -CH₂-phenyl | CONHOH |
| 19 | phenyl- | -CH₂-(1H-indol-3-yl) | COOH |
| 20 | phenyl- | -CH₂-(1H-indol-3-yl) | CONHOH |
| 21 | 4-H₃CO-phenyl- | H | COOH |
| 22 | 4-H₃CO-phenyl- | H | CONHOH |

TABLE 11-continued (I-11a)

Structure: A-C(=O)-O-[phenyl]-S(=O)-CH₂-CH(R⁴)-R²

| No. | A | R⁴ | R² |
|---|---|---|---|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl- | H | COOH |
| 32 | 2-thienyl- | H | CONHOH |
| 33 | 2-thienyl- | -CH(CH₃)₂ | COOH |
| 34 | 2-thienyl- | -CH(CH₃)₂ | CONHOH |
| 35 | 2-thienyl- | -CH₂OH | COOH |
| 36 | 2-thienyl- | -CH₂OH | CONHOH |
| 37 | 2-thienyl- | -CH₂-C₆H₅ | COOH |
| 38 | 2-thienyl- | -CH₂-C₆H₅ | CONHOH |
| 39 | 2-thienyl- | -CH₂-(3-indolyl) | COOH |
| 40 | 2-thienyl- | -CH₂-(3-indolyl) | CONHOH |

TABLE 12

(I-12a)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isobutyl (H₃C-CH-CH₃) | COOH |
| 4 | C₅H₁₁— | isobutyl (H₃C-CH-CH₃) | CONHOH |
| 5 | C₅H₁₁— | —CH₂CH₂OH | COOH |
| 6 | C₅H₁₁— | —CH₂CH₂OH | CONHOH |
| 7 | C₅H₁₁— | —CH₂-C₆H₅ | COOH |
| 8 | C₅H₁₁— | —CH₂-C₆H₅ | CONHOH |
| 9 | C₅H₁₁— | —CH₂-(3-indolyl) | COOH |
| 10 | C₅H₁₁— | —CH₂-(3-indolyl) | CONHOH |
| 11 | C₆H₅— | H | COOH |
| 12 | C₆H₅— | H | CONHOH |
| 13 | C₆H₅— | isobutyl (H₃C-CH-CH₃) | COOH |
| 14 | C₆H₅— | isobutyl (H₃C-CH-CH₃) | CONHOH |
| 15 | C₆H₅— | —CH₂CH₂OH | COOH |
| 16 | C₆H₅— | —CH₂CH₂OH | CONHOH |
| 17 | C₆H₅— | —CH₂-C₆H₅ | COOH |
| 18 | C₆H₅— | —CH₂-C₆H₅ | CONHOH |
| 19 | C₆H₅— | —CH₂-(3-indolyl) | COOH |
| 20 | C₆H₅— | —CH₂-(3-indolyl) | CONHOH |
| 21 | 4-H₃CO-C₆H₄— | H | COOH |
| 22 | 4-H₃CO-C₆H₄— | H | CONHOH |

TABLE 12-continued (I-12a)

[Structure: A-C(=O)-O-phenyl-S(=O)₂-CH₂-CH(R⁴)(R²)]

| No. | A | R⁴ | R² |
|---|---|---|---|
| 23 | H₃CO-C₆H₄- | -CH(CH₃)₂ | COOH |
| 24 | H₃CO-C₆H₄- | -CH(CH₃)₂ | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 13

(I-13a)

Structure: A-O-C6H4-S-CH2-CH(R4)(R2)

| No. | A | R4 | R2 |
|---|---|---|---|
| 1 | C5H11— | H | COOH |
| 2 | C5H11— | H | CONHOH |
| 3 | C5H11— | isobutyl (H3C-CH-CH3) | COOH |
| 4 | C5H11— | isobutyl (H3C-CH-CH3) | CONHOH |
| 5 | C5H11— | CH2CH2OH | COOH |
| 6 | C5H11— | CH2CH2OH | CONHOH |
| 7 | C5H11— | CH2-C6H5 (benzyl) | COOH |
| 8 | C5H11— | CH2-C6H5 (benzyl) | CONHOH |
| 9 | C5H11— | CH2-(3-indolyl) | COOH |
| 10 | C5H11— | CH2-(3-indolyl) | CONHOH |
| 11 | phenyl | H | COOH |
| 12 | phenyl | H | CONHOH |
| 13 | phenyl | isobutyl | COOH |
| 14 | phenyl | isobutyl | CONHOH |
| 15 | phenyl | CH2CH2OH | COOH |
| 16 | phenyl | CH2CH2OH | CONHOH |
| 17 | phenyl | CH2-C6H5 (benzyl) | COOH |
| 18 | phenyl | CH2-C6H5 (benzyl) | CONHOH |
| 19 | phenyl | CH2-(3-indolyl) | COOH |
| 20 | phenyl | CH2-(3-indolyl) | CONHOH |
| 21 | 4-H3CO-C6H4— | H | COOH |
| 22 | 4-H3CO-C6H4— | H | CONHOH |

TABLE 13-continued (I-13a)

| No. | A | R⁴ | R² |
|---|---|---|---|
| 23 | 4-H₃CO-C₆H₄- | (CH₃)₂CH- | COOH |
| 24 | 4-H₃CO-C₆H₄- | (CH₃)₂CH- | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂C₆H₅ | COOH |
| 28 | 4-H₃CO-C₆H₄- | -CH₂C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | (CH₃)₂CH- | COOH |
| 34 | 2-thienyl | (CH₃)₂CH- | CONHOH |
| 35 | 2-thienyl | -CH₂OH | COOH |
| 36 | 2-thienyl | -CH₂OH | CONHOH |
| 37 | 2-thienyl | -CH₂C₆H₅ | COOH |
| 38 | 2-thienyl | -CH₂C₆H₅ | CONHOH |
| 39 | 2-thienyl | -CH₂-(3-indolyl) | COOH |
| 40 | 2-thienyl | -CH₂-(3-indolyl) | CONHOH |

TABLE 14

(I-14a)

[Structure: A-O-C6H4-S(=O)-CH2-CH(R4)(R2)]

| No. | A | R⁴ | R² |
|---|---|---|---|
| 1 | C₅H₁₁— | H | COOH |
| 2 | C₅H₁₁— | H | CONHOH |
| 3 | C₅H₁₁— | isobutyl (H₃C-CH-CH₃) | COOH |
| 4 | C₅H₁₁— | isobutyl (H₃C-CH-CH₃) | CONHOH |
| 5 | C₅H₁₁— | CH₂CH₂OH | COOH |
| 6 | C₅H₁₁— | CH₂CH₂OH | CONHOH |
| 7 | C₅H₁₁— | benzyl (CH₂-C₆H₅) | COOH |
| 8 | C₅H₁₁— | benzyl (CH₂-C₆H₅) | CONHOH |
| 9 | C₅H₁₁— | 3-indolylmethyl | COOH |
| 10 | C₅H₁₁— | 3-indolylmethyl | CONHOH |
| 11 | phenyl | H | COOH |
| 12 | phenyl | H | CONHOH |

TABLE 14-continued (I-14a)

[Structure: A-O-C6H4-S(=O)-CH2-CH(R4)(R2)]

| No. | A | R⁴ | R² |
|---|---|---|---|
| 13 | phenyl | isobutyl (H₃C-CH-CH₃) | COOH |
| 14 | phenyl | isobutyl (H₃C-CH-CH₃) | CONHOH |
| 15 | phenyl | CH₂CH₂OH | COOH |
| 16 | phenyl | CH₂CH₂OH | CONHOH |
| 17 | phenyl | benzyl (CH₂-C₆H₅) | COOH |
| 18 | phenyl | benzyl (CH₂-C₆H₅) | CONHOH |
| 19 | phenyl | 3-indolylmethyl | COOH |
| 20 | phenyl | 3-indolylmethyl | CONHOH |
| 21 | H₃CO-C₆H₄- | H | COOH |
| 22 | H₃CO-C₆H₄- | H | CONHOH |

TABLE 14-continued $$\text{(I-14a)}$$

A-O-⟨C6H4⟩-S(=O)-CH2-CH(R4)(R2)

| No. | A | R⁴ | R² |
|---|---|---|---|
| 23 | H₃CO-C₆H₄- | -CH(CH₃)₂ | COOH |
| 24 | H₃CO-C₆H₄- | -CH(CH₃)₂ | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂C₆H₅ | COOH |
| 28 | H₃CO-C₆H₄- | -CH₂C₆H₅ | CONHOH |
| 29 | H₃CO-C₆H₄- | -CH₂(3-indolyl) | COOH |
| 30 | H₃CO-C₆H₄- | -CH₂(3-indolyl) | CONHOH |
| 31 | 2-thienyl- | H | COOH |
| 32 | 2-thienyl- | H | CONHOH |
| 33 | 2-thienyl- | -CH(CH₃)₂ | COOH |
| 34 | 2-thienyl- | -CH(CH₃)₂ | CONHOH |
| 35 | 2-thienyl- | -CH₂OH | COOH |
| 36 | 2-thienyl- | -CH₂OH | CONHOH |
| 37 | 2-thienyl- | -CH₂C₆H₅ | COOH |
| 38 | 2-thienyl- | -CH₂C₆H₅ | CONHOH |
| 39 | 2-thienyl- | -CH₂(3-indolyl) | COOH |
| 40 | 2-thienyl- | -CH₂(3-indolyl) | CONHOH |

TABLE 15

(I-15a)

Structure: A—O—C6H4—S(O)2—CH2—CH(R4)(R2)

| No. | A | R4 | R2 |
|-----|---|----|----|
| 1 | C5H11— | H | COOH |
| 2 | C5H11— | H | CONHOH |
| 3 | C5H11— | isobutyl (H3C-CH-CH3) | COOH |
| 4 | C5H11— | isobutyl (H3C-CH-CH3) | CONHOH |
| 5 | C5H11— | —CH2CH2OH | COOH |
| 6 | C5H11— | —CH2CH2OH | CONHOH |
| 7 | C5H11— | —CH2-C6H5 | COOH |
| 8 | C5H11— | —CH2-C6H5 | CONHOH |
| 9 | C5H11— | —CH2-(3-indolyl) | COOH |
| 10 | C5H11— | —CH2-(3-indolyl) | CONHOH |
| 11 | C6H5-CH2— | H | COOH |
| 12 | C6H5-CH2— | H | CONHOH |
| 13 | C6H5-CH2— | isobutyl (H3C-CH-CH3) | COOH |
| 14 | C6H5-CH2— | isobutyl (H3C-CH-CH3) | CONHOH |
| 15 | C6H5-CH2— | —CH2CH2OH | COOH |
| 16 | C6H5-CH2— | —CH2CH2OH | CONHOH |
| 17 | C6H5-CH2— | —CH2-C6H5 | COOH |
| 18 | C6H5-CH2— | —CH2-C6H5 | CONHOH |
| 19 | C6H5-CH2— | —CH2-(3-indolyl) | COOH |
| 20 | C6H5-CH2— | —CH2-(3-indolyl) | CONHOH |
| 21 | 4-H3CO-C6H4-CH2— | H | COOH |
| 22 | 4-H3CO-C6H4-CH2— | H | CONHOH |

TABLE 15-continued
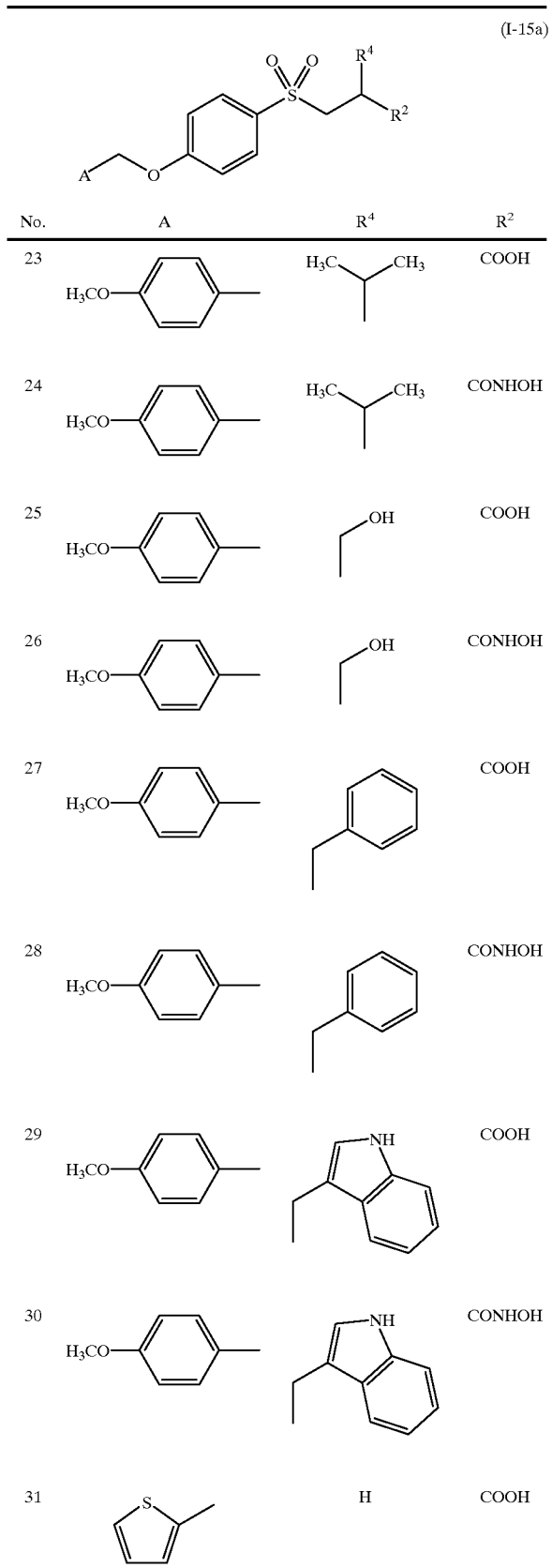
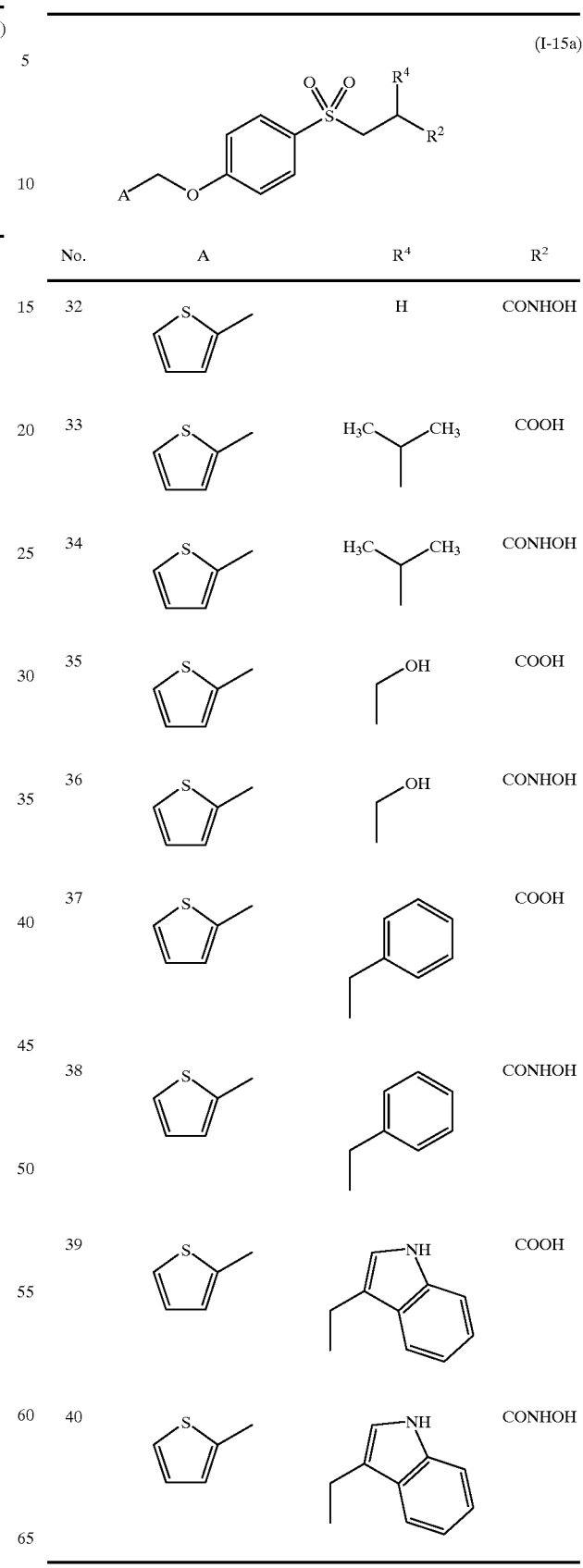

TABLE 16

(I-16a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | isobutyl (H₃C-CH-CH₃) | COOH |
| 4 | $C_5H_{11}-$ | isobutyl (H₃C-CH-CH₃) | CONHOH |
| 5 | $C_5H_{11}-$ | -CH₂CH₂OH | COOH |
| 6 | $C_5H_{11}-$ | -CH₂CH₂OH | CONHOH |
| 7 | $C_5H_{11}-$ | -CH₂-phenyl | COOH |
| 8 | $C_5H_{11}-$ | -CH₂-phenyl | CONHOH |
| 9 | $C_5H_{11}-$ | -CH₂-(3-indolyl) | COOH |
| 10 | $C_5H_{11}-$ | -CH₂-(3-indolyl) | CONHOH |
| 11 | phenyl | H | COOH |
| 12 | phenyl | H | CONHOH |
| 13 | phenyl | isobutyl | COOH |
| 14 | phenyl | isobutyl | CONHOH |
| 15 | phenyl | -CH₂CH₂OH | COOH |
| 16 | phenyl | -CH₂CH₂OH | CONHOH |
| 17 | phenyl | -CH₂-phenyl | COOH |
| 18 | phenyl | -CH₂-phenyl | CONHOH |
| 19 | phenyl | -CH₂-(3-indolyl) | COOH |
| 20 | phenyl | -CH₂-(3-indolyl) | CONHOH |
| 21 | 4-CH₃O-phenyl | H | COOH |
| 22 | 4-CH₃O-phenyl | H | CONHOH |

TABLE 16-continued
(I-16a)
| No. | A | R⁴ | R² |
|---|---|---|---|
| 23 |  |  | COOH |
| 24 |  |  | CONHOH |
| 25 |  |  | COOH |
| 26 |  |  | CONHOH |
| 27 |  |  | COOH |
| 28 |  |  | CONHOH |
| 29 |  |  | COOH |
| 30 |  |  | CONHOH |
| 31 |  | H | COOH |
| 32 | 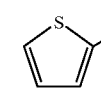 | H | CONHOH |
| 33 | 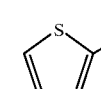 | 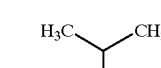 | COOH |
| 34 | 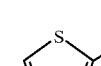 | 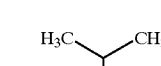 | CONHOH |
| 35 | 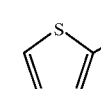 | 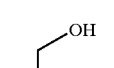 | COOH |
| 36 | 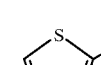 | 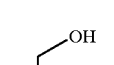 | CONHOH |
| 37 | 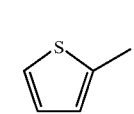 | 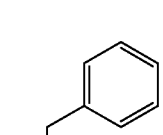 | COOH |
| 38 | 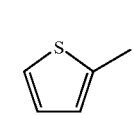 | 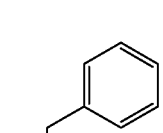 | CONHOH |
| 39 | 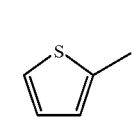 | 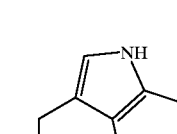 | COOH |
| 40 | 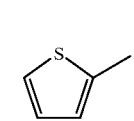 | 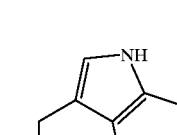 | CONHOH |

TABLE 17

(I-17a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | isopropyl (H₃C-CH-CH₃) | COOH |
| 4 | $C_5H_{11}-$ | isopropyl (H₃C-CH-CH₃) | CONHOH |
| 5 | $C_5H_{11}-$ | -CH₂-OH | COOH |
| 6 | $C_5H_{11}-$ | -CH₂-OH | CONHOH |
| 7 | $C_5H_{11}-$ | benzyl | COOH |
| 8 | $C_5H_{11}-$ | benzyl | CONHOH |
| 9 | $C_5H_{11}-$ | 3-indolylmethyl | COOH |
| 10 | $C_5H_{11}-$ | 3-indolylmethyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | -CH₂-OH | COOH |
| 16 | phenyl | -CH₂-OH | CONHOH |
| 17 | phenyl | benzyl | COOH |
| 18 | phenyl | benzyl | CONHOH |
| 19 | phenyl | 3-indolylmethyl | COOH |
| 20 | phenyl | 3-indolylmethyl | CONHOH |
| 21 | 4-methoxyphenyl ($H_3CO-C_6H_4-$) | H | COOH |
| 22 | 4-methoxyphenyl ($H_3CO-C_6H_4-$) | H | CONHOH |

TABLE 17-continued (I-17a)

Structure: A-C(=O)-CH2-[phenyl]-S(=O)-CH2-CH(R4)(R2)

| No. | A | R⁴ | R² |
|---|---|---|---|
| 23 | H₃CO-C₆H₄- | -CH(CH₃)₂ | COOH |
| 24 | H₃CO-C₆H₄- | -CH(CH₃)₂ | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 18

(I-18a)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isobutyl (H₃C-CH-CH₃) | COOH |
| 4 | C₅H₁₁— | isobutyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | -CH₂-C₆H₅ | COOH |
| 8 | C₅H₁₁— | -CH₂-C₆H₅ | CONHOH |
| 9 | C₅H₁₁— | -CH₂-(3-indolyl) | COOH |
| 10 | C₅H₁₁— | -CH₂-(3-indolyl) | CONHOH |
| 11 | C₆H₅— | H | COOH |
| 12 | C₆H₅— | H | CONHOH |
| 13 | C₆H₅— | isobutyl (H₃C-CH-CH₃) | COOH |
| 14 | C₆H₅— | isobutyl (H₃C-CH-CH₃) | CONHOH |
| 15 | C₆H₅— | -CH₂CH₂OH | COOH |
| 16 | C₆H₅— | -CH₂CH₂OH | CONHOH |
| 17 | C₆H₅— | -CH₂-C₆H₅ | COOH |
| 18 | C₆H₅— | -CH₂-C₆H₅ | CONHOH |
| 19 | C₆H₅— | -CH₂-(3-indolyl) | COOH |
| 20 | C₆H₅— | -CH₂-(3-indolyl) | CONHOH |
| 21 | 4-H₃CO-C₆H₄— | H | COOH |
| 22 | 4-H₃CO-C₆H₄— | H | CONHOH |

TABLE 18-continued (I-18a)

[Structure: A-C(=O)-CH2-C6H4-S(=O)2-CH2-CH(R4)(R2)]

| No. | A | R⁴ | R² |
|---|---|---|---|
| 23 | H3CO-C6H4- | isopropyl (H3C-CH-CH3) | COOH |
| 24 | H3CO-C6H4- | isopropyl (H3C-CH-CH3) | CONHOH |
| 25 | H3CO-C6H4- | -CH2CH2OH | COOH |
| 26 | H3CO-C6H4- | -CH2CH2OH | CONHOH |
| 27 | H3CO-C6H4- | -CH2-C6H5 | COOH |
| 28 | H3CO-C6H4- | -CH2-C6H5 | CONHOH |
| 29 | H3CO-C6H4- | -CH2-(3-indolyl) | COOH |
| 30 | H3CO-C6H4- | -CH2-(3-indolyl) | CONHOH |
| 31 | 2-thienyl | H | COOH |
| 32 | 2-thienyl | H | CONHOH |
| 33 | 2-thienyl | isopropyl (H3C-CH-CH3) | COOH |
| 34 | 2-thienyl | isopropyl (H3C-CH-CH3) | CONHOH |
| 35 | 2-thienyl | -CH2CH2OH | COOH |
| 36 | 2-thienyl | -CH2CH2OH | CONHOH |
| 37 | 2-thienyl | -CH2-C6H5 | COOH |
| 38 | 2-thienyl | -CH2-C6H5 | CONHOH |
| 39 | 2-thienyl | -CH2-(3-indolyl) | COOH |
| 40 | 2-thienyl | -CH2-(3-indolyl) | CONHOH |

TABLE 19

(I-19a)

| No. | A | R⁴ | R² |
|---|---|---|---|
| 1 | C5H11— | H | COOH |
| 2 | C5H11— | H | CONHOH |

TABLE 19-continued (I-19a)

| No. | A | R⁴ | R² |
|---|---|---|---|
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | CH₂CH₂OH | COOH |
| 6 | C₅H₁₁— | CH₂CH₂OH | CONHOH |
| 7 | C₅H₁₁— | benzyl | COOH |
| 8 | C₅H₁₁— | benzyl | CONHOH |
| 9 | C₅H₁₁— | 1H-indol-3-ylmethyl | COOH |
| 10 | C₅H₁₁— | 1H-indol-3-ylmethyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | CH₂CH₂OH | COOH |
| 16 | phenyl | CH₂CH₂OH | CONHOH |
| 17 | phenyl | benzyl | COOH |
| 18 | phenyl | benzyl | CONHOH |
| 19 | phenyl | 1H-indol-3-ylmethyl | COOH |
| 20 | phenyl | 1H-indol-3-ylmethyl | CONHOH |
| 21 | 4-methoxyphenyl (H₃CO-C₆H₄-) | H | COOH |
| 22 | 4-methoxyphenyl (H₃CO-C₆H₄-) | H | CONHOH |

TABLE 19-continued (I-19a)

[Structure: A-CH2-CH2-(p-C6H4)-S-CH2-CH(R4)-R2]

| No. | A | R⁴ | R² |
|---|---|---|---|
| 23 | H₃CO-C₆H₄- | -CH(CH₃)₂ | COOH |
| 24 | H₃CO-C₆H₄- | -CH(CH₃)₂ | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl- | H | COOH |
| 32 | 2-thienyl- | H | CONHOH |
| 33 | 2-thienyl- | -CH(CH₃)₂ | COOH |
| 34 | 2-thienyl- | -CH(CH₃)₂ | CONHOH |
| 35 | 2-thienyl- | -CH₂OH | COOH |
| 36 | 2-thienyl- | -CH₂OH | CONHOH |
| 37 | 2-thienyl- | -CH₂-C₆H₅ | COOH |
| 38 | 2-thienyl- | -CH₂-C₆H₅ | CONHOH |
| 39 | 2-thienyl- | -CH₂-(3-indolyl) | COOH |
| 40 | 2-thienyl- | -CH₂-(3-indolyl) | CONHOH |

TABLE 20

(I-20a)

Structure: A-CH₂CH₂-(p-C₆H₄)-S(=O)-CH₂-CH(R⁴)(R²)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | isobutyl (CH(CH₃)₂ via CH₂) | COOH |
| 4 | $C_5H_{11}-$ | isobutyl | CONHOH |
| 5 | $C_5H_{11}-$ | -CH₂OH | COOH |
| 6 | $C_5H_{11}-$ | -CH₂OH | CONHOH |
| 7 | $C_5H_{11}-$ | -CH₂-C₆H₅ | COOH |
| 8 | $C_5H_{11}-$ | -CH₂-C₆H₅ | CONHOH |
| 9 | $C_5H_{11}-$ | -CH₂-(1H-indol-3-yl) | COOH |
| 10 | $C_5H_{11}-$ | -CH₂-(1H-indol-3-yl) | CONHOH |
| 11 | C₆H₅- | H | COOH |
| 12 | C₆H₅- | H | CONHOH |
| 13 | C₆H₅- | isobutyl | COOH |
| 14 | C₆H₅- | isobutyl | CONHOH |
| 15 | C₆H₅- | -CH₂OH | COOH |
| 16 | C₆H₅- | -CH₂OH | CONHOH |
| 17 | C₆H₅- | -CH₂-C₆H₅ | COOH |
| 18 | C₆H₅- | -CH₂-C₆H₅ | CONHOH |
| 19 | C₆H₅- | -CH₂-(1H-indol-3-yl) | COOH |
| 20 | C₆H₅- | -CH₂-(1H-indol-3-yl) | CONHOH |
| 21 | 4-CH₃O-C₆H₄- | H | COOH |
| 22 | 4-CH₃O-C₆H₄- | H | CONHOH |

TABLE 20-continued (I-20a)

Structure: A-CH₂CH₂-C₆H₄-S(=O)-CH₂-CH(R⁴)(R²)

| No. | A | R⁴ | R² |
|---|---|---|---|
| 23 | H₃CO-C₆H₄- | -CH(CH₃)₂ | COOH |
| 24 | H₃CO-C₆H₄- | -CH(CH₃)₂ | CONHOH |
| 25 | H₃CO-C₆H₄- | -CH₂OH | COOH |
| 26 | H₃CO-C₆H₄- | -CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | -CH₂-(3-indolyl) | COOH |
| 30 | H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 21

(I-21a)

Structure: A-CH₂CH₂-C₆H₄-S(=O)₂-CH₂-CH(R⁴)(R²)

| No. | A | R⁴ | R² |
|---|---|---|---|
| 1 | C₅H₁₁— | H | COOH |
| 2 | C₅H₁₁— | H | CONHOH |

TABLE 21-continued (I-21a)

Structure: A-CH2CH2-C6H4-SO2-CH2-CH(R4)(R2)

| No. | A | R⁴ | R² |
|-----|---|-----|-----|
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | benzyl | COOH |
| 8 | C₅H₁₁— | benzyl | CONHOH |
| 9 | C₅H₁₁— | (1H-indol-3-yl)methyl | COOH |
| 10 | C₅H₁₁— | (1H-indol-3-yl)methyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | -CH₂CH₂OH | COOH |
| 16 | phenyl | -CH₂CH₂OH | CONHOH |
| 17 | phenyl | benzyl | COOH |
| 18 | phenyl | benzyl | CONHOH |
| 19 | phenyl | (1H-indol-3-yl)methyl | COOH |
| 20 | phenyl | (1H-indol-3-yl)methyl | CONHOH |
| 21 | 4-methoxyphenyl | H | COOH |
| 22 | 4-methoxyphenyl | H | CONHOH |

TABLE 21-continued (I-21a)

| No. | A | R⁴ | R² |
|---|---|---|---|
| 23 | 4-H₃CO-C₆H₄- | isopropyl (H₃C-CH-CH₃) | COOH |
| 24 | 4-H₃CO-C₆H₄- | isopropyl (H₃C-CH-CH₃) | CONHOH |
| 25 | 4-H₃CO-C₆H₄- | -CH₂CH₂OH | COOH |
| 26 | 4-H₃CO-C₆H₄- | -CH₂CH₂OH | CONHOH |
| 27 | 4-H₃CO-C₆H₄- | benzyl | COOH |
| 28 | 4-H₃CO-C₆H₄- | benzyl | CONHOH |
| 29 | 4-H₃CO-C₆H₄- | indol-3-ylmethyl | COOH |
| 30 | 4-H₃CO-C₆H₄- | indol-3-ylmethyl | CONHOH |
| 31 | 2-thienyl | H | COOH |
| 32 | 2-thienyl | H | CONHOH |
| 33 | 2-thienyl | isopropyl | COOH |
| 34 | 2-thienyl | isopropyl | CONHOH |
| 35 | 2-thienyl | -CH₂CH₂OH | COOH |
| 36 | 2-thienyl | -CH₂CH₂OH | CONHOH |
| 37 | 2-thienyl | benzyl | COOH |
| 38 | 2-thienyl | benzyl | CONHOH |
| 39 | 2-thienyl | indol-3-ylmethyl | COOH |
| 40 | 2-thienyl | indol-3-ylmethyl | CONHOH |

TABLE 22

(I-22a)

[Structure: A-C≡C-C6H4-S-CH2-CH(R4)(R2)]

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | benzyl | COOH |
| 8 | C₅H₁₁— | benzyl | CONHOH |
| 9 | C₅H₁₁— | 3-(1H-indolyl)methyl | COOH |
| 10 | C₅H₁₁— | 3-(1H-indolyl)methyl | CONHOH |
| 11 | phenyl | H | COOH |
| 12 | phenyl | H | CONHOH |

TABLE 22-continued (I-22a)

| No. | A | R⁴ | R² |
|---|---|---|---|
| 13 | phenyl | isopropyl (H₃C-CH-CH₃) | COOH |
| 14 | phenyl | isopropyl (H₃C-CH-CH₃) | CONHOH |
| 15 | phenyl | -CH₂CH₂OH | COOH |
| 16 | phenyl | -CH₂CH₂OH | CONHOH |
| 17 | phenyl | benzyl | COOH |
| 18 | phenyl | benzyl | CONHOH |
| 19 | phenyl | 3-(1H-indolyl)methyl | COOH |
| 20 | phenyl | 3-(1H-indolyl)methyl | CONHOH |
| 21 | 4-H₃CO-C₆H₄— | H | COOH |
| 22 | 4-H₃CO-C₆H₄— | H | CONHOH |

TABLE 22-continued
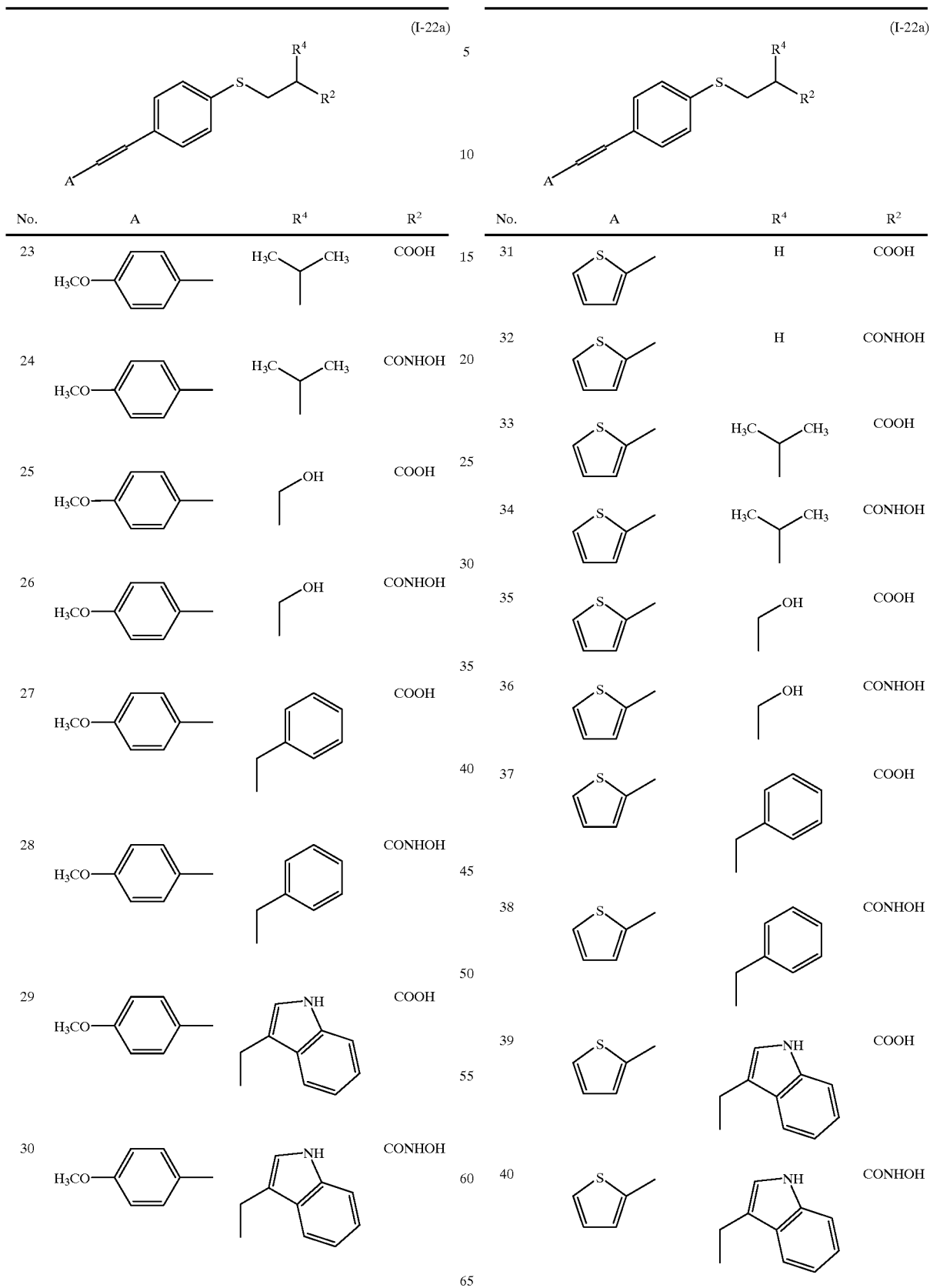

TABLE 23

(I-23a)

Structure: 4-(A-C≡C)-C6H4-S(=O)-CH2-CH(R4)(R2)

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | benzyl | COOH |
| 8 | C₅H₁₁— | benzyl | CONHOH |
| 9 | C₅H₁₁— | (1H-indol-3-yl)methyl | COOH |
| 10 | C₅H₁₁— | (1H-indol-3-yl)methyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | -CH₂CH₂OH | COOH |
| 16 | phenyl | -CH₂CH₂OH | CONHOH |
| 17 | phenyl | benzyl | COOH |
| 18 | phenyl | benzyl | CONHOH |
| 19 | phenyl | (1H-indol-3-yl)methyl | COOH |
| 20 | phenyl | (1H-indol-3-yl)methyl | CONHOH |
| 21 | 4-methoxyphenyl | H | COOH |
| 22 | 4-methoxyphenyl | H | CONHOH |

TABLE 23-continued
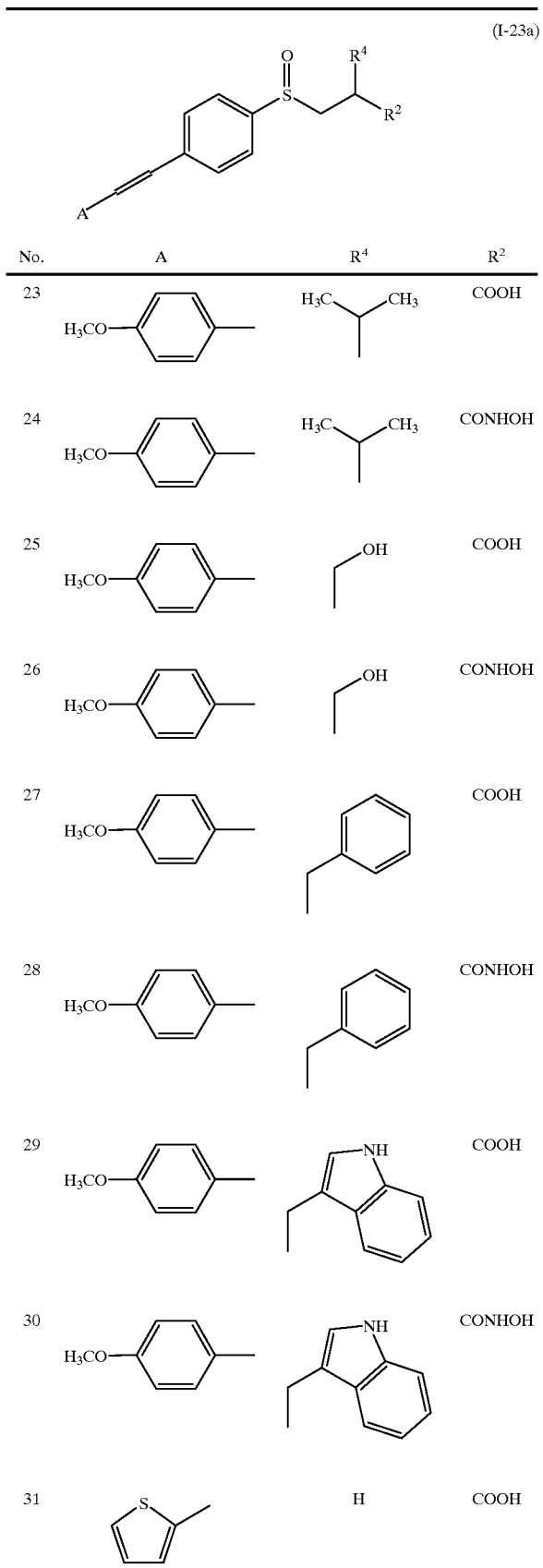
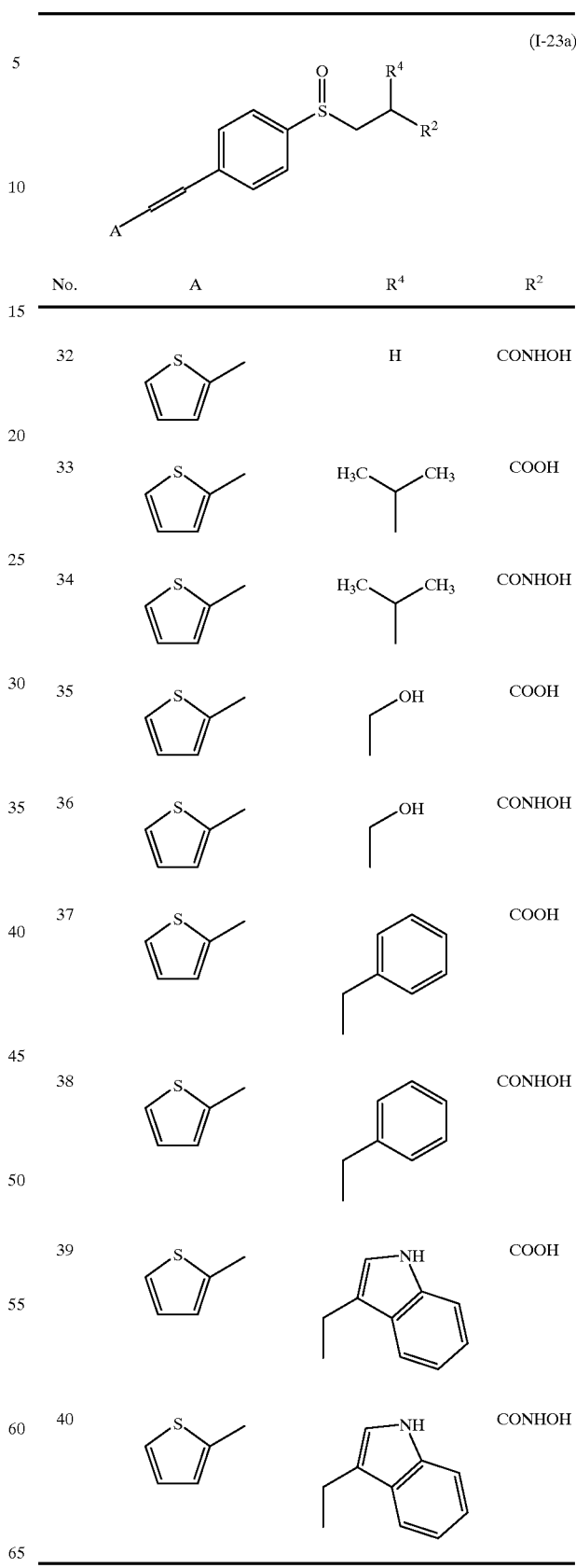

TABLE 24

(I-24a)

[Structure: 4-substituted phenyl sulfone with CH2-CH(R4)(R2) group; para position has A-C≡C- substituent]

| No. | A | R⁴ | R² |
|-----|---|-----|-----|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | -CH₂-phenyl | COOH |
| 8 | C₅H₁₁— | -CH₂-phenyl | CONHOH |
| 9 | C₅H₁₁— | -CH₂-(1H-indol-3-yl) | COOH |
| 10 | C₅H₁₁— | -CH₂-(1H-indol-3-yl) | CONHOH |
| 11 | phenyl | H | COOH |
| 12 | phenyl | H | CONHOH |

TABLE 24-continued (I-24a)

| No. | A | R⁴ | R² |
|-----|---|-----|-----|
| 13 | phenyl | isopropyl (H₃C-CH-CH₃) | COOH |
| 14 | phenyl | isopropyl (H₃C-CH-CH₃) | CONHOH |
| 15 | phenyl | -CH₂CH₂OH | COOH |
| 16 | phenyl | -CH₂CH₂OH | CONHOH |
| 17 | phenyl | -CH₂-phenyl | COOH |
| 18 | phenyl | -CH₂-phenyl | CONHOH |
| 19 | phenyl | -CH₂-(1H-indol-3-yl) | COOH |
| 20 | phenyl | -CH₂-(1H-indol-3-yl) | CONHOH |
| 21 | 4-H₃CO-phenyl | H | COOH |
| 22 | 4-H₃CO-phenyl | H | CONHOH |

TABLE 24-continued (I-24a)

Structure: A-C≡C-C₆H₄-S(O)₂-CH₂-CH(R⁴)(R²)

| No. | A | R⁴ | R² |
|---|---|---|---|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |

TABLE 25

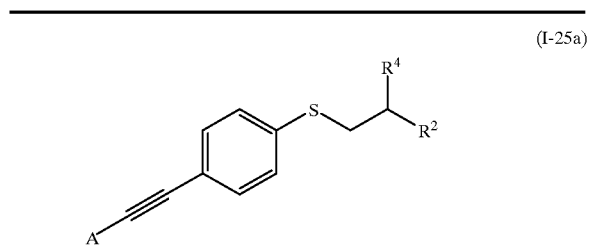

(I-25a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | H₃C  CH₃ (isopropyl) | COOH |
| 4 | $C_5H_{11}-$ | H₃C  CH₃ (isopropyl) | CONHOH |
| 5 | $C_5H_{11}-$ | -CH₂OH | COOH |
| 6 | $C_5H_{11}-$ | -CH₂OH | CONHOH |
| 7 | $C_5H_{11}-$ | -CH₂-Ph | COOH |
| 8 | $C_5H_{11}-$ | -CH₂-Ph | CONHOH |
| 9 | $C_5H_{11}-$ | -CH₂-(3-indolyl) | COOH |
| 10 | $C_5H_{11}-$ | -CH₂-(3-indolyl) | CONHOH |
| 11 | Ph- | H | COOH |

TABLE 25-continued

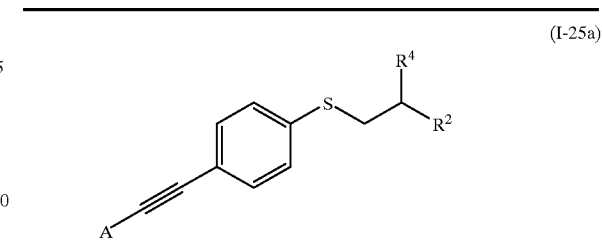

(I-25a)

| No. | A | R⁴ | R² |
|---|---|---|---|
| 12 | Ph- | H | CONHOH |
| 13 | Ph- | H₃C  CH₃ (isopropyl) | COOH |
| 14 | Ph- | H₃C  CH₃ (isopropyl) | CONHOH |
| 15 | Ph- | -CH₂OH | COOH |
| 16 | Ph- | -CH₂OH | CONHOH |
| 17 | Ph- | -CH₂-Ph | COOH |
| 18 | Ph- | -CH₂-Ph | CONHOH |
| 19 | Ph- | -CH₂-(3-indolyl) | COOH |
| 20 | Ph- | -CH₂-(3-indolyl) | CONHOH |
| 21 | $H_3CO-$Ph- | H | COOH |

TABLE 25-continued
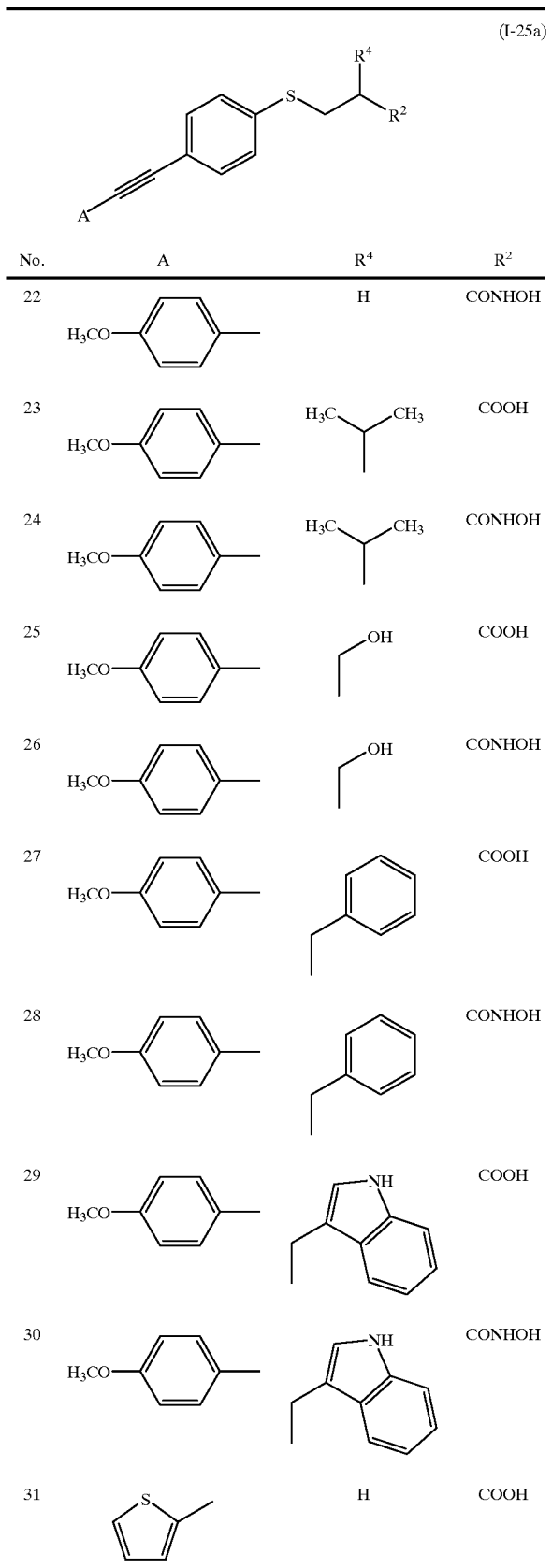
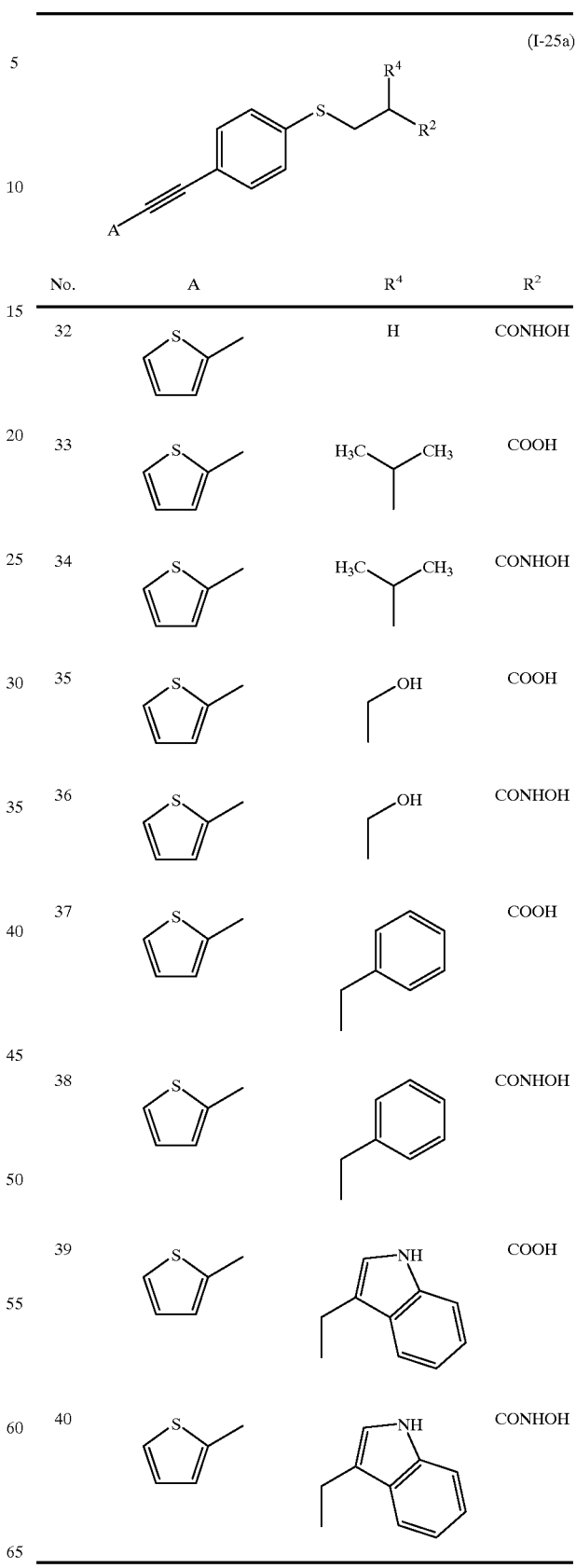

TABLE 26

(I-26a)

[Structure: A-C≡C-C6H4-S(=O)-CH2-CH(R4)(R2)]

| No. | A | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | CH₂OH | COOH |
| 6 | C₅H₁₁— | CH₂OH | CONHOH |
| 7 | C₅H₁₁— | benzyl | COOH |
| 8 | C₅H₁₁— | benzyl | CONHOH |
| 9 | C₅H₁₁— | (1H-indol-3-yl)methyl | COOH |
| 10 | C₅H₁₁— | (1H-indol-3-yl)methyl | CONHOH |
| 11 | phenyl | H | COOH |
| 12 | phenyl | H | CONHOH |
| 13 | phenyl | isopropyl | COOH |
| 14 | phenyl | isopropyl | CONHOH |
| 15 | phenyl | CH₂OH | COOH |
| 16 | phenyl | CH₂OH | CONHOH |
| 17 | phenyl | benzyl | COOH |
| 18 | phenyl | benzyl | CONHOH |
| 19 | phenyl | (1H-indol-3-yl)methyl | COOH |
| 20 | phenyl | (1H-indol-3-yl)methyl | CONHOH |
| 21 | 4-methoxyphenyl (H₃CO-C₆H₄—) | H | COOH |

TABLE 26-continued
(I-26a)
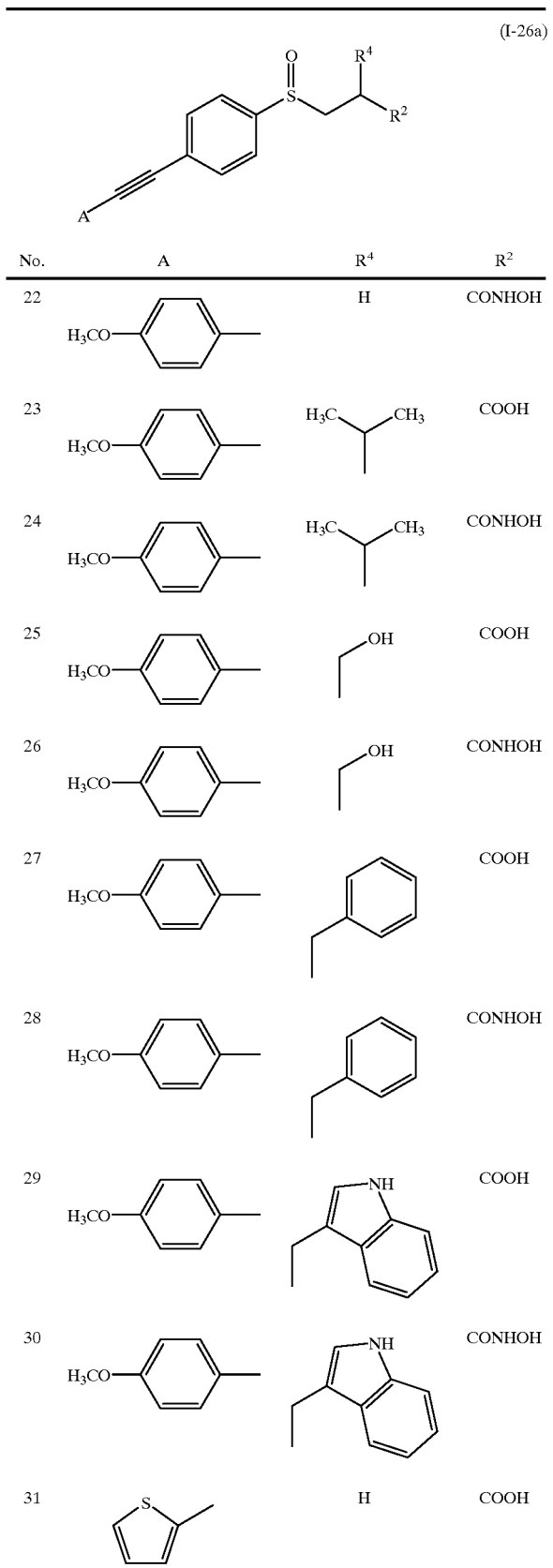
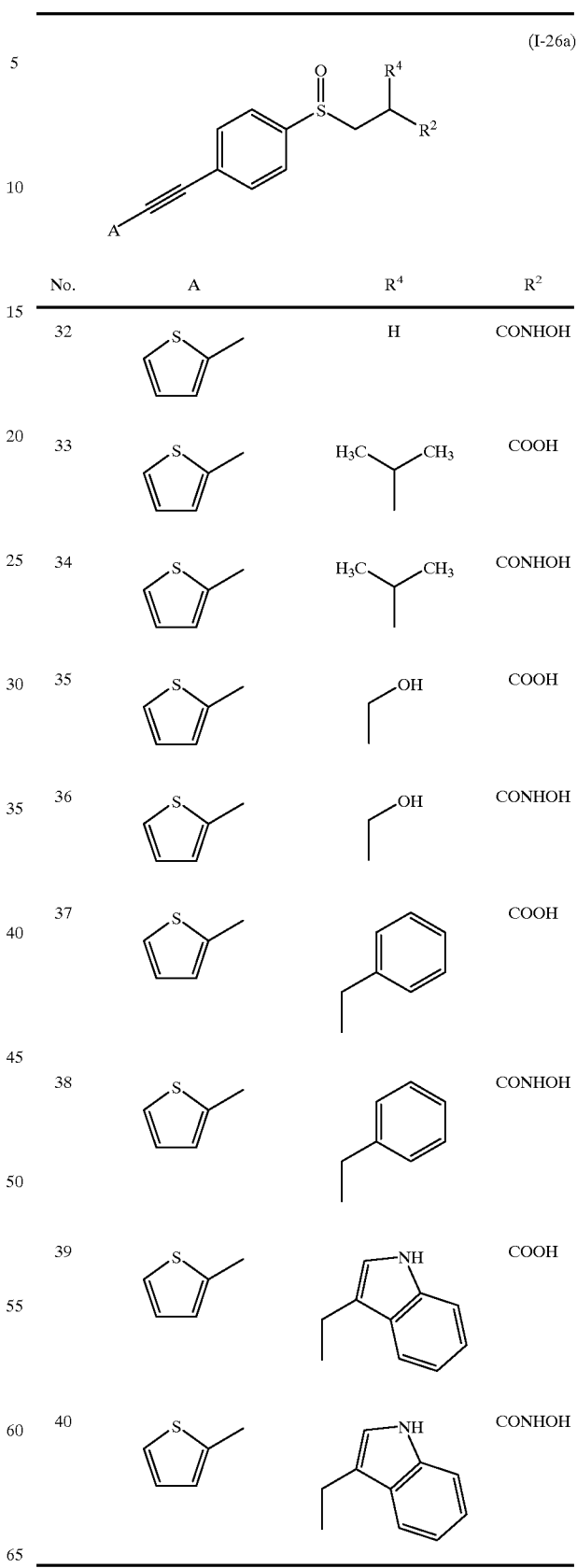

TABLE 27

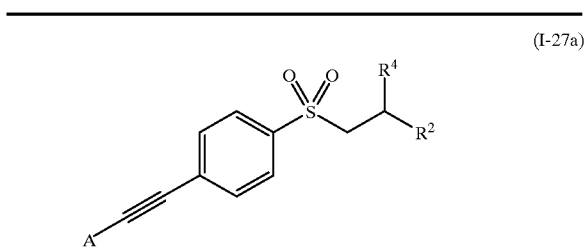

(I-27a)

| No. | A | R⁴ | R² |
|---|---|---|---|
| 1 | $C_5H_{11}-$ | H | COOH |
| 2 | $C_5H_{11}-$ | H | CONHOH |
| 3 | $C_5H_{11}-$ | $H_3C$, $CH_3$ (isopropyl) | COOH |
| 4 | $C_5H_{11}-$ | $H_3C$, $CH_3$ (isopropyl) | CONHOH |
| 5 | $C_5H_{11}-$ | –CH₂CH₂OH | COOH |
| 6 | $C_5H_{11}-$ | –CH₂CH₂OH | CONHOH |
| 7 | $C_5H_{11}-$ | –CH₂–Ph | COOH |
| 8 | $C_5H_{11}-$ | –CH₂–Ph | CONHOH |
| 9 | $C_5H_{11}-$ | –CH₂–(3-indolyl) | COOH |
| 10 | $C_5H_{11}-$ | –CH₂–(3-indolyl) | CONHOH |
| 11 | Ph– | H | COOH |

TABLE 27-continued

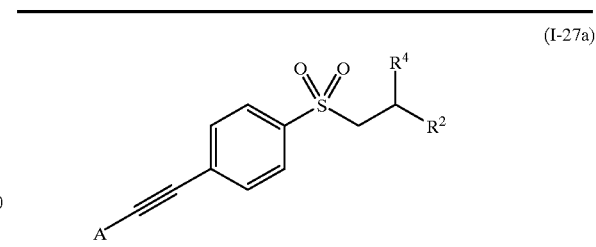

(I-27a)

| No. | A | R⁴ | R² |
|---|---|---|---|
| 12 | Ph– | H | CONHOH |
| 13 | Ph– | $H_3C$, $CH_3$ (isopropyl) | COOH |
| 14 | Ph– | $H_3C$, $CH_3$ (isopropyl) | CONHOH |
| 15 | Ph– | –CH₂CH₂OH | COOH |
| 16 | Ph– | –CH₂CH₂OH | CONHOH |
| 17 | Ph– | –CH₂–Ph | COOH |
| 18 | Ph– | –CH₂–Ph | CONHOH |
| 19 | Ph– | –CH₂–(3-indolyl) | COOH |
| 20 | Ph– | –CH₂–(3-indolyl) | CONHOH |
| 21 | 4-CH₃O–C₆H₄– | H | COOH |

TABLE 27-continued
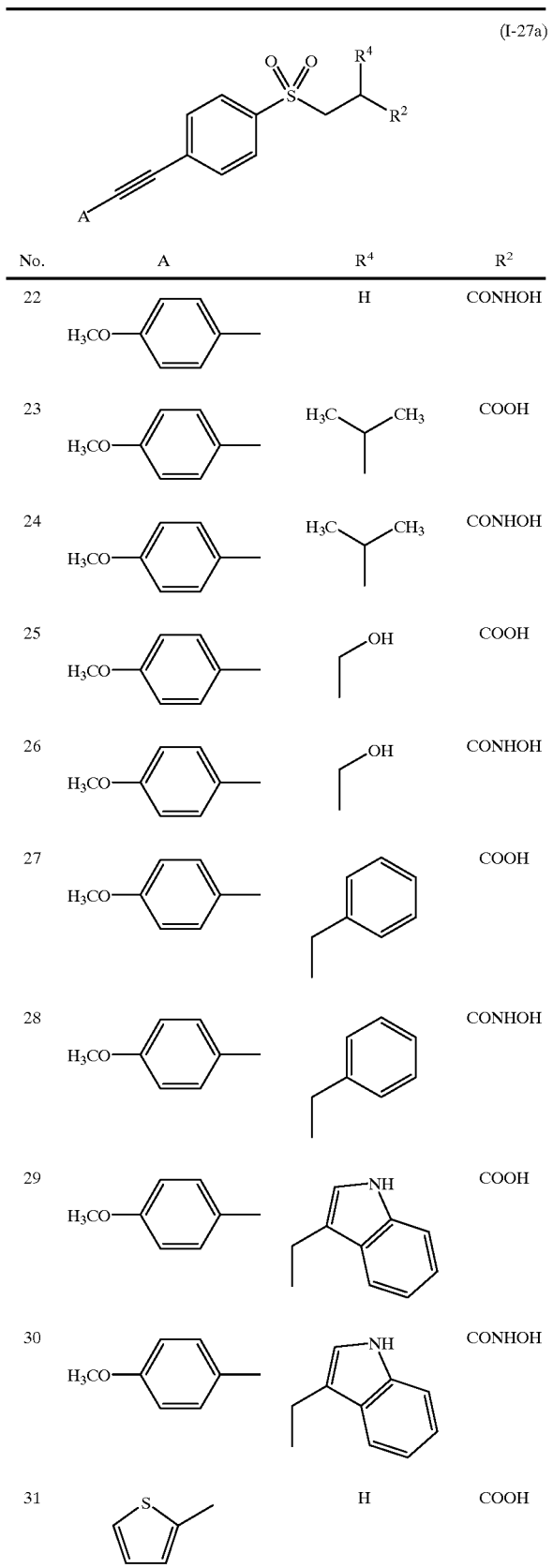
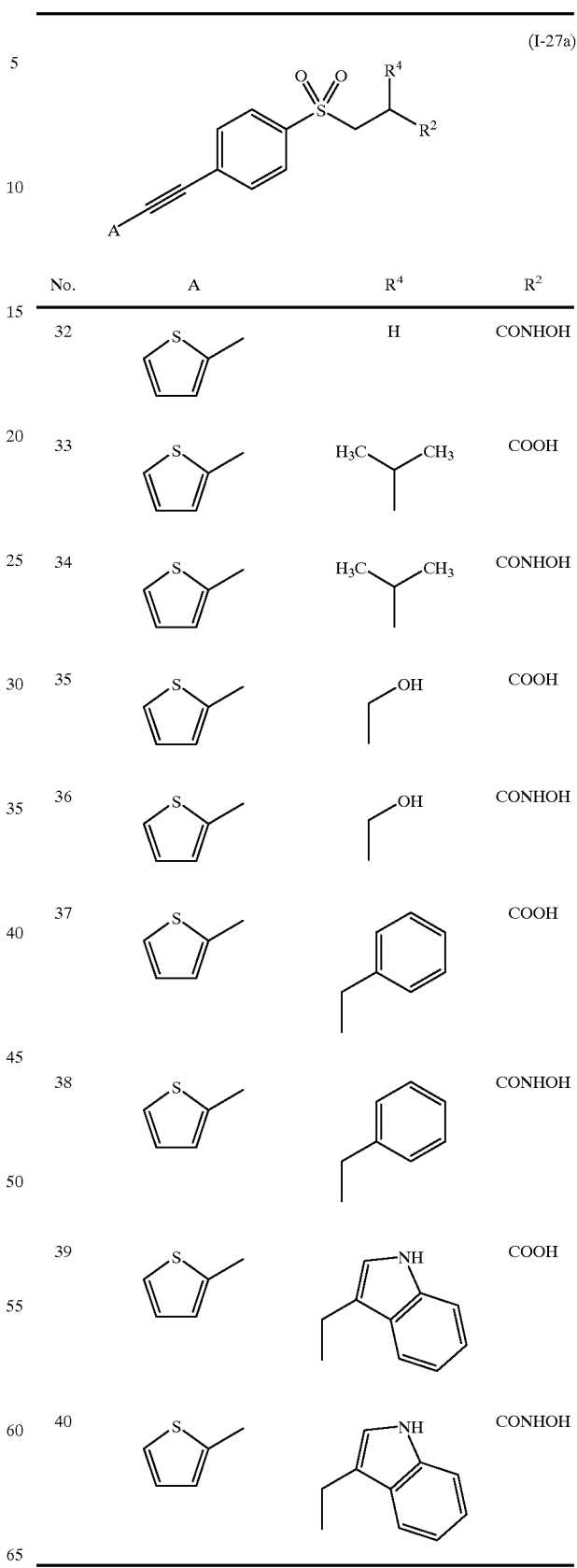

TABLE 28

(I-28a)

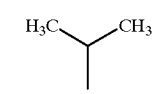

| No. | A—J—E | R⁴ | R² |
|---|---|---|---|
| 1 | $C_5H_{11}$— | H | COOH |
| 2 | $C_5H_{11}$— | H | CONHOH |
| 3 | $C_5H_{11}$— | isopropyl ($H_3C$-CH-$CH_3$) | COOH |
| 4 | $C_5H_{11}$— | isopropyl ($H_3C$-CH-$CH_3$) | CONHOH |
| 5 | $C_5H_{11}$— | -CH₂CH₂OH | COOH |
| 6 | $C_5H_{11}$— | -CH₂CH₂OH | CONHOH |
| 7 | $C_5H_{11}$— | -CH₂-phenyl | COOH |
| 8 | $C_5H_{11}$— | -CH₂-phenyl | CONHOH |
| 9 | $C_5H_{11}$— | -CH₂-(3-indolyl) | COOH |
| 10 | $C_5H_{11}$— | -CH₂-(3-indolyl) | CONHOH |
| 11 | phenyl— | H | COOH |
| 12 | phenyl— | H | CONHOH |
| 13 | phenyl— | isopropyl | COOH |
| 14 | phenyl— | isopropyl | CONHOH |
| 15 | phenyl— | -CH₂CH₂OH | COOH |
| 16 | phenyl— | -CH₂CH₂OH | CONHOH |
| 17 | phenyl— | -CH₂-phenyl | COOH |
| 18 | phenyl— | -CH₂-phenyl | CONHOH |
| 19 | phenyl— | -CH₂-(3-indolyl) | COOH |
| 20 | phenyl— | -CH₂-(3-indolyl) | CONHOH |
| 21 | 4-$H_3CO$-phenyl— | H | COOH |
| 22 | 4-$H_3CO$-phenyl— | H | CONHOH |

TABLE 28-continued
(I-28a)
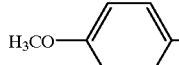
| No. | A—J—E | R⁴ | R² |
|---|---|---|---|
| 23 | 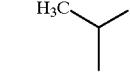 | 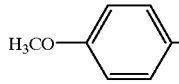 | COOH |
| 24 | 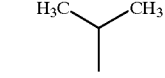 | 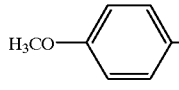 | CONHOH |
| 25 | 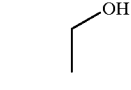 | 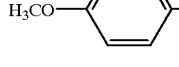 | COOH |
| 26 |  | 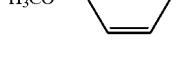 | CONHOH |
| 27 | 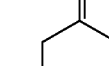 | 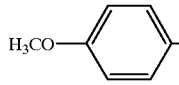 | COOH |
| 28 | 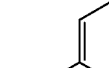 | 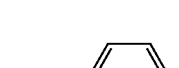 | CONHOH |
| 29 | 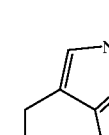 | 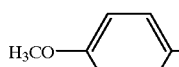 | COOH |
| 30 | 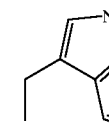 |  | CONHOH |
| 31 |  | H | COOH |
| 32 |  | H | CONHOH |
| 33 |  |  | COOH |
| 34 |  |  | CONHOH |
| 35 |  |  | COOH |
| 36 |  |  | CONHOH |
| 37 | 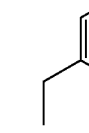 |  | COOH |
| 38 | 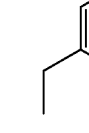 |  | CONHOH |
| 39 | 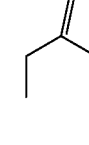 |  | COOH |
| 40 | 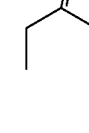 | 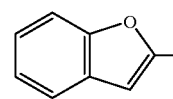 | CONHOH |
| 41 | 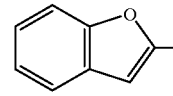 | H | COOH |
| 42 | 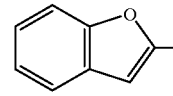 | H | CONHOH |

TABLE 28-continued (I-28a)

Structure: A—J—E—[phenyl]—S—CH2—CHR4R2

| No. | A—J—E | R4 | R2 |
|---|---|---|---|
| 43 | 2-benzofuranyl | isopropyl | COOH |
| 44 | 2-benzofuranyl | isopropyl | CONHOH |
| 45 | 2-benzofuranyl | CH2CH2OH | COOH |
| 46 | 2-benzofuranyl | CH2CH2OH | CONHOH |
| 47 | 2-benzofuranyl | benzyl | COOH |
| 48 | 2-benzofuranyl | benzyl | CONHOH |
| 49 | 2-benzofuranyl | (1H-indol-3-yl)methyl | COOH |
| 50 | 2-benzofuranyl | (1H-indol-3-yl)methyl | CONHOH |
| 51 | 5-methyl-2-benzoxazolyl | H | COOH |
| 52 | 5-methyl-2-benzoxazolyl | H | CONHOH |
| 53 | 5-methyl-2-benzoxazolyl | isopropyl | COOH |
| 54 | 5-methyl-2-benzoxazolyl | isopropyl | CONHOH |
| 55 | 5-methyl-2-benzoxazolyl | CH2CH2OH | COOH |
| 56 | 5-methyl-2-benzoxazolyl | CH2CH2OH | CONHOH |
| 57 | 5-methyl-2-benzoxazolyl | benzyl | COOH |
| 58 | 5-methyl-2-benzoxazolyl | benzyl | CONHOH |
| 59 | 5-methyl-2-benzoxazolyl | (1H-indol-3-yl)methyl | COOH |
| 60 | 5-methyl-2-benzoxazolyl | (1H-indol-3-yl)methyl | CONHOH |

TABLE 29

(I-29a)

| No. | A—J—E | R⁴ | R² |
|---|---|---|---|
| 1 | $C_5H_{11}$— | H | COOH |
| 2 | $C_5H_{11}$— | H | CONHOH |
| 3 | $C_5H_{11}$— | isobutyl | COOH |
| 4 | $C_5H_{11}$— | isobutyl | CONHOH |
| 5 | $C_5H_{11}$— | CH₂CH₂OH | COOH |
| 6 | $C_5H_{11}$— | CH₂CH₂OH | CONHOH |
| 7 | $C_5H_{11}$— | benzyl | COOH |
| 8 | $C_5H_{11}$— | benzyl | CONHOH |
| 9 | $C_5H_{11}$— | (1H-indol-3-yl)methyl | COOH |
| 10 | $C_5H_{11}$— | (1H-indol-3-yl)methyl | CONHOH |
| 11 | phenyl— | H | COOH |
| 12 | phenyl— | H | CONHOH |
| 13 | phenyl— | isobutyl | COOH |
| 14 | phenyl— | isobutyl | CONHOH |
| 15 | phenyl— | CH₂CH₂OH | COOH |
| 16 | phenyl— | CH₂CH₂OH | CONHOH |
| 17 | phenyl— | benzyl | COOH |
| 18 | phenyl— | benzyl | CONHOH |
| 19 | phenyl— | (1H-indol-3-yl)methyl | COOH |
| 20 | phenyl— | (1H-indol-3-yl)methyl | CONHOH |
| 21 | 4-H₃CO-phenyl— | H | COOH |
| 22 | 4-H₃CO-phenyl— | H | CONHOH |

TABLE 29-continued (I-29a)

| No. | A—J—E | R⁴ | R² |
|---|---|---|---|
| 23 | H₃CO-C₆H₄- | -CH(CH₃)₂ (isobutyl) | COOH |
| 24 | H₃CO-C₆H₄- | -CH(CH₃)₂ | CONHOH |
| 25 | H₃CO-C₆H₄- | -CH₂CH₂OH | COOH |
| 26 | H₃CO-C₆H₄- | -CH₂CH₂OH | CONHOH |
| 27 | H₃CO-C₆H₄- | -CH₂-C₆H₅ | COOH |
| 28 | H₃CO-C₆H₄- | -CH₂-C₆H₅ | CONHOH |
| 29 | H₃CO-C₆H₄- | 3-indolylmethyl | COOH |
| 30 | H₃CO-C₆H₄- | 3-indolylmethyl | CONHOH |
| 31 | 2-thienyl | H | COOH |
| 32 | 2-thienyl | H | CONHOH |

TABLE 29-continued (I-29a)

| No. | A—J—E | R⁴ | R² |
|---|---|---|---|
| 33 | 2-thienyl | -CH(CH₃)₂ | COOH |
| 34 | 2-thienyl | -CH(CH₃)₂ | CONHOH |
| 35 | 2-thienyl | -CH₂CH₂OH | COOH |
| 36 | 2-thienyl | -CH₂CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | 3-indolylmethyl | COOH |
| 40 | 2-thienyl | 3-indolylmethyl | CONHOH |
| 41 | 2-benzofuranyl | H | COOH |
| 42 | 2-benzofuranyl | H | CONHOH |

TABLE 29-continued (I-29a)

| No. | A—J—E | R⁴ | R² |
|---|---|---|---|
| 43 | 2-benzofuranyl | H₃C-CH(CH₃)- (isobutyl) | COOH |
| 44 | 2-benzofuranyl | H₃C-CH(CH₃)- (isobutyl) | CONHOH |
| 45 | 2-benzofuranyl | -CH₂CH₂OH | COOH |
| 46 | 2-benzofuranyl | -CH₂CH₂OH | CONHOH |
| 47 | 2-benzofuranyl | benzyl | COOH |
| 48 | 2-benzofuranyl | benzyl | CONHOH |
| 49 | 2-benzofuranyl | 3-indolylmethyl | COOH |
| 50 | 2-benzofuranyl | 3-indolylmethyl | CONHOH |
| 51 | 5-methyl-2-benzoxazolyl | H | COOH |
| 52 | 5-methyl-2-benzoxazolyl | H | CONHOH |
| 53 | 5-methyl-2-benzoxazolyl | H₃C-CH(CH₃)- (isobutyl) | COOH |
| 54 | 5-methyl-2-benzoxazolyl | H₃C-CH(CH₃)- (isobutyl) | CONHOH |
| 55 | 5-methyl-2-benzoxazolyl | -CH₂CH₂OH | COOH |
| 56 | 5-methyl-2-benzoxazolyl | -CH₂CH₂OH | CONHOH |
| 57 | 5-methyl-2-benzoxazolyl | benzyl | COOH |
| 58 | 5-methyl-2-benzoxazolyl | benzyl | CONHOH |
| 59 | 5-methyl-2-benzoxazolyl | 3-indolylmethyl | COOH |
| 60 | 5-methyl-2-benzoxazolyl | 3-indolylmethyl | CONHOH |

TABLE 30

(I-30a)

Structure: A—J—E—[phenyl]—S(O)₂—CH₂—CH(R⁴)(R²)

| No. | A—J—E | R⁴ | R² |
|---|---|---|---|
| 1 | C₅H₁₁— | H | COOH |
| 2 | C₅H₁₁— | H | CONHOH |
| 3 | C₅H₁₁— | isopropyl (H₃C-CH-CH₃) | COOH |
| 4 | C₅H₁₁— | isopropyl (H₃C-CH-CH₃) | CONHOH |
| 5 | C₅H₁₁— | -CH₂CH₂OH | COOH |
| 6 | C₅H₁₁— | -CH₂CH₂OH | CONHOH |
| 7 | C₅H₁₁— | -CH₂-C₆H₅ (benzyl) | COOH |
| 8 | C₅H₁₁— | -CH₂-C₆H₅ (benzyl) | CONHOH |
| 9 | C₅H₁₁— | -CH₂-(3-indolyl) | COOH |
| 10 | C₅H₁₁— | -CH₂-(3-indolyl) | CONHOH |
| 11 | phenyl— | H | COOH |
| 12 | phenyl— | H | CONHOH |
| 13 | phenyl— | isopropyl (H₃C-CH-CH₃) | COOH |
| 14 | phenyl— | isopropyl (H₃C-CH-CH₃) | CONHOH |
| 15 | phenyl— | -CH₂CH₂OH | COOH |
| 16 | phenyl— | -CH₂CH₂OH | CONHOH |
| 17 | phenyl— | -CH₂-C₆H₅ (benzyl) | COOH |
| 18 | phenyl— | -CH₂-C₆H₅ (benzyl) | CONHOH |
| 19 | phenyl— | -CH₂-(3-indolyl) | COOH |
| 20 | phenyl— | -CH₂-(3-indolyl) | CONHOH |
| 21 | H₃CO—phenyl— | H | COOH |
| 22 | H₃CO—phenyl— | H | CONHOH |

TABLE 30-continued (I-30a)

Structure: A—J—E—[phenyl]—S(=O)₂—CH₂—CH(R⁴)(R²)

| No. | A—J—E | R⁴ | R² |
|-----|-------|-----|-----|
| 23 | 4-H₃CO-C₆H₄- | -CH(CH₃)₂ | COOH |
| 24 | 4-H₃CO-C₆H₄- | -CH(CH₃)₂ | CONHOH |
| 25 | 4-H₃CO-C₆H₄- | -CH₂OH | COOH |
| 26 | 4-H₃CO-C₆H₄- | -CH₂OH | CONHOH |
| 27 | 4-H₃CO-C₆H₄- | -CH₂-C₆H₅ | COOH |
| 28 | 4-H₃CO-C₆H₄- | -CH₂-C₆H₅ | CONHOH |
| 29 | 4-H₃CO-C₆H₄- | -CH₂-(3-indolyl) | COOH |
| 30 | 4-H₃CO-C₆H₄- | -CH₂-(3-indolyl) | CONHOH |
| 31 | 2-thienyl | H | COOH |
| 32 | 2-thienyl | H | CONHOH |
| 33 | 2-thienyl | -CH(CH₃)₂ | COOH |
| 34 | 2-thienyl | -CH(CH₃)₂ | CONHOH |
| 35 | 2-thienyl | -CH₂OH | COOH |
| 36 | 2-thienyl | -CH₂OH | CONHOH |
| 37 | 2-thienyl | -CH₂-C₆H₅ | COOH |
| 38 | 2-thienyl | -CH₂-C₆H₅ | CONHOH |
| 39 | 2-thienyl | -CH₂-(3-indolyl) | COOH |
| 40 | 2-thienyl | -CH₂-(3-indolyl) | CONHOH |
| 41 | 2-benzofuranyl | H | COOH |
| 42 | 2-benzofuranyl | H | CONHOH |

TABLE 30-continued (I-30a)

| No. | A—J—E | R⁴ | R² |
|---|---|---|---|
| 43 | 2-benzofuranyl | isopropyl (H₃C, CH₃) | COOH |
| 44 | 2-benzofuranyl | isopropyl (H₃C, CH₃) | CONHOH |
| 45 | 2-benzofuranyl | -CH₂CH₂OH | COOH |
| 46 | 2-benzofuranyl | -CH₂CH₂OH | CONHOH |
| 47 | 2-benzofuranyl | benzyl (-CH₂-C₆H₅) | COOH |
| 48 | 2-benzofuranyl | benzyl (-CH₂-C₆H₅) | CONHOH |
| 49 | 2-benzofuranyl | 3-indolylmethyl | COOH |
| 50 | 2-benzofuranyl | 3-indolylmethyl | CONHOH |
| 51 | 5-methylbenzoxazol-2-yl | H | COOH |
| 52 | 5-methylbenzoxazol-2-yl | H | CONHOH |
| 53 | 5-methylbenzoxazol-2-yl | isopropyl (H₃C, CH₃) | COOH |
| 54 | 5-methylbenzoxazol-2-yl | isopropyl (H₃C, CH₃) | CONHOH |
| 55 | 5-methylbenzoxazol-2-yl | -CH₂CH₂OH | COOH |
| 56 | 5-methylbenzoxazol-2-yl | -CH₂CH₂OH | CONHOH |
| 57 | 5-methylbenzoxazol-2-yl | benzyl | COOH |
| 58 | 5-methylbenzoxazol-2-yl | benzyl | CONHOH |
| 59 | 5-methylbenzoxazol-2-yl | 3-indolylmethyl | COOH |
| 60 | 5-methylbenzoxazol-2-yl | 3-indolylmethyl | CONHOH |

[Processes for the Preparation of the compound of the present invention]

The compounds of the present invention of the formula (I) may be prepared by the following methods, the methods described in Example, or known methods.

In the compounds of the present invention of the formula (I), (A-1):the compound in which n is 0, $R^2$ is —COOR$^{7-1}$ (in which $R^{7-1}$ is C1-8 alkyl, phenyl, or C1-4 alkyl substituted by phenyl, —OCOR$^{23}$ or —CONR$^{24}$R$^{25}$), substituents of Ar in A, and $R^3$ and $R^4$ are not —COOH, hydroxy, amino or a group containing them, and A, J and E taken together do not represent —COOH, i.e., the compound of the formula (I-A-1)

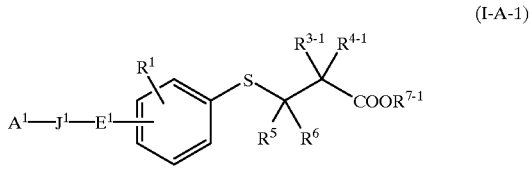

(wherein $R^{3-1}$ and $R^{4-1}$ are the same meanings as $R^3$ and $R^4$ respectively, with the proviso that $R^{3-1}$ and $R^{4-1}$ do not represent —COOH, hydroxy, amino or a group containing them; and $A^1$, $J^1$ and $E^1$ are the same meanings as A, J and E respectively, with the proviso that substituents of Ar in A are not —COOH, hydroxy or amino and A, J and E taken together do not represent —COOH, and the other symbols are the same meanings as hereinbefore described.) may be prepared by the following methods.

(1) The compound in which $E^1$ is —CONR⁹—, may be prepared by amidation of the compound of the formula (II)

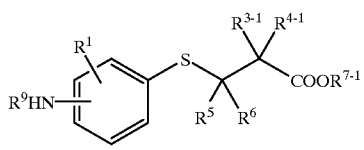

(wherein all the symbols are the same meanings as hereinbefore described.)
with the compound of the formula (III)

$A^1—J^1—COOH$ (III)

(wherein all the symbols are the same meanings as hereinbefore described.).

The method of amidation is known. It is includes the method
(1) via an acid halide,
(2) via a mixed acid anhydride,
(3) using a condensing agent etc.

These methods are explained as follows.
(1) The method via an acid halide may be carried out, for example, by reacting a carboxylic acid with an acid halide (e. g., oxalyl chloride, thionyl chloride etc.) in an organic solvent (e.g., chloroform, methylene chloride, diethyl ether, tetrahydrofuran etc.) or without a solvent at from −20° C. to the reflux temperature, and then by reacting the obtained acid halide with an amine in the presence of a tertiary amine (e. g., pyridine, triethylamine, dimethylaniline, dimethylaminopyridine etc.) in an organic solvent (e. g., chloroform, methylene chloride, diethyl ether, tetrahydrofuran etc.) at a temperature of from 0° C. to 40° C.
(2) The method via a mixed acid anhydride may be carried out, for example, by reacting a carboxylic acid with an acid halide (e. g., pivaloyl chloride, tosyl chloride, mesyl chloride, ethyl chloroformate, isobutyl chloroformate etc.) in the presence of a tertiary amine (e. g., pyridine, triethylamine, dimethylaniline, dimethylaminopyridine etc.) in an organic solvent (e. g., chloroform, methylene chloride, diethyl ether, tetrahydrofuran etc.) or without a solvent at a temperature of from −20° C. to 40° C., and then by reacting the obtained mixture of acid anhydride with a corresponding amine in an organic solvent (e. g., chloroform, methylene chloride, diethyl ether, tetrahydrofuran etc.), at a temperature of from 0° C. to 40° C.

(3) The method using a condensing agent (e. g., 1,3-dicyclohexylcarbodiimide (DCC), 1-ethyl-3-[3-(dimethylamino)propyl] carbodiimide (EDC), 2-chloro-1-methylpyridinium iodide etc.) may be carried out, for example, by reacting a carboxylic acid with an amine using a condensing agent in the presence or absence of a tertiary amine (e. g., pyridine, triethylamine, dimethylaniline, dimethylaminopyridine etc.), in an organic solvent (e. g., chloroform, methylene chloride, dimethyl formamide, diethyl ether etc.) or without a solvent at a temperature of from 0° C. to 40° C.

The reactions (1), (2) and (3) hereinbefore described may be preferably carried out in an atmosphere of inert gas (e. g., argon, nitrogen etc.) under anhydrous conditions.

(2) The compound in which $E^1$ is —NR⁹CO, may be prepared by amidation of the compound of formula (IV)

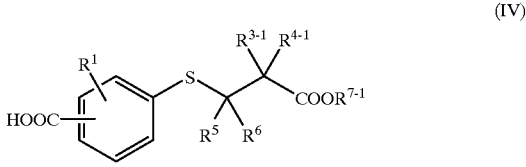

(wherein all the symbols are the same meanings as hereinbefore described.) with the compound of the formula (V)

$A^1—J^1—NHR^9$ (V)

(wherein all the symbols are the same meanings as hereinbefore described.).

The amidation may be carried out by methods hereinbefore described.

(3) The compound in which $E^1$ is —OCO, may be prepared by esterification of the compound of the formula (IV)

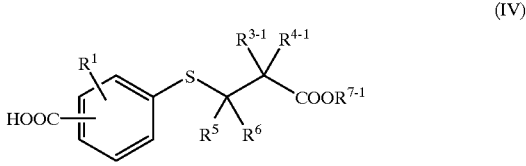

(wherein all the symbols are the same meanings as hereinbefore described.) with the compound of the formula (VI)

$A^1—J^1—OH$ (VI)

(wherein all the symbols are the same meanings as hereinbefore described.)

The method of esterification is known. It is includes the method
(1) via an acid halide,
(2) via a mixed acid anhydride,
(3) using a condensing agent etc.

These methods are explained as follows.
(1) The method via an acid halide may be carried out, for example, by reacting a carboxylic acid with an acid halide (e. g., oxalyl chloride, thionyl chloride etc.) in an organic solvent (e.g., chloroform, methylene chloride, diethyl ether, tetrahydrofuran etc.) or without a solvent at from −20° C. to the reflux temperature, and then by reacting the obtained acid halide with an alcohol in the presence of a tertiary amine (e. g., pyridine, triethylamine, dimethylaniline, dimethylaminopyridine etc.) in an organic solvent (e. g., chloroform, methylene chloride, diethyl ether, tetrahydrofuran etc.) at a temperature of from 0° C. to 40° C.

(2) The method via a mixed acid anhydride may be carried out, for example, by reacting a carboxylic acid with an acid halide (e. g., pivaloyl chloride, tosyl chloride, mesyl chloride etc.) or an acid derivative (e. g., ethyl chloroformate, isobutyl chloroformate etc.) in the presence of a tertiary amine (e. g., pyridine, triethylamine, dimethylaniline, dimethylaminopyridine etc.) in an organic solvent (e. g., chloroform, methylene chloride, diethyl ether, tetrahydrofuran etc.) or without a solvent at a temperature of from 0° C. to 40° C., and then by reacting the obtained mixture of acid anhydride with an alcohol in an organic solvent (e. g., chloroform, methylene chloride, diethyl ether, tetrahydroturan etc.), at a temperature of from 0° C. to 40° C.

(3) The method using a condensing agent (e. g., 1,3-dicyclohexylcarbodiimide (DCC), 1-ethyl-3-[3-(dimethylamino)propyl] carbodiimide (EDC), 2-chloro-1-methylpyridinium iodide etc.) may be carried out, for example, by reacting a carboxylic acid with an alcohol using a condensing agent in the presence or absence of a tertiary amine (e. g., pyridine, triethylamine, dimethylaniline, dimethylaminopyridine etc.), in an organic solvent (e. g., chloroform, methylene chloride, dimethyl formamide, diethyl ether etc.) or without a solvent at a temperature of from 0° C. to 40° C.

The reactions (1), (2) and (3) hereinbefore described may be preferably carried out in an atmosphere of inert gas (e. g., argon, nitrogen etc.) under anhydrous conditions.

(4) The compound in which $E^1$ is —COO—, may be prepared by esterification of the compound of the formula (VII)

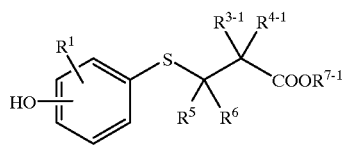

(VII)

(wherein all the symbols are the same meanings as hereinbefore described.) with the compound of the formula (III)

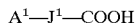

(III)

(wherein all the symbols are the same meanings as hereinbefore described.).

The esterification may be carried out by methods hereinbefore described.

(5) The compound in which $E^1$ is —CH$_2$—O—, may be prepared by etherification of the compound of the formula (VII)

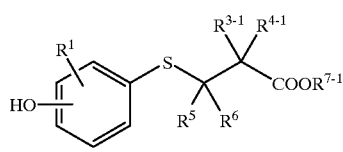

(VII)

(wherein all the symbols are the same meanings as hereinbefore described.) with the compound of the formula (VIII)

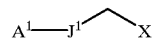

(VIII)

(wherein X is halogen or trifluoromethanesulfonyloxy, the other symbols are the same meanings as hereinbefore described.). The etherification is known and may be carded out, for example, in an organic solvent (e.g., dimethylformamide, acetone etc.), in the presence of base (e.g., potassium carbonate etc.), at a temperature of from 0° C. to 40° C.

(6) The compound in which $E^1$ is —CO—CH$_2$—, —(CH$_2$)$_2$—, —CH=CH— or —C≡C—, or in which $A^1$, $J^1$ and $E^1$ taken together represents heterocyclic ring (this heterocyclic ring may be substituted by 1–4 of C1-4 alkyl, C1-4 alkoxy, halogen, trifluoromethyl, hydroxy, carboxyl, C1-8 alkoxycarbonyl, nitro, NR$^{24}$R$^{25}$ (in which R$^{24}$ and R$^{25}$ are the same meanings as hereinbefore described.) or CONR$^{24}$R$^{25}$ (in which R$^{24}$ and R$^{25}$ are the same meanings as hereinbefore described.)), may be prepared by reduction of the compound of the formula (AA)

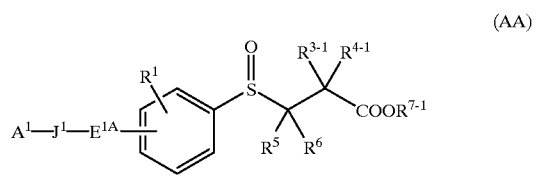

(AA)

(wherein $E^{1A}$ is —CO—CH$_2$—, —(CH$_2$)$_2$—, —CH=CH— or —C≡C—, or $A^1$, $J^1$ and $E^{1A}$ taken together represents heterocyclic ring (this heterocyclic ring may be substituted by 1–4 of C1-4 alkyl, C1-4 alkoxy, halogen, trifluoromethyl, hydroxy, carboxyl, C1-8 alkoxycarbonyl, nitro, NR$^{24}$R$^{25}$ (in which R$^{24}$ and R$^{25}$ are the same meanings as hereinbefore described.) or CONR$^{24}$R$^{25}$ (in which R$^{24}$ and R$^{25}$ are the same meanings as hereinbefore described.), the other symbols are the same meanings as hereinbefore described.).

The reduction is known and may be carried out, for example, using a hydrogen donor (e.g., triethylsilane, trichlorosilane etc.) in an organic solvent (e.g., trifluoroacetic acid etc.) at a temperature of from 0° C. to 40° C., or this reaction may be also carried out by hydrogenolysis hereinafter described.

(7) The compound in which $A^1$, $J^1$ and $E^1$ taken together represents methyl, halogen, trifluoromethyl, nitro, cyano, formyl, phenyl, hydroxy, NR$^{16}$R$^{17}$, may be prepared by the reaction of the compound of the formula (IX)

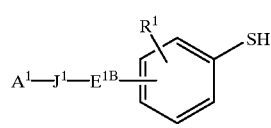

(IX)

(wherein $A^1$, $J^1$ and E1B taken together represents methyl, halogen, trifluoromethyl, nitro, cyano, formyl, phenyl, hydroxy, NR$^{16}$R$^{17}$ (in which R$^{16}$ and R$^{17}$ are the same meanings as hereinbefore described.), the other symbols are the same meanings as hereinbefore described.) with the compound of the formula (XA), formula (XB), formula (XC) or formula (XD)

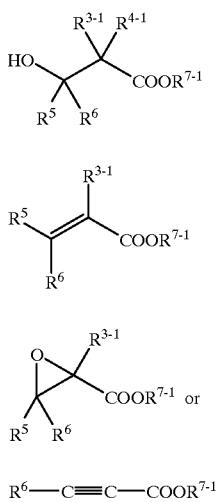

(XA)

(XB)

(XC)

(XD)

$R^6$—C≡C—COOR$^{7\text{-}1}$ (wherein all the symbols are the same meanings as hereinbefore described.).

This reaction is known and may be carried out, for example, in an organic solvent (e.g., diisopropylethylamine, tetrahydrofuran, ethanol, chloroform, acetonitrile etc.) in the presence of base catalyst (e.g., triethylamine, tetrabutylammonium fluoride, morpholine, n-butyllithium etc.), at a temperature of from 0° C. to 40° C.

(A-2): the compound in which n is 1 or 2, $R^2$ is —COOR$^{7\text{-}1}$ (in which $R^{7\text{-}1}$ is the same meaning as hereinbefore described.), substituents of Ar in A, and $R^3$ and $R^4$ are not —COOH, hydroxy, amino or a group containing them, A, J and E taken together do not represent —COOH, i.e., the compound of the formula (I-A-2)

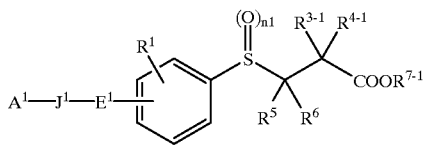

(I-A-2)

(wherein n1 is 1 or 2, all the other symbols are the same meanings as hereinbefore described.) may be prepared by the following methods.

(1) The compound in which n$^1$ is 1 or 2, $E^1$ is —CONR$^9$—, —NR$^9$CO—, —OCO—, —COO—, —CH$_2$—O—, and A$^1$, J$^1$ and E$^1$ taken together do not represent —COOH, may be prepared by oxidation of the compound of the formula (I-A-1a)

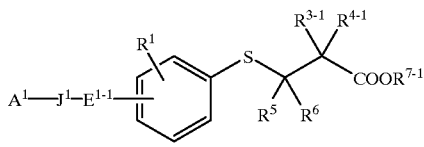

(I-A-1a)

(wherein $E^{1\text{-}1}$ is —CONR$^9$—, —NR$^9$CO—, —OCO—, —COO—, —CH$_2$—O—, or A, J$^1$ and E$^{1\text{-}1}$ taken together represents methyl, halogen, trifluoromethyl, nitro, cyano, formyl, phenyl, hydroxy, NR$^{16}$R$^{17}$ (in which R$^{16}$ and R$^{17}$ are the same meanings as hereinbefore described.), the other symbols are the same meanings as hereinbefore described.).

The oxidation is known and may be carried out, for example, in an organic solvent (e.g., methylene chloride, chloroform etc.) in the presence of peracid (e.g., m-chloroperbenzoic acid etc.) at a temperature of from 0° C. to 40° C.; or using oxidizing agent (e.g., periodic acid·2 hydrate etc.) in a solvent (carbon tetrachloride, acetonitrile, water, ethanol or mixture solvent thereof etc.), in the presence or absence of catalyst (e.g., ruthenium (III) chloride hydrate etc.) at a temperature of from 0° C. to reflux temperature.

(2) The compound in which ni is 1 or 2, $E^1$ is —C≡—C—, or A, J and E taken together represents heterocyclic ring (this heterocyclic ring may be substituted by 1–4 of C1-4 alkyl, C1-4 alkoxy, halogen, trifluoromethyl, hydroxy, carboxyl, C1-8 alkoxycarbonyl, nitro, NR$^{24}$R$^{25}$ (in which R$^{24}$ and R$^{25}$ are the same meanings as hereinbefore described.) or CONR$^{24}$R$^{25}$ (in which R$^{24}$ and R$^{25}$ are the same meanings as hereinbefore described.)), may be prepared by reaction of the compound of the formula (XI)

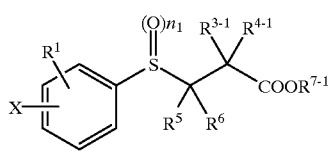

(XI)

(wherein all the symbols are the same meanings as hereinbefore described.) with the compound of the formula (XII)

A$^1$—J$^1$—≡ (XII)

(wherein all the symbols are the same meanings as hereinbefore described.) or the corresponding heterocyclic ring compound.

This reaction is known and may be carried out, for example, using a catalyst (e.g., tetrakis(triphenylphosphine) palladium etc.) in an organic solvent (e.g., acetonitrile, tetrahydrofuran etc.) in the presence of base (e.g., triethylamine etc.) and copper(I) iodide, at a temperature of from 0° C. to reflux temperature.

(3) The compound in which n1 is 2, $E^1$ is —CO—CH$_2$—, may be prepared by reaction of the compound of the formula (XIII)

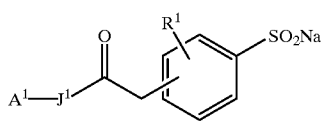

(XIII)

(wherein all the symbols are the same meanings as hereinbefore described.) with the compound of the formula (XA), formula (XB), formula (XC) or formula (XD)

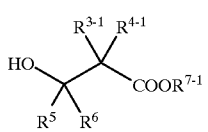

(XA)

-continued

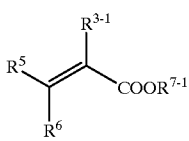
(XB)

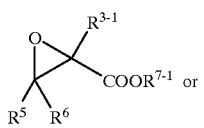
(XC)

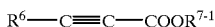
(XD)

(wherein all the symbols are the same meanings ass hereinbefore described.); or may be prepared by treating the compound prepared in above (2) with trifluoroacetic acid.

This reaction is known and may be carried out, for example, by refluxing with heating, in an organic solvent (e.g., ethanol, mixture solvent of water and benzene etc.), in the presence of acetic acid or poly ethylene glycol.

(4) The compound in which n1 is 2, En is —CH=CH—, may be prepared by dehydration of the compound of the formula (XIV)

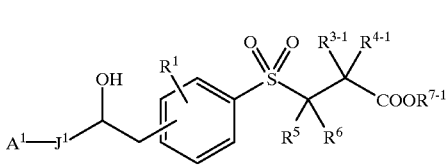
(XIV)

(wherein all the symbols are the same meanings as hereinbefore described.).

The dehydration is known and may be carried out, for example, by refluxing with heating, in an organic solvent (erg., toluene, benzene etc.), in the presence of catalytic quantity of p-toluenesulfonic acid.

(5) The compound in which n1 is 2, $E^1$ is —$(CH_2)_2$—, may be prepared by reduction of the compound of the formula (XIV)

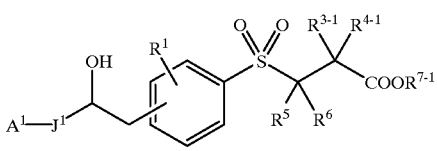
(XIV)

(wherein all the symbols are the same meanings as hereinbefore described.).

The reduction may be carried out by method as hereinbefore described, or this reaction may be carried out by hydrogenolysis as hereinafter described. (6) The compound in which n1 is 1, $E^1$ is —CO—$CH_2$—, —$(CH_2)_2$—, —CH=CH—, may be prepared by reduction of the compound (n1 is 2, and $E^1$ is —CO—$CH_2$—, —$(CH_2)_2$—, —CH=CH—.) prepared in above (3)–(5).

The reduction may be carried out by method as hereinbefore described, or this reaction may be carried out by hydrogenolysis as hereinafter described.

The compound in which n1 is 1, $E^1$ is —CO—$CH_2$—, may be prepared by treating the compound (wherein n is 1, $E^1$ is —C≡C—.) prepared in above (2) with trifluoroacetic acid.

(7) In the compounds hereinbefore prepared in (1)–(6), the compound in which $R^{3-1}$ is hydrogen, $R^{4-1}$ is

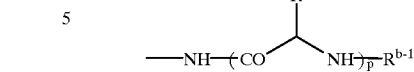

(in which $R^{b-1}$ is —$COOR^{22}$ or —$COR^{22}$ (in which $R^{22}$ is the same meaning as hereinbefore described.), the other symbols are the same meanings as hereinbefore described.), may be prepared by amidation of the formula (BB)

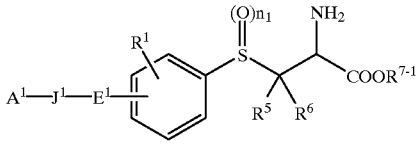
(BB)

(wherein all the symbols are the same meanings as hereinbefore described.) with the corresponding carboxylic acid of the formula (CC)

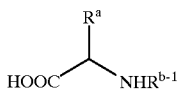
(CC)

(wherein all the symbols are the same meanings as hereinbefore described.).

If necessary, it may be prepared by amidation of the corresponding carboxylic acid of the formula (CC) with the compound obtained by deprotection of protecting group ($R^{b-1}$) of amino under acidic condition of compound prepared in above reaction.

The amidation may be carried out by methods as hereinbefore described. The deprotection of protecting group of amino under acidic condition may be carried out by methods as hereinafter described.

(B) The compounds in which at least one of —$COOR^7$ in $R^2$, and $R^3$, $R^4$, and substituents of Ar in A, and a group represented by A, J and E taken together, represents —COOH or a group containing —COOH; or at least one of $R^3$, $R^4$, and substituents of Ar in A, represents hydroxy, amino or a group containing them, i.e., the compounds of the formula (I-B)

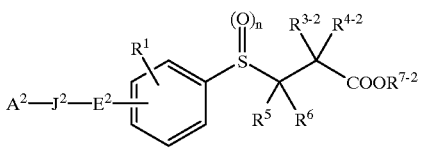
(I-B)

(wherein $A^2$, $J^2$, $E^2$, $R^{3-2}$, $R^{4-2,}$ $R^{7-2}$ are the same meanings as A, J, E, $R^3$, $R^4$, $R^7$ respectively, with proviso that at least one of —$COOR^7$, and $R^3$, $R^4$, and substituents of Ar in A, and a group represented by A, J and E taken together, represents —COOH or a group containing them; or at least one of $R^3$, $R^4$, and substituents of Ar in A, represents hydroxy, amino or a group containing them; the other symbols are the same meanings as hereinbefore described.) may be prepared by deprotection under alkaline or acidic conditions, or hydrogenolysis of the compound of the formula (I-A-1) and the formula (I-A-2).

Deprotection under alkaline conditions is known and may be carried out, for example, in an organic solvent (e.g., methanol, tetrahydrofuran, dioxane etc.), using an alkali metal hydroxide (e.g., sodium hydroxide, potassium hydroxide etc.), an alkali earth metal hydroxide (e.g., calcium hydroxide etc.) or a carbonate (e.g., sodium carbonate, potassium carbonate etc.), an aqueous solution thereof or a mixture thereof, at a temperature of from 0° C. to 40° C.

Deprotection under acidic conditions is known and may be carried out, for example, in a solvent (e.g., dichloro methane, dioxane, ethyl acetate, acetic acid water or a mixture solvent thereof etc.), using an organic acid (e.g., trifluoroacetic acid etc.) or an inorganic acid (e.g., hydrogen chloride, hydrogen bromide etc.) at a temperature of from 0° C. to 120° C.

Hydrogenolysis is known and may be carried out, for example, in a solvent (e.g., ether (e.g., tetrahydrofuran, dioxane, diemethoxyethane, diethyl ether etc.), alcohol (e.g., methanol, ethanol etc.), a benzene-type solvent (e.g., benzene, toluene etc.), ketone (etc. acetone, methylethylketone etc.), nitorile (acetonitrile etc.), amide (dimethylformamide etc.), water, ethyl acetate, acetic acid or a mixture of two or more thereof, in the presence of a catalyst (e.g., palladium on carbon, palladium black, palladium hydroxide, platinum dioxide, Raney-nickel etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonic acid, oxalic acid, trifluoroacetic acid, formic acid etc.), at ordinary or elevated pressure of hydrogen gas or ammonium formate at a temperature of from 0° C. to 200° C.

(C) The compounds, in which $R^2$ is —CONHOR$^{8-1}$ (in which $R^{8-1}$ is C1-8 alkyl, phenyl, or C1-4 alkyl substituted by phenyl.); substituents of Ar in A, $R^3$ and $R^4$ do not represent —COOH, hydroxy, amino or a group containing them; A, J and E taken together do not represent —COOH, i.e., the compounds of the formula (I-C)

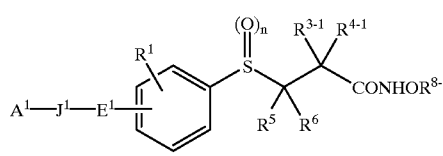
(I-C)

(wherein all the symbols are the same meanings as hereinbefore described.) may be prepared by the following methods.

(1) The compound in which n is 0, may be prepared by condensation of the compound of the formula (XV)

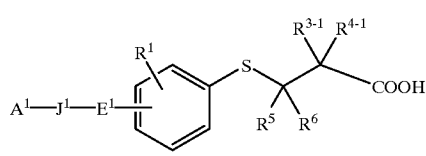
(XV)

(wherein all the symbols are the same meanings as hereinbefore described.) with the compound of formula (XVI)

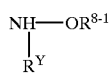
(XV)

(wherein $R^Y$ is hydrogen or protection group of amino, the other symbols are the same meanings as hereinbefore described.).

The condensation is known and may be carried out, for example, in an organic solvent (e.g., chloroform, methylene chloride, dimethylformamide, tetrahydrofuran etc.) or without a solvent, optionally using a tertiary amine (e.g., pyridine, triethylamine, dimethylaniline, dimethylaminopyridine etc.), using a condesing agent (e.g., 1-ethyl-3-[3-(dimethylamino)propyl]carbodiimide (EDC) etc.), at a temperature of from 0° C. to 40° C.

(2) The compound in which n is 1 or 2, may be prepared by oxidation of the compound of the formula (I-C-1) prepared in above (1)

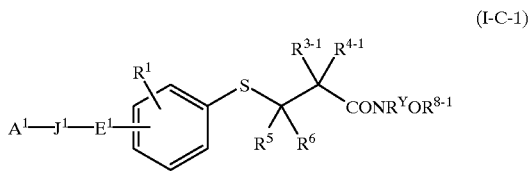
(I-C-1)

(wherein all the symbols are the same meanings as hereinbefore described.), if necessary, followed by deprotection of $R^Y$.

The oxidation may be carried out by methods as hereinbefore described.

The deprotection of $R^Y$ is known and may be carried out, for example, in a solvent (e.g., methylene chloride, dioxane, ethyl acetate, acetic acid water or a mixture solvent thereof etc.), using an organic acid (e.g., trifluoroacetic acid etc.) or an inorganic acid (e.g., hydrogen chloride, hydrogen bromide etc.) at a temperature of from 0° C. to 120° C.; or in a solvent (e.g., ether (e.g., tetrahydrofuran, dioxane, diemethoxyethane, diethyl ether etc.), alcohol (e.g., methanol, ethanol etc.), a benzene-type solvent (e.g., benzene, toluene etc.), ketone (etc. acetone, methylethylketone etc.), nitorile (acetonitrile etc.), amide (dimethyliormamide etc.), water, ethyl acetate, acetic acid or a mixture of two or more thereof), in the presence of a catalyst (e.g., palladium on carbon, palladium black, palladium hydroxide, platinum dioxide, Raney-nickel etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonic acid, oxalic acid, trifluoroacetic acid, formic acid etc.), at ordinary or elevated pressure of hydrogen gas or ammonium formate at a temperature of from 0° C. to 200° C. When an acid is used, a salt thereof may be used.

(D) The compounds in which PB in PB is hydrogen, in which at least one of $R^3$, $R^4$, and substituents of Ar in A, or a group represented by A, J and E taken together, represents —COOH or a group containing —COOH, and in which at least one of $R^3$, $R^4$, and substituents of Ar in A, represents hydroxy, amino or a group containing them, i.e., the compounds of the formula (I-D)

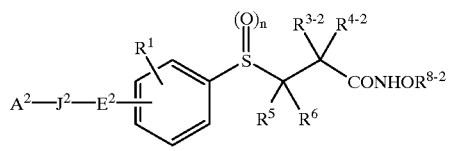

(I-D)

(wherein $A^2$, $J^2$, $E^2$, $R^{3-2}$, $R^{4-2}$, $R^{8-2}$ are the same meanings as A, J, E, $R^3$, $R^4$, $R^8$ respectively, with the proviso that at least one of $R^3$, $R^4$, substituents of Ar in A, or a group represented by A, J and E taken together, represents —COOH or a group containing —COOH; at least one of $R^3$, $R^4$, substituents of Ar in A, represents hydroxy, amino or a group containing them; or $R^8$ is hydrogen, the other symbols are the same meanings as hereinbefore described.) may be prepared by deprotection under alkali or acidic conditions, or hydrogenolysis of the compound of the formula (I-C).

The deprotection under alkali or acidic conditions, or hydrogenolysis, may be carried out by the methods as hereinbefore described.

The compounds of formulae (II), (IV), (VII), (XI) or (XIV) may be prepared by known methods, methods described in the following schemes 1, 2, 3, 4 and 5 or methods described in Example.

Scheme 1

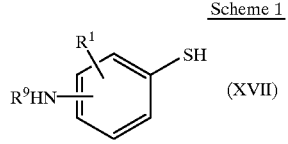

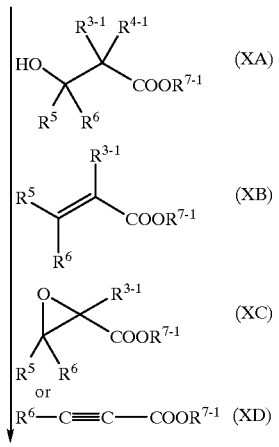

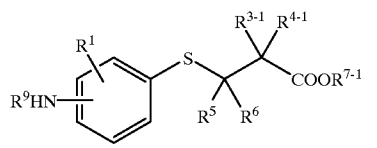

Scheme 2

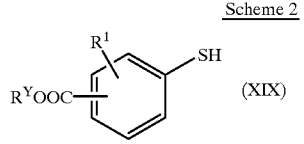

-continued

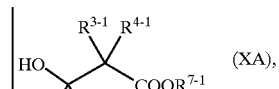

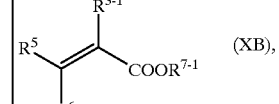

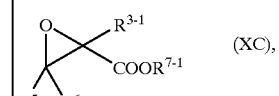

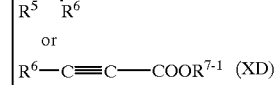

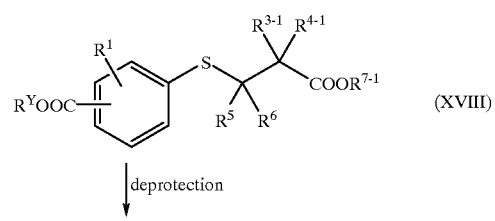

deprotection

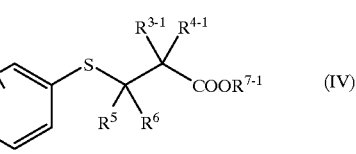

Scheme 3

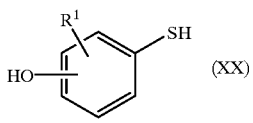

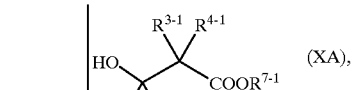

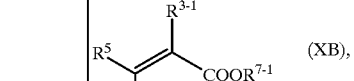

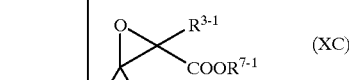

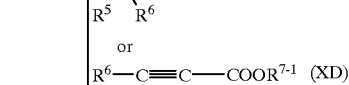

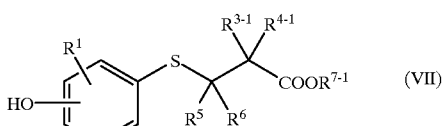

Scheme 4
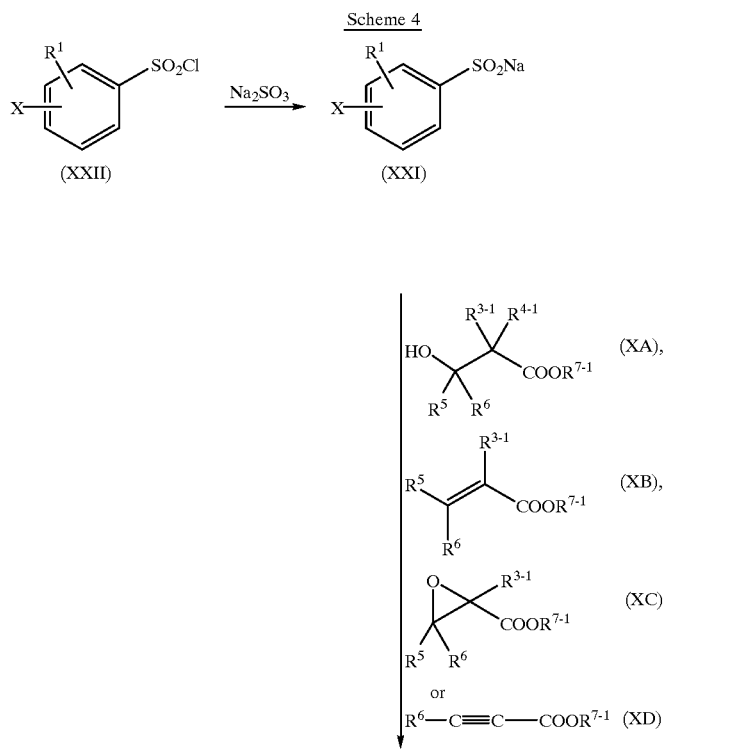
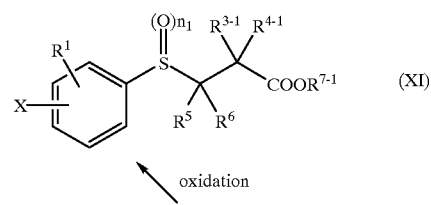
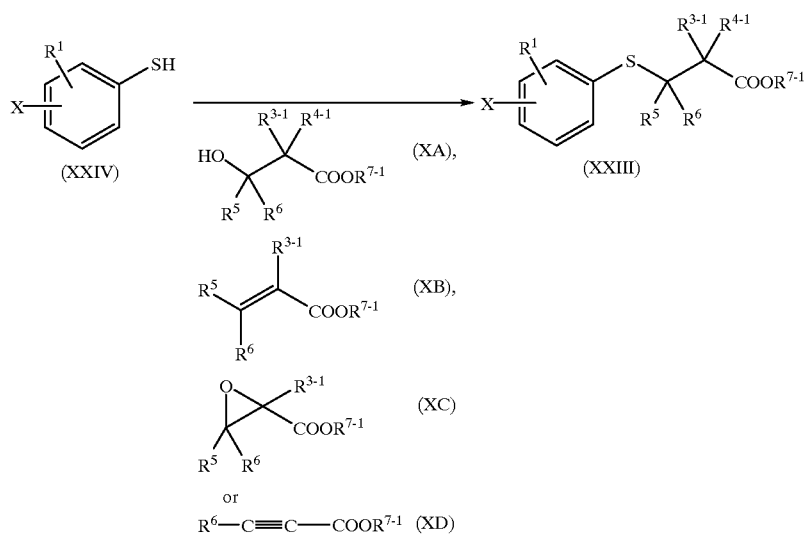

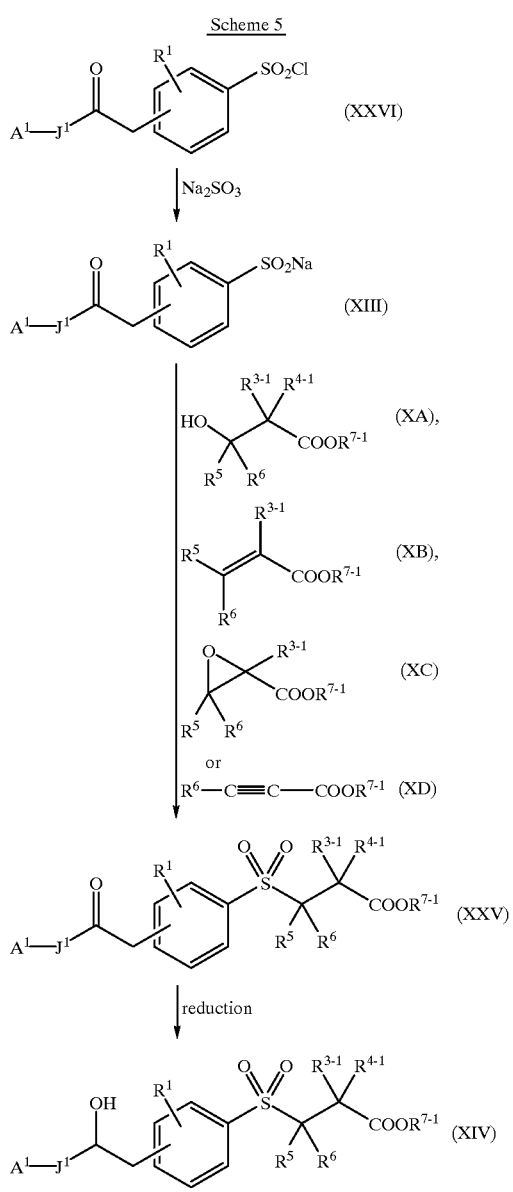

Scheme 5

In the schemes, $R^Z$ is protection group of carboxylic acid, the other symbols are the same meanings as hereinbefore described.

Each reaction in the above schemes, may be carried out by known methods. In the above schemes, the compounds used as starting materials are known per se, or may be easily prepared by known methods. The other starting materials and reagents in the present invention are known per se or may be prepared by known methods.

In each reaction in the present invention, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Possibility of Industrial use
[Pharmacological Activity]

The potency of inhibitory activity of the compounds of the formula (I) against matrix metalloproteinases is confirmed by the following experiment. For example, with respect to inhibitory activity against gelatinase A, the following results are obtained.
(1) Inhibitory activity against gelatinase A.
Experimental method The progelatinase A (7 μl; in assay buffer (90 μl) was purified from human normal skin dermal fibroblasts (HNDF). It was activated by the addition of 10 mM APMA (10 μl) for 1 hour at 37° C. The solution of activated gelatinase A (1 U/tube, 98 μl) was mixed with the solution of various concentrations of the test compound or the solution in which the test compound is not added, (2 μl), and 0.05% FITC-gelatin (100 μl) and incubated for 2 hours at 37° C. The enzymatic reaction was terminated by the addition of 2 M Tris-HCI (pH 9.5) containing 94.7% ethanol (750 el). The mixture was stirred and then allowed to stand for 30 minutes at 0° C. The mixture was centrifuged for 30 minutes at 900×g. Inhibitory activity against gelatinase was determined by measuring the fluorescent intensity in supernatant (Ex=495 nm, and Em=520 nm). The results are shown in Table 31.

TABLE 31

| Example No. | IC50 (μM) |
| --- | --- |
| 8(2) | 0.54 |
| 8(7) | 0.40 |
| 19(1) | 0.011 |
| 28 | 0.013 |
| 28(1) | 0.0014 |
| 28(3) | 0.0029 |

In the above experimental method, APMA is p-aminophenylmercuric acetate and FITC is fluorescein isothiocyanate.
[Toxicity]

On the other hand, the toxicity of the compounds of the present invention is very low and therefore it may be confirmed that the compounds are safe for pharmaceutical use.
[Application for Pharmaceuticals]

Inhibition of matrix metalloproteinases is useful for prevention and I or treatment of rheumatoid diseases, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune diseases (e.g. Crohn's disease, Sjogren's syndrome), diseases caused by vascular emigration or infiltration of leukocytes, arterialization etc.

For the purpose above described, the compounds of formula (I) of the present invention, non-toxic salts, acid addition salts or hydrates thereof may be normally by administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders, and granules.

Capsules include hard capsules and soft capsules.

In such solid compositions, one or more of the active compound(s) may be admixed with at least one inert diluent (such as lactose, mannitol, glucose, hydroxypropyl cellulose, microcrystalline cellulose, starch, polyvinylpyrrolidone or magnesium metasilicate aluminate). The compositions may also comprise, as is normal practice, additional substances other than inert diluents: e.g., lubricating agents (such as magnesium stearate), disintegrating agents (such as cellulose calcium glycolate), stabilizing agents (such as lactose), and agents to assist dissolution (such as glutamic acid or aspartic acid). The tablets or pills may, if desired, be coated with a film of gastric or enteric material (such as sugar, gelatin, hydroxypropyl cellulose or hydroxypropylmethyl cellulose phthalate), or be coated with two or more films. And further, coating may include containment within capsules of absorbable materials such as gelatin.

Liquid compositions for oral administration include pharmaceutically acceptable emulsions, solutions, syrups and elixirs. In such liquid compositions, one or more of the active compound(s) may be contained in an inert diluent(s) commonly used in the art (e.g., purified water, ethanol). Besides inert diluents, such compositions may also comprise adjuvants (such as wetting agents or suspending agents), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g., stabilizing agents (such as sodium sulfate), isotonic buffer (such as sodium chloride, sodium citrate or citric acid). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or POLYSORBATE80 (registered trade mark). Injections may comprise additional ingredients other than inert diluents: e.g. preserving agents, wetting agents, emulsifying agents, dispersing agents, stabilizing agents (such as lactose), assisting agents such as agents to assist dissolution (e.g. glutamic acid or aspartic acid). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

REFERENCE EXAMPLE AND EXAMPLE

The following reference examples and examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

Example 1

3-(4-aminophenylthio)propionic acid t-butyl ester

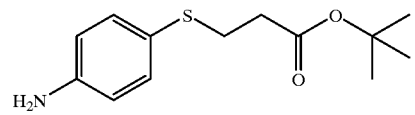

To a solution of 4-aminothiophenol (2.36 g) in tetrahydrofuran (THF; 20 ml), 2-propenoic acid t-butyl ester (3.51 ml) and 1.0M tetrabutylammonium fluoride in THF solution (340 μl) were added. The mixture solution was stirred for 30 minutes at room temperature to give the title compound. The compound was used for next reaction as such.

Example 1(1)~1(4)

The following compounds were obtained by the same procedure as Example 1, using the corresponding thiophenol derivatives and the corresponding carboxylic acid derivatives.

Example 1(1)

3-(4-hydroxyphenylthio)propionic acid t-butyl ester

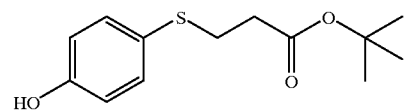

The prepared title compound was used for next reaction without purification.

Example 1(2)

2-methyl-3-(4-hydroxyphenylthio)propionic acid t-butyl ester

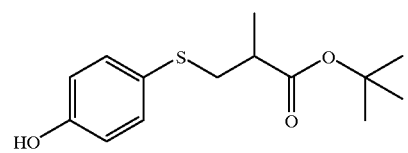

TLC: Rf 0.45 (hexane:ethyl acetate=7:3),

NMR (CDCl$_3$+CCl$_4$ (5 drops)): δ 7.31 (2H, d, J=8.8 Hz), 6.77 (2H, d, J=8.8 Hz), 55.82 (1H, s), 3.08 (1H, dd, J=1 3.2 Hz, 7.8 Hz), 2.77 (1H, dd, J=1 3.2 Hz, 6.6 Hz), 2.53 (1H, m), 1.47 (9H, s), 1.20 (3H, d, J=7.2 Hz).

Example 1(3)

2-benzyl-3-(4-bromophenylthio)propionic acid t-butyl ester

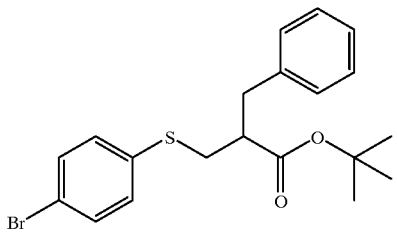

TLC: Rf 0.58 (hexane:ethyl acetate=4:1),

NMR (CDCl$_3$): δ 7.36 (2H, d, J=8.8 Hz), 7.30–7.10 (7H, m), 3.11 (1H, dd, J=14.0 Hz, 8.1 Hz), 3.00–2.70 (4H, m), 1.36 (9H, s).

Example 1(4)

3-(4-methoxyphenylthio)propionic acid t-butyl ester

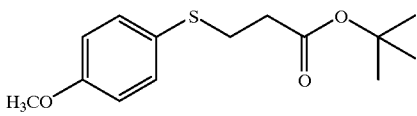

The prepared title compound was used for next reaction without purification.

Example 2

3-[4-(benzoylamino) phenylthio]propionic acid t-butyl ester

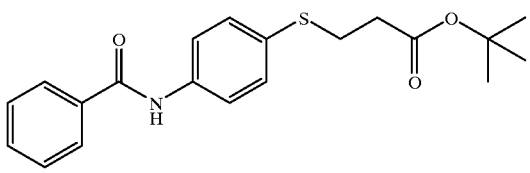

Triethylamine (3.3 ml) and benzoyl chloride (2.0 ml) were added to the compound prepared in Example 1 and the reaction solution was stirred for 30 minutes at room temperature. 1 N hydrochloric acid was added to the reaction solution. The reaction solution was extracted with ethyl acetate. The extract was washed with a saturated aqueous solution of sodium bicarbonate, water, a saturated aqueous solution of sodium chloride, dried over anhydrous magnesium sulfate and concentrated. The residue was washed with ether to give the title compound (5.17 g).

TLC: Rf 0.51 (hexane:ethyl acetate=7:3),

NMR (CDCl$_3$): δ 7.92 (1H, s), 7.89–7.82 (2H, m), 7.60 (2H, d, J=8.8 Hz), 7.56–7.42 (3H, m), 7.38 (2H, d, J=8.8 Hz), 3.08 (2H, t, J=7.4 Hz), 2.51 (2H, t, J=7.4 Hz), 1.45 (9H, s).

Example 3

3-(4-benzyloxyphenylthio)propionic acid t-butyl ester

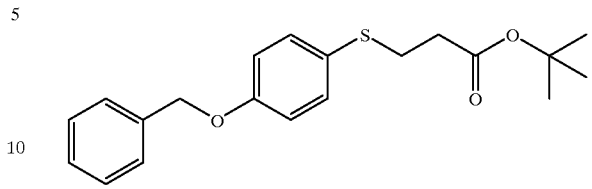

A mixture solution of the compound prepared in Example 1(1) (3.29 g), benzyl bromide (2.3 ml), potassium carbonate (3.58 g) and dimethylformamide (15 ml) was stirred overnight at room temperature. The reaction solution was extracted with ethyl acetate. The extract was washed with water and a saturated aqueous solution of sodium chloride, dried over anhydrous magnesium sulfate and concentrated to give the title compound (2.20 g) having the following physical data.

TLC: Rf 0.71 (hexane:ethyl acetate=4:1),

NMR (CDCl$_3$): δ 7.46–7.30 (7H, m), 6.90 (2H, d, J=9.0 Hz), 5.04 (2H, s), 3.00 (2H, t, J=7.6 Hz), 2.46 (2H, t, J=7.6 Hz), 1.44 (9H, s).

Example 4

3-[4-(benzoylamino)phenylsulfinyl]propionic acid t-butyl ester

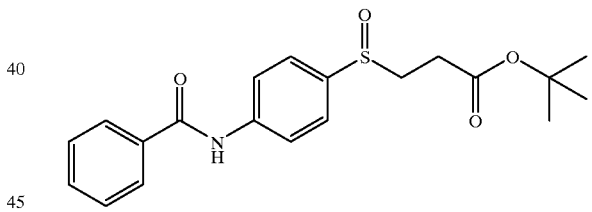

To a solution of the compound prepared in Example 2 (714 mg) in chloroform (7 ml), m-chloroperbenzoic acid (493 mg) was added and the reaction solution was stirred for 30 minutes at room temperature. The reaction solution was washed with a saturated aqueous solution of sodium bicarbonate and a saturated aqueous solution of sodium chloride, dried over anhydrous magnesium sulfate and concentrated. Ether was added to the residue and the crystal was filtered off and then the title compound (616 mg) having the following physical data was obtained.

TLC: Rf 0.37 (chloroform:methanol=19:1),

NMR (CDCl$_3$): δ 8.17 (1H, s), 7.94–7.86 (2H, m), 7.85 (2H, d., J=8.8 Hz), 7.61 (2H, d, J=8.8 Hz), 7.57–7.46 (3H, m), 3.15 (1H, ddd, J=6.6 Hz, 8.8 Hz, 13.2 Hz), 2.93 (1H, ddd, J=5.8 Hz, 8.2 Hz, 13.2 Hz), 2.73 (1H, ddd, J=6.6 Hz, 8.2 Hz, 14.4 Hz), 2.43 (1H, ddd, J=5.8 Hz, 8.8 Hz, 14.4 Hz), 1.43 (9H, s).

Example 5
3-[4-(benzoylamino)phenylsulfonyl]propionic acid t-butyl ester

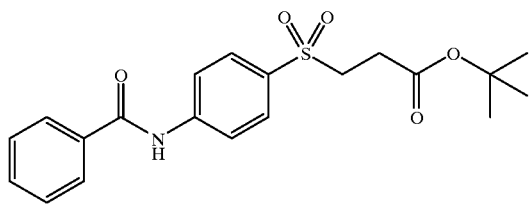

Under an atmosphere of argon, to a mixture solution of the compound prepared in Example 2 (714 mg) in carbon tetrachloride (2 ml), acetonitrile (2 ml) and water (4 ml), periodic acid·2 hydrates (958 mg) and ruthenium (III) chloride·hydrate (8 mg) were added and reaction mixture was stirred for 2 hours. Water was added to the reaction mixture and it was extracted with ethyl acetate. The extract was washed with a saturated aqueous solution of sodium thiosulfate and a saturated aqueous solution of sodium chloride, dried over anhydrous magnesium sulfate and concentrated. The residue was purified by column chromatography (hexane:ethyl acetate=3:2) to give the title compound (730 mg) having the following physical data.

TLC: Rf 0.20 (hexane:ethyl acetate=7:3),

NMR (CDCl$_3$): δ 8.11 (1H, s), 7.94–7.86 (6H, m), 7.65–7.47 (3H, m), 3.37 (2H, t, J=7.4 Hz), 2.65 (2H, t, J=7.4 Hz), 1.41 (9H,s).

Example 5(1)~5(2)

The following compounds were obtained by the same procedure as Example 5, using compounds prepared in Example 3 and Example 1(3)

Example 5(1)
3-[4-(benzyloxy)phenylsulfonyl]propionic acid t-butyl ester

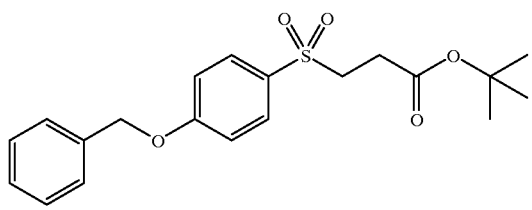

TLC: Rf 0.33 (hexane:ethyl acetate=7:3),

NMR (CDCl$_3$): δ 7.83 (2H, d, J=9.2 Hz), 7.42–7.32 (5H, m), 7.09 (2H, d, J=9.2 Hz), 5.14 (2H, s), 3.34 (2H, t, J=7.4 Hz), 2.64 (2H, t, J=7.4 Hz).

Example 5(2)
2-benzyl-3-(4-bromophenylsulfonyl)propionic acid t-butyl ester

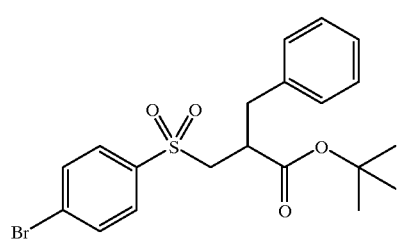

TLC: Rf 0.30 (hexane:ethyl acetate=4:1),

NMR (CDCl$_3$): δ 7.69 (2H; d, J=8.8 Hz), 7.67 (2H, d, J=8.8 Hz), 7.30–7.20 (3H, m), 7.07 (2H, s), 3.63 (1H, m), 3.10–2.90 (3H, m), 2.90 (1H, m), 1.33 (9H, s).

Reference Example 1

2-methyl-3-[4-(trifluoromethanesulfonyloxy)phenylthio]propionic acid t-butyl ester

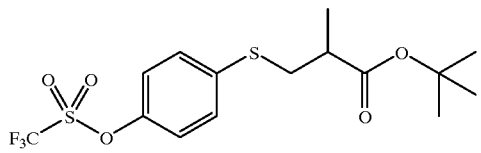

Under an atmosphere of argon and at −78° C., to a solution of the compound prepared in Example 1(2) (1.50 g) in dichioromethane (10 ml), pyridine (1.1 3 ml) and anhydrous trifluoromethanesulfonic acid (1.13 ml) were added dropwise. The mixture solution was stirred for 2 hours at room temperature. A saturated aqueous solution of sodium bicarbonate (20 ml) was added to the reaction mixture and it was vigorously stirred for 1 hour at room temperature. The reaction mixture was extracted with ethyl acetate. The extract was washed with 1N hydrochloric acid, a saturated aqueous solution of sodium bicarbonate, a saturated aqueous solution of sodium chloride, dried over anhydrous magnesium sulfate and concentrated. The residue was purified by column chromatography (hexane:ethyl acetate=19: 1) to give the title compound (2.05 g) having the following physical data.

TLC: Rf 0.29 (hexane:ethyl acetate=19:1),

NMR (CDCl$_3$+CCl$_4$ (5 drops)): δ 7.40 (2H, d, J=9.0 Hz), 7.19 (2H, d, J=9.0 Hz), 3.24 (1H, dd, J=13.2 Hz, 7.3 Hz), 2.91 (1H, dd, J=13.2 Hz, 6.8 Hz), 2.59 (1H, m), 1.45 (9H, s), 1.24 (3H, d, J=6.8 Hz).

Reference Example 2

2-methyl-3-(4-trifluoromethanesulfonyloxyphenylsulfonyl)propionic acid t-butyl ester

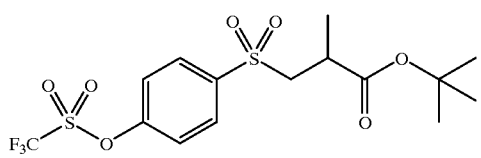

The title compound (748 mg) having the following physical data was obtained by the same procedure as Example 5, using the compound prepared in Reference example 1 (1.00 g).

mp:50° C.,

TLC: Rf 0.57 (hexane:ethyl acetate=9:1),

NMR (CDCl$_3$+CCl$_4$ (5 drops)): δ 8.05 (2H, d, J=8.6 Hz), 7.49 (2H, d, J=8.6 Hz), 3.71 (1H, dd, J=14.2 Hz, 7.6 Hz), 3.06 (1H, dd, J=14.2 Hz, 5.1 Hz), 2.96 (1H, m), 1.42 (9H, s), 1.31 (3H, d, J=7.2 Hz).

Example 6

3-(4-bromophenylsulfonyl)propionic acid t-butyl ester

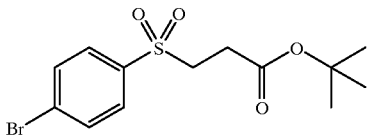

The mixture of 4-bromophenylsulfinic acid sodium salt (729 mg), 2-propenoic acid t-butyl ester (439 µl), 95% ethanol (4 ml) and acetic acid (372 µl) was stirred for 12 hours at room temperature. Further, 2-propenoic acid t-butyl ester (2.20 ml) was added to the mixture and it was refluxed for 4 hours. The reaction mixture was diluted with ethyl acetate. The mixture was washed with a saturated aqueous solution of sodium bicarbonate, a saturated aqueous solution of sodium chloride, dried over anhydrous magnesium sulfate and concentrated to give the title compound (872 mg) having the following physical data.

mp: 105° C.,

TLC: Rf 0.31 (hexane:ethyl acetate=4:1),

NMR (CDCl$_3$+CCl$_4$ (5 drops)): δ 7.78 (2H, d, J=8.8 Hz), 7.72 (2H, d, J=8.8 Hz), 3.38 (2H, t, J=7.3 Hz), 2.65 (2H, t, J=7.3 Hz), 1.40 (9H, s).

Example 7

2-methyl-3-[4-(4-tolylethynyl)phenylsulfonyl]propionic acid t-butyl ester

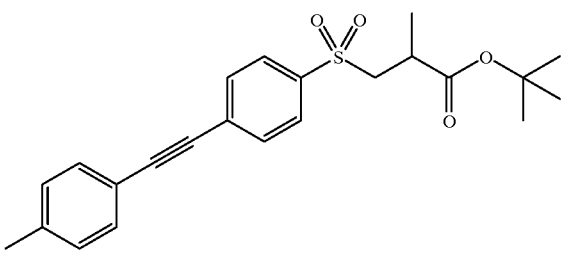

To a solution of the compound prepared in Reference example 2 (432 mg) and 4-ethynyltoluene (133 µl) in acetonitrile (10 ml), triphenylphosphine (31 mg), triethylamine (2 ml), copper iodide (8 mg) and 10% palladium-carbon (43 mg) were added successively. The mixture was refluxed for 3 hours and concentrated. The residue was purified by column chromatography (hexane:ethyl acetate= 17:3) to give the title compound (376 mg). The title compound (376 mg) was recrystallized from hexane to give the title compound (227 mg) having the following physical data.

TLC: Rf 0.41 (hexane:ethyl acetate=4:1),

NMR (CDCl$_3$+CCl$_4$ (5 drops)): δ 7.88 (2H, d, J=8.6 Hz), 7.67 (2H, d, J=8.6 Hz), 7.45 (2H. d, J=8.3 Hz), 7.19 (2H, d, J=8.3 Hz), 3.68 (1H, dd, J=13.9 Hz, 7.1 Hz), 3.01 (1H, dd, J=13.9 Hz, 5.4 Hz), 2.89 (1H, m), 1.42 (9H, s), 1.29 (3H, d, J=7.2 Hz).

Example 7(1)~7(5)

The following compounds were obtained by the same procedure as Example 7, using the compounds prepared in Example 6 or Example 5(2), and the corresponding acetylene derivatives.

Example 7(1)

3-[4-(1-heptynyl)phenylsulfonyl]propionic acid t-butyl ester

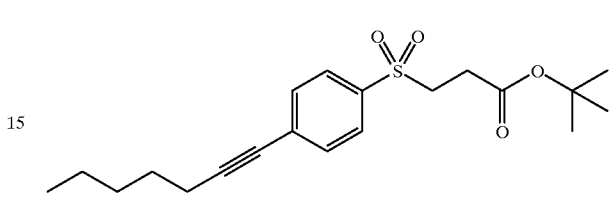

TLC: Rf 0.38 (hexane:ethyl acetate=6:1),

NMR (CDCl$_3$+CCl$_4$ (5 drops)): δ 7.81 (2H, d, J=8.6 Hz), 7.55 (2H, d, J=8.6 Hz), 3.37 (2H, t, J=7.6 Hz), 2.64 (2H, t, J=7.6 Hz), 2.44 (2H, t, J=7.1 Hz), 1.59 (2H, m), 1.20–1.50 (4H, m), 1.41 (9H, s), 0.93 (3H, t, J=6.8 Hz).

Example 7(2)

3-[4-(phenylethynyl)phenylsulfonyl]propionic acid t-butyl ester

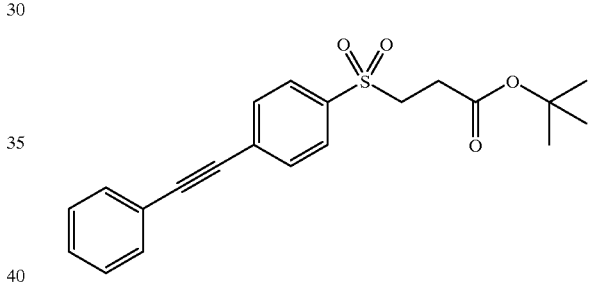

TLC: Rf 0.59 (hexane:ethyl acetate=4:1),

NMR (CDCl$_3$): δ 7.89 (2H, d, J=8.7H), 7.70 (2H, d, J=8.7 Hz), 7.58–7.53 (2H, m), 7.40–7.37 (3H, m), 3.40 (2H, t, J=7.8 Hz), 2.67 (2H, t, J=7.8 Hz), 1.41 (9H, s).

Example 7(3)

3-[4-(2-pyridylethynyl)phenylsulfonyl]propionic acid 1-butyl ester

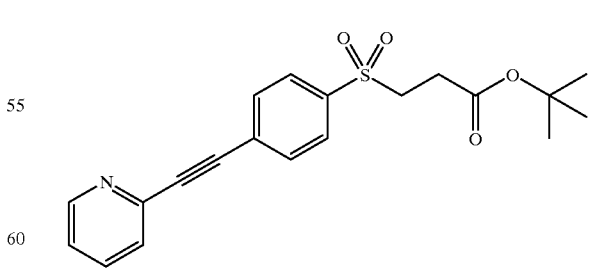

TLC: Rf 0.34 (hexane:ethyl acetate=1:1),

NMR (CDCl$_3$): δ 8.65 (1H, m), 7.92 (2H, d, J=8.6H), 7.78 (2H, d, J=8.6H), 7.70 (1H, m), 7.56 (1H, m), 7.31 (1H, m), 3.42 (2H, m), 2.69 (2H, m), 1.42 (9H, s).

Example 7(4)
3-[4-(4-methoxyphenylethynyl)phenylsulfonyl]propionic acid t-butyl ester

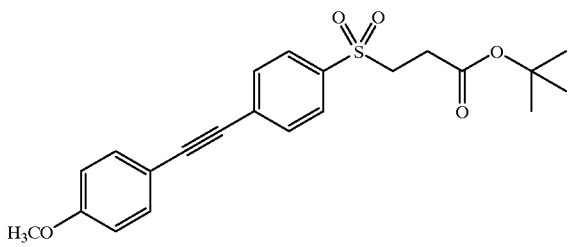

TLC: Rf 0.15 (hexane:ethyl acetate=4:1),

NMR (CDCl$_3$): δ 7.87 (2H, d, J=8.6H), 7.66 (2H, d, J=8.6H), 7.49 (2H, d, J=8.8H), 6.90 (2H, d, J=8.8H), 3.85 (3H, s), 3.40 (2H, m), 2.66 (2H, m), 1.41 (9H, s).

Example 7(5)
2-benzyl-3-[4-(4-tolylethynyl)phenylsulfonyl]propionic acid t-butyl ester

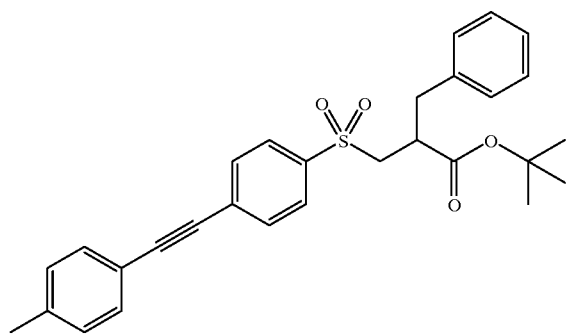

TLC: Rf 0.19 (hexane:ethyl acetate=4:1),

NMR (CDCl$_3$): δ 7.81 (2H, d, J=8.6 Hz), 7.64 (2H, d, J=8.6 Hz), 7.45 (2H, d, J=8.1 Hz), 7.30–7.15 (5H, m), 7.08 (2H, m), 3.64 (1H, m), 3.15–2.75 (4H, m), 2.40 (3H, s), 1.34 (9H, s).

Example 8
3-[4-(benzoylamino)phenylthio]propionic acid

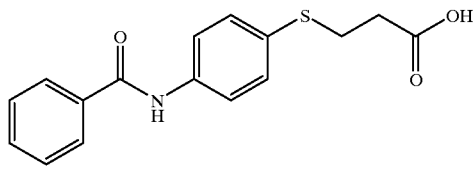

A solution of the compound prepared in Example 2 (560 mg) in trifluoroacetic acid (5 ml) was stirred for 1 hour at room temperature. The reaction solution was concentrated and benzene was added to the residue, and then the solution was concentrated again. The residue was washed with ether to give the title compound (440 mg) having the following physical data.

TLC: Rf 0.19 (chloroform:methanol=9:1),

NMR (DMSO-d$_6$): δ 12.80–11.80 (1H, br.s), 10.30 (1H, s), 7.95 (2H, dd, J=2.0 Hz, 8.2 Hz), 7.77 (2H, d, J=8.8 Hz), 7.65–7.47 (3H, m), 7.36 (2H, d, J=8.8 Hz), 3.09 (2H, t, J=7.4 Hz), 2.50 (2H, t, J=7.4 Hz).

Example 8(1)–8(11)

The following compounds were obtained by the same procedure as Example 8 (deprotection under acidic condition; for example, a solution of trifluoroacetic acid, hydrochloric acid in dioxane or ethyl acetate, are used.), using the compounds prepared in Example 4, 5, 5(1), 7, 7(1), 7(2), 7(3), 7(4), 7(5) or 1(4).

Example 8(1)
3-[4-(benzoylamino)phenylsulfinyl]propionic acid

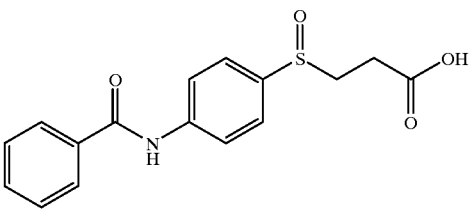

TLC: Rf 0.26 (chloroform:methanol=90:10:1),

NMR (DMSO-d$_6$): δ 12.80–11.80 (1H, br.s), 10.52 (1H, s), 8.01 (2H, d,J=8.8 Hz), 7.99–7.93 (2H, m), 7.64 (2H, d, J=8.8 Hz), 7.62–7.50 (3H, m), 3.20 (1H, ddd, J=6.8, 8.2, 13.6 Hz), 2.95 (1H, ddd, J=6.2,8.2,13.6 Hz), 2.58 (1H, ddd, J=6.8,8.2,16.8 Hz), 2.33 (1H, ddd, J=6.2,8.2,16.8 Hz).

Example 8(2)
3-[4-(benzoylamino)phenylsulfonyl]propionic acid

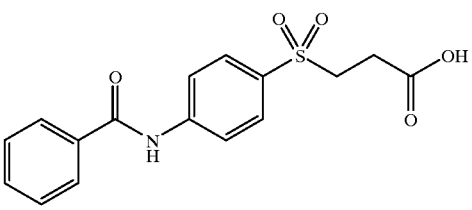

TLC: Rf 0.33 (chloroform:methanol:acetic acid 90:10:1),

NMR (DMSO-d$_6$): δ 13.20–11.80 (1H, br.s), 10.68 (1H, s), 8.07 (2H, d, J=8.8 Hz), 7.98 (2H, dd, J=1.8,8.2 Hz), 7.87 (2H, d, J=8.8 Hz), 7.70–7.50 (3H m), 3.48 (2H, t, J=7.2 Hz), 2.53 (2H, t, J=7.2 Hz).

Example 8(3)
3-[4-(benzyloxy)phenylsulfonyl]propionic acid

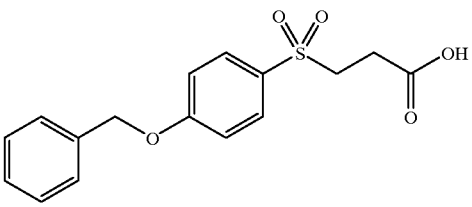

TLC: Rf 0.63 (chloroform:methanol:acetic acid 90:10:1),

NMR (DMSO-d$_6$): δ 12.70–12.40 (1H, br.s), 7.82 (2H, d, J=8.8 Hz), 7.52–7.30 (5H, m), 7.28–7.20 (2H, d, J=8.8 Hz), 5.22 (2H, s), 3.46 (2H, t, J=7.4 Hz), 2.50 (2H, t, J=7.4 Hz).

Example 8(4)

2-methyl-3-[4-(4-tolylcarbonylmethyl)phenylsulfonyl]propionic acid

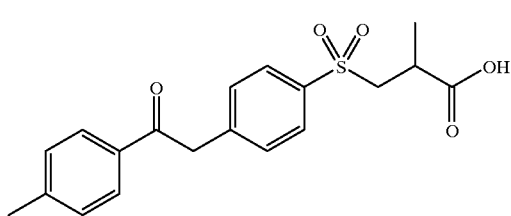

TLC: Rf 0.33 (chloroform:methanol:acetic acid= 40:1:0.2),

NMR (DMSO-$d_6$+CCl$_4$ (5 drops)): δ 12.58 (1H, s), 7.97 (2H, d, J=7.8 Hz), 7.84 (2H, d, J=8.1 Hz), 7.54 (2H, d, J=8.1 Hz), 7.36 (2H, d, J=7.8 Hz), 3.60 (1H, dd, J=14.2, 6.8 Hz), 3.39 (1H, dd, J=14.2, 5.4 Hz), 2.68 (1H, m), 2.39 (3H, s), 1.17 (3H, d, J=7.1 Hz).

Example 8(5)

2-methyl-3-[4-(4-tolylethynyl)phenylsulfonyl]propionic acid

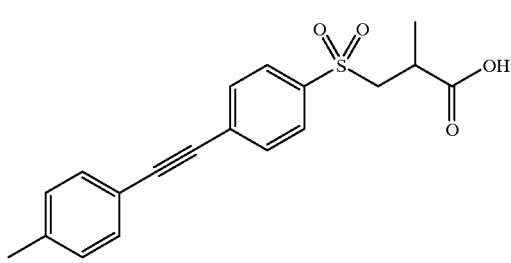

TLC: Rf 0.35 (chloroform:methanol=10:1),

NMR (DMSO-$d_6$+CCl$_4$ (5 drops)): δ 12.57 (1H, s), 7.91 (2H, d, J=8.6 Hz), 7.79 (2H, d, J=8.6 Hz), 7.50 (2H, d, J=8.3 Hz), 7.27 (2H, d, J=8.3 Hz), 3.66 (1H, dd, J=14.4, 7.3 Hz), 3.44 (1H, dd, J=14.4, 5.4 Hz), 2.70 (1H, m), 2.36 (3H, s), 1.18 (3H, d, J=7.1 Hz).

Example 8(6)

3-[4-(1-heptynyl)phenylsulfonyl]propionic acid

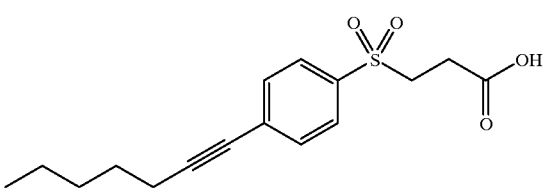

mp: 122~123° C.,

TLC: Rf 0.78 (chloroform:methanol:acetic acid=9:1:0.5),

NMR (DMSO-$d_6$+CCl$_4$ (5 drops)): δ 12.54 (1H, s), 7.84 (2H, d, J=8.2 Hz), 7.63 (2H, d, J=8.2 Hz), 3.52 (2H, t, J=7.4 Hz), 2.40–2.60 (4H, m), 1.57 (2H, m), 1.37 (4H, m), 0.90 (3H, t, J=7.0 Hz).

Example 8(7)

3-[4-(phenylethynyl)phenylsulfonyl]propionic acid

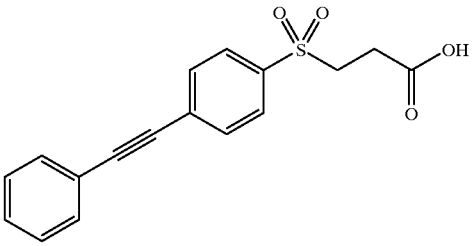

TLC: Rf 0.47 (chloroform:methanol=4:1),

NMR (DMSO-$d_6$): δ 12.49 (1H, br.s), 7.93 (2H, d, J=8.5 Hz), 7.78 (2H, d, J=8.5 Hz), 7.61–7.56 (2H, m), 7.55–7.42 (3H, m), 3.52 (2H, t, J=7.3 Hz), 2.56 (2H, t, J=7.3 Hz).

Example 8(8)

3-[4-(2-pyridylethynyl)phenylsulfonyl]propionic acid

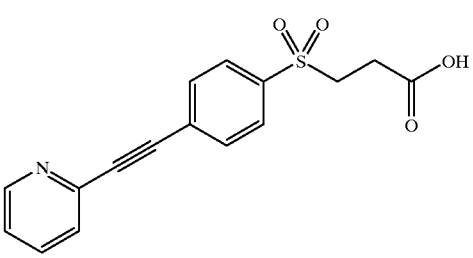

TLC: Rf 0.39 (chloroform:methanol:acetic acid= 100:10:1),

NMR (CDCl$_3$+CD$_3$OD (3 drops)): δ 8.63 (1H, m), 7.94 (2H, d, J=8.6 Hz), 7.83–7.73 (3H, m), 7.60 (1H, m), 7.36 (1H, m), 3.47 (2H, m), 2.75 (2H, m).

Example 8(9)

3-[4-(4-methoxyphenylethynyl)phenylsulfonyl]propionic acid

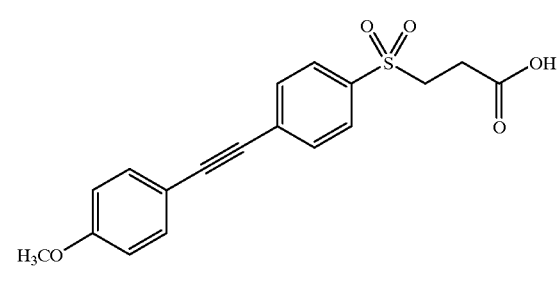

TLC: Rf 0.42 (chloroform:methanol:acetic acid= 100:10:1),

NMR (CDCl$_3$+CD$_3$OD (3 drops)): δ 7.87 (2H, d, J=8.6 Hz), 7.66 (2H, d, J=8.6 Hz), 7.50 (2H, d, J=9.0 Hz), 6.91 (2H, d, J=9.0 Hz), 3.85 (3H, s), 3.44 (2H, m), 2.73 (2H, m).

Example 8(10)

2-benzyl-3-[4-(4-tolylethynyl)phenylsulfonyl]propionic acid

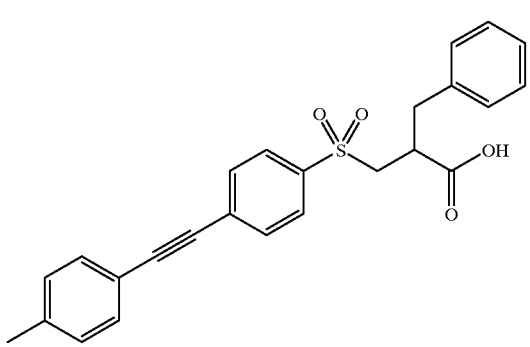

TLC: Rf 0.45 (chloroform:methanol:acetic acid=100:10:1),

NMR (CDCl$_3$+CD$_3$OD (3 drops)): δ 7.77 (2H, d, J=8.6 Hz), 7.62 (2H, d, J=8.6 Hz), 7.45 (2H, d, J=8.1 Hz), 7.30–7.15 (5H, m), 7.04 (2H, m), 3.67 (1H, m), 3.15–3.05 (3H, m), 2.82 (1H, m), 2.40 (3H, s).

Example 8(11)

3-(4-methoxyphenylthio)propionic acid

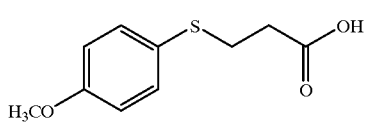

TLC: Rf 0.48 (chloroform:methanol=10:1),

NMR (CDCl$_3$): δ 7.39 (2H, d, J=8.8 Hz), 6.85 (2H, d, J=8.8 Hz), 3.80 (3H, s), 3.04 (2H, t, J=7.2 Hz), 2.61 (2H, t, J=7.2 Hz).

Example 9

N-t-butoxy-3-(4-methoxyphenylthio)propionamide

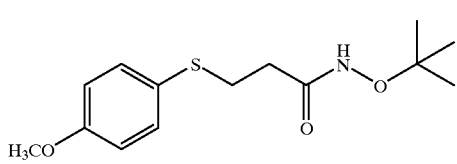

To a solution of the compound prepared in Example 8(11) (1.00 g) in DMF (20 ml), t-butoxyamine hydrochloride (652 mg), triethylamine (0.8 ml), 1-ethyl-3-(3-dimethylaminopropyl)-carbodiimide (EDC) hydrochloride (995 mg) and 1-hydroxybenzotriazole (HOBt) hydrate (795 mg) were added at 0° C. The mixture was stirred for 16 hours at room temperature. To the reaction mixture, ethyl acetate and water were added. The organic phase was washed with 0.1 N hydrochloric acid, a saturated aqueous solution of sodium bicarbonate, water and a saturated aqueous solution of sodium chloride, successively, dried over anhydrous magnesium sulfate and concentrated to give the title compound (1.35 g) having the following physical data.

TLC: Rf 0.76 (chloroform:methanol=10:1).

Example 9(1)

N-benzyloxy-3-(4-methoxyphenylthio)propionamide

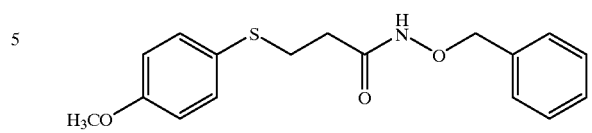

The title compound (423 mg) having the following physical data was obtained by the same procedure as Example 9, using the compound prepared in Example 8(11) (300 mg) and benzyloxyamine hydrochloride (271 mg).

TLC: Rf 0.65 (chloroform:methanol=10:1),

NMR (DMSO-d$_6$): δ 7.38 (5H, m), 7.33 (2H, d, J=8.6 Hz), 6.91 (2H, d, J=8.6 Hz), 4.77 (2H, s), 3.74 (3H, s), 3.01 (2H, t, J=7.4 Hz), 2.21 (2H, t, J=7.4 Hz).

Example 10

N-benzyloxy-3-(4-methoxyphenylsulfonyl)propionamide

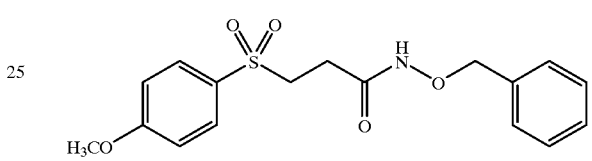

The title compound (152 mg) having the following physical data was obtained by the same procedure as Example 5, using the compound prepared in Example 9(1) (159 mg).

TLC: Rf 0.48 (chloroform:methanol=20:1).

Reference Example 3

N-t-butoxycarbonyl-N-t-butoxycarbonyloxy-3-(4-methoxyphenylthio)propionamide

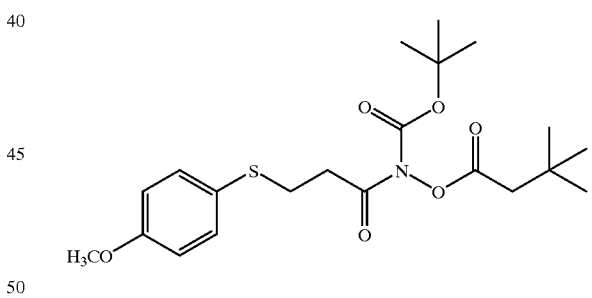

To a solution of the compound prepared in Example 8(11) (106 mg) in DMF (5 ml), N-t-butoxycarbonyl-N-t-butoxycarbonyloxyamine (120 mg), EDC hydrochloride (106 mg) and 4-(dimethylamino)pyridine (6 mg) were added at 0° C. The mixture was stirred for 16 hours at room temperature. To the reaction solution, water was added and it was extracted with ethyl acetate. The extract was washed with a saturated aqueous solution of ammonium chloride, a saturated aqueous solution of sodium bicarbonate, a saturated aqueous solution of sodium chloride, dried over anhydrous magnesium sulfate and concentrated to give the title compound (211 mg) having the following physical data.

TLC: Rf 0.48 (hexane:ethyl acetate=4:1).

NMR (DMSO-d$_6$): δ 7.35 (2H, d, J=8.6 Hz), 6.93 (2H, d, J=8.6 Hz), 3.74 (3H, s), 3.18 (2H, m), 3.05 (2H, m), 1.46 (9H, s), 1.43 (9H, s).

Reference Example 4
N-t-butoxycarbonyl-N-t-butoxycarbonyloxy-3-(4-methoxyphenylsulfinyl)propionamide

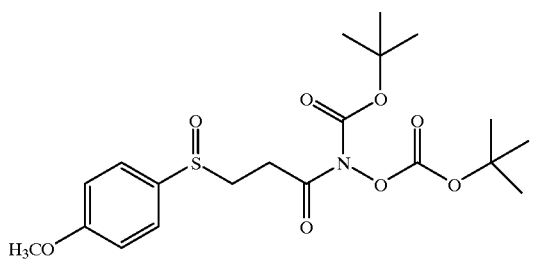

The title compound (quant) having the following physical data was obtained by the same procedure as Example 4, using the compound prepared in Reference example 3 (190 mg).

TLC: Rf 0.36 (chloroform:methanol=20:1),
NMR (DMSO-d$_6$): δ 7.58 (2H, d, J=8.6 Hz), 7.15 (2H, d, J=8.6 Hz), 3.83 (3H, s), 3.28–3.08 (2H, m), 3.05–2.80 (2H, m), 1.46 (9H, s), 1.44 (9H, s).

Example 11
N-hydroxy-3-(4-methoxyphenylthio)propionamide

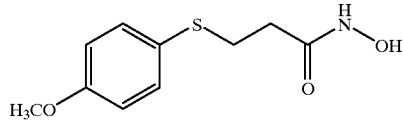

The mixture of the compound prepared in Example 9 (200 mg) and 30% hydrogen bromide in acetic acid (2 ml) was stirred for 1 hour at room temperature. The reaction mixture was concentrated. The residue was purified by column chromatography (chloroform:methanol=10:1) to give the title compound (138 mg) having the following physical data.

TLC: Rf 0.33 (chloroform:methanol=10:1),
NMR(DMSO-d$_6$): δ 10.42 (1H, br.s), 8.79 (1H, s), 7.33 (2H, d, J=8.6 Hz), 6.92 (2H, d, J=8.6 Hz), 3.75 (3H, s), 3.01 (2H, t, J=7.4 Hz), 2.20 (2H, t, J=7.4 Hz).

Example 11(1)~11(2)

The following compounds were obtained by the same procedure as Example 11 (deprotection under acidic condition; for example, hydrogen bromide in acetic acid, trifluoroacetic acid are used.), or the same desired procedure (hydrogenolysis) as Example 11, using the compounds prepared in Reference example 4 or Example 10.

Example 11(1)
N-hydroxy-3-(4-methoxyphenylsulfinyl)propionamide

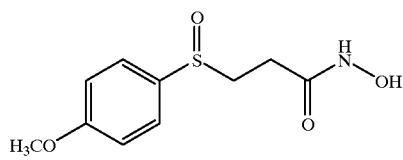

TLC: Rf 0.46 (chloroform:methanol=4:1).
NMR (DMSO-d$_6$) δ 10.50 (1H, br.s), 8.82 (1H, br.s), 7.58 (2H, d, J=8.6 Hz), 7.15 (2H, d, J=8.6 Hz), 3.82 (3H, s), 3.20–3.03 (1H, m), 3.00–2.83 (1H, m), 2.43–2.25 (1H, m), 2.10–1.93 (1H, m).

Example 11 (2)
N-hydroxy-3-(4-methoxyphenylsulfonyl)propionamide

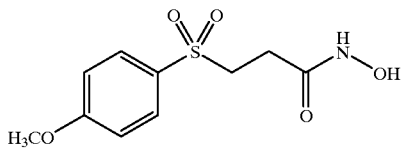

TLC: Rf 0.66 (chloroform:methanol=4:1),
NMR (DMSO-d$_6$): δ 10.50 (1H, br.s), 8.85 (1H, s), 7.82 (2H, d, J=8.6 Hz), 7.17 (2H, d, J=8.6 Hz), 3.87 (3H, s), 3.43 (2H, m), 2.27 (2H, m).

Example 12
2-t-butoxycarbonylamino-3-(4-methoxyphenylthio)propionic acid benzyl ester

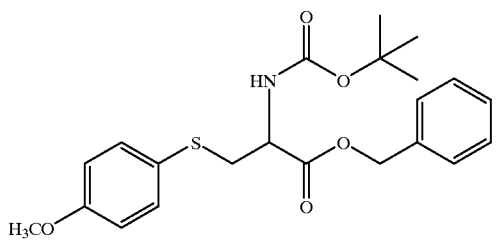

To a solution of 2-t-butoxycarbonylamino-3-hydroxypropionic acid benzyl ester (29.5 g) in dichloromethane (300 ml), triethylamine (21 ml) and mesyl chloride (8.6 ml) were added and the reaction solution was stirred for 30 minutes at 4° C. The reaction solution was added to 1 N hydrochloric acid cooling with ice. The obtained yellow oil was dissolved into dichloromethane (300 ml), and diisopropylethylamine (17 ml) and 4-methoxybenzenethiol (12 ml) were added thereto at 4° C. and the reaction solution was stirred for 3 hours at room temperature and concentrated. The residue was purified by column chromatography (n-hexane:ethyl acetate=8:1) to give the title compound (24.8 g) having the following physical data.

TLC: Rf 0.65 (ethyl acetate:n-hexane=1:2),
NMR (CD$_3$OD): δ 7.42–7.20 (7H, m), 6.80 (2H, d, J=9.0 Hz), 5.35 (1H, m), 5.02 (1H, d, J=12.5 Hz), 4.85 (1H, d, J=12.5 Hz), 4.55 (1H, m), 3.78 (3H, s), 3.25 (2H, d, J=5.0 Hz), 1.40 (9H, s).

Example 13
2-t-butoxycarbonylamino-3-(4-methoxyphenylsulfonyl)propionic acid benzyl ester

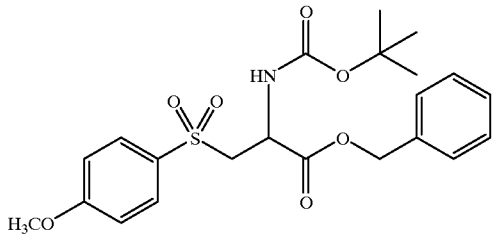

To a solution of the compound prepared in Example 12 (20.9 g) in dichloromethane (200 ml), 70% m-chloroperbenzoic acid (26.0 g) was added and the reaction solution was stirred for 72 hours at room temperature. The reaction solution was added to water and it was extracted with dichloromethane. The organic layer was dried over anhydrous magnesium sulfate, filterd and concentrated. The residue was washed with n-hexane and the precipitate was dissolved into ethyl acetate. The organic layer was washed with a saturated aqueous solution of sodium bicarbonate, a saturated aqueous solution of sodium chloride, dried over anhydrous magnesium sulfate, filtered and concentrated. The residue was washed with n-hexane to give the title compound (16.7 g) having the following physical data.

TLC: Rf 0.29 (ethyl acetate:n-hexane=1:2),

NMR (CD$_3$OD) δ 7.78 (2H, d, J=9.0 Hz), 7.45–7.30 (5H, m), 6.98 (2H, d, J=9.0 Hz), 5.50 (1H, d, J=7.5 Hz), 5.18 (1H, d, J=11.0 Hz), 5.06 (1 H. d, J=11.0 Hz), 4.60 (1H, m), 3.88 (3H, s), 3.72 (2H, d, J=5.0 Hz), 1.35 (9H, s).

Example 14
2-t-butoxycarbonylamino-3-(4-methoxyphenylsulfonyl) propionic acid

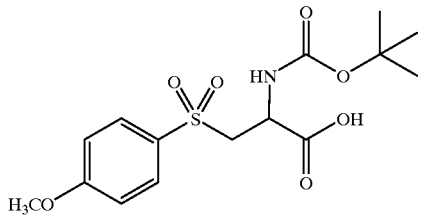

Under an atmosphere of nitrogen, to a solution of the compound prepared in Example 13 (1.35 g) in THF (15 ml), 10% palladium-carbon (100 g) was added and the reaction solution was stirred for 45 minutes at room temperature under an atmosphere of hydrogen. 10% palladium-carbon was removed from the reaction solution and then the solution was concentrated. The residue was washed with ether to give the title compound (1.02 g) having the following physical data.

TLC: Rf 0.57 (chloroform:methanol:acetic acid=9:1:1),

NMR (DMSO-d$_6$): δ 7.79 (2H, d, J=8.8 Hz), 7.16 (2H, d, J=8.8 Hz), 7.05 (1H, d, J=8.4 Hz), 4.26 (1H, m), 3.87 (3H, s), 3.61 (2H, m), 1.32 (9H, s).

Example 15
2-amino-3-(4-methoxyphenylsulfonyl)propionic acid benzyl ester hydrochloride

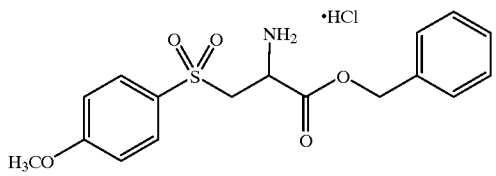

The title compound having the following physical data was obtained by the same procedure as Example 8, using the compound prepared in Example 13.

TLC: Rf 0.54 (chloroform:methanol=18:1),

NMR (DMSO-d$_6$): δ 9.00–8.80 (3H, br), 7.85 (2H, d, J=9.0 Hz), 7.42–7.35 (5H, m), 7.15 (2H, d, J=9.0 Hz), 5.18 (1H, d, J=12.5 Hz), 4.98 (1H, d, J=12.5 Hz), 4.45 (1H, t, J=5.0 Hz), 3.95 (2H, d, J=5.0 Hz), 3.86 (3HJ, s).

Example 16~16(2)

The following compounds were obtained by the same procedure as Example 9, using the compound prepared in Example 15 and the corresponding carboxylic acids.

Example 16

2-[N-[N-(t-butoxycarbonyl)phenylglycyl]amino]-3-(4-methoxyphenylsulfonyl)propionic acid benzyl ester

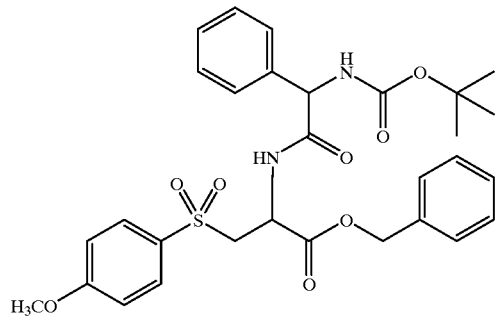

TLC: Rf 0.51 (ethyl acetate:n-hexane=1:1),

NMR (DMSO-d$_6$): δ 8.88 and 8.75 (total 1H, d and d, J=7.8 and 7.8 Hz), 7.79 and 7.74 (total 2H, d and d, J=9.0 and 9.0 Hz), 7.42–7.20 (10H, m), 7.14 and 7.10 (total 2H, d and d, J=9.0 and 9.0 Hz), 5.20–4.95 (3H, m), 4.80–4.65 and 4.63–4.45 (total 1H, m and m), 3.88 and 3.87 (total 3H, s and s), 3.80–3.60 (2H, m), 1.38 (9H, s).

Example 16(1)

2-acetylamino-3-(4-methoxyphenylsulfonyl)propionic acid benzyl ester

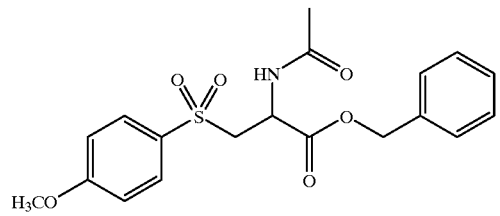

TLC: Rf 0.53 (chloroform:methanol=18:1),

NMR (CDCl$_3$): 7.76 (2H, d, J=9.2 Hz), 7.45–7.30 (5H, m), 6.99 (2H, d, J=9.2 Hz), 6.54 (1H, d, J=7.0 Hz), 5.19 (1H, d, J=11.8 Hz), 5.09 (1H, d, J=11.8 Hz), 4.87 (1H, m), 3.88 (3H, s), 3.80–3.70 (2H, m), 1.93 (3H, s).

Example 16(2)
2-[N-[N-(t-butoxycarbonyl)glycyl]amino]-3-(4-methoxyphenylsulfonyl)propionic acid benzyl ester

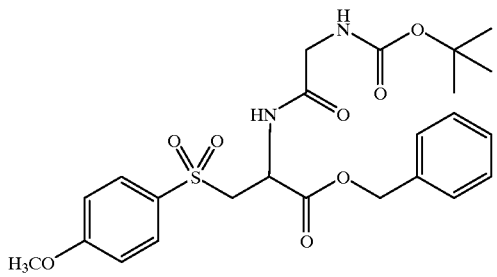

TLC: Rf 0.31 (ethyl acetate:n-hexane=1:1),
NMR (DMSO-$d_6$): δ 8.40 (1H, d, J=8.0 Hz), 7.80 (2H, d, J=9.0 Hz), 7.45–7.25 (5H, m), 7.18 (2H, d, J=9.0 Hz), 6.95 (1H, m), 5.08 (2H, s), 4.70 (1H, m), 3.88 (3H, s), 3.80–3.60 (2H, m), 3.45–3.30 (2H, m, overlap with $H_2O$ in DMSO), 1.40 (9H, s).

Example 17~17(2)

The following compounds were obtained by the same procedure as Example 14, using the compounds prepared in Example 16~16(2).

Example 17
2-[N-[N-(t-butoxycarbonyl)phenylglycyl]amino]-3-(4-methoxyphenylsulfonyl)propionic acid

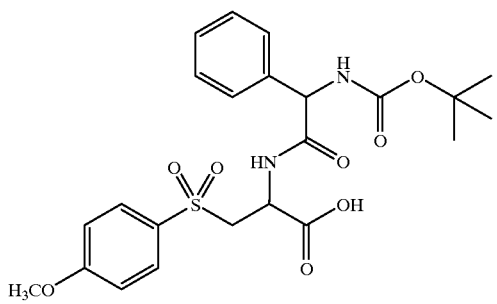

TLC: Rf 0.30 (chloroform:methanol:acetic acid 90:10:1),
NMR ($CD_3OD$): δ 7.81 and 7.72 (total 2H, each d, J=9.2 Hz), 7.35 (5H, m), 7.10 and 7.50 (total 2H, each d, J=9.2 Hz), 5.11 and 5.03 (total 1H, each brs), 4.76 and 4.55 (total 1H, each dd, J=8.6 Hz, 3.7 Hz), 3.90 and 3.89 (total 3H, each s), 3.84–3.57 (2H, m), 1.44 (9H, s).

Example 17(1)
2-acetylamino-3-(4-methoxyphenylsulfonyl)propionic acid

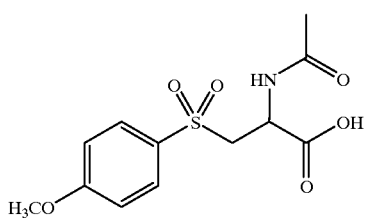

TLC: Rf 0.46 (ethyl acetate:acetic acid:water=3:1:1),
NMR ($CDCl_3+CD_3OD$): δ 7.82 (2H, d, J=8.8 Hz), 7.03 (2H, d, J=8.8 Hz), 4.73 (1H, m), 3.89 (3H, s), 3.82–3.70 (2H, m), 1.91 (3H, s).

Example 17(2)
2-[N-[N-(t-butoxycarbonyl)glycyl]amino]-3-(4-methoxyphenylsulfonyl)propionic acid

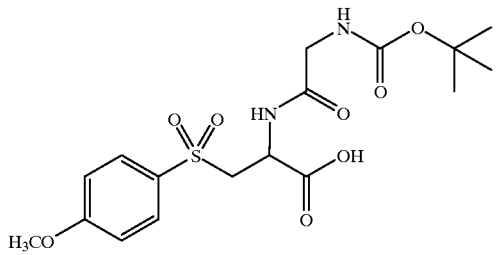

TLC: Rf 0.38 (chloroform:methanol:acetic acid=80:20:1),
NMR ($CDCl_3+CD_3OD$): δ 7.82 (2H, d, J=9.0 Hz), 7.03 (2H, d, J=9.0 Hz), 4.75 (1H, m), 3.89 (3H, s), 3.75 (4H, m), 1.46 (9H, s).

Example 18~18(2)

The following compounds were obtained by the same procedure as a series of reactions of Example 8→Example 9 (the corresponding carboxylic acids are used.)→Example 14, using the compound prepared in Example 16(2).

Example 18
2-[N-[N-(t-butoxycarbonyl)phenylglycyl-glycyl]amino]-3-(4-methoxyphenylsulfonyl)propionic acid

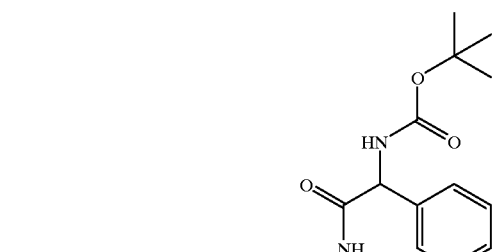

TLC: Rf 0.43 (chloroform:methanol:acetic acid 80:20:1),
NMR (DMSO-$d_6$): δ 8.29 (2H, m), 7.77 and 7.75 (total 2H, each d, J=9.0 Hz), 7.41 (2H, m), 7.30 (4H, m), 7.12 and 7.10 (total 2H, each d, J=9.0 Hz), 5.25 (1H, 2m), 4.53 (1H, m), 3.84 and 3.82 (total 3H, each s), 3.78–3.45 (4H, m), 1.38 (9H, s).

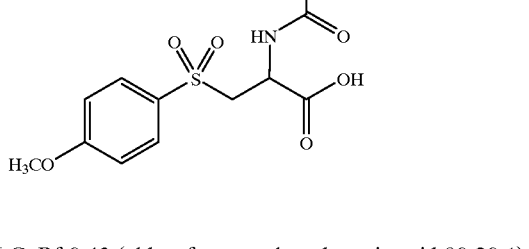

Example 18(1)

2-[N-(N-acetylglycyl)amino]-3-(4-methoxyphenylsulfonyl)propionic acid

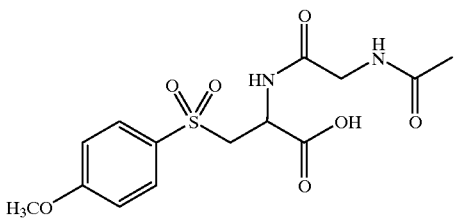

TLC: Rf 0.32 (ethyl acetate acetic acid:water=3:1:1),

NMR (DMSO-d$_6$+CD$_3$OD): δ 7.80 (2H, d, J=8.8 Hz), 7.15 (2H, d, J=8.8 Hz), 4.60 (1H, dd, J=8.3 and 4.0 Hz), 3.89 (3H, s), 3.85–3.50 (4H, m), 1.89 (3H, s).

Example 18(2)

2-[N-[N-(benzylcarbonyl)glycyl]amino]-3-(4-methoxyphenylsulfonyl)propionic acid

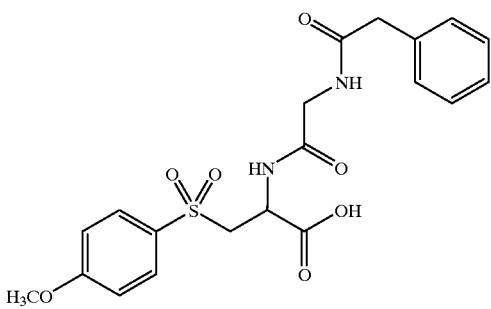

TLC: Rf 0.61 (ethyl acetate:acetic acid:water=3:1:1),

NMR (DMSO-d$_6$+CD$_3$OD): δ 7.79 (2H, d, J=8.8 Hz), 7.40–7.20 (5H, m), 7.12 (2H, d J=8.8 Hz), 4.59 (1H, m), 3.85 (3H, s), 3.82–3.40 (6H, m).

Example 19~19(6)

The following compounds were obtained by the same procedure as a series of reactions of Example 9 Example 14, using the compounds prepared in Example 14, 17~17(2), 18~18(2).

Example 19

N-hydroxy-2-t-butoxycarbonylamino-3-(4-methoxyphenylsulfonyl)propionamide

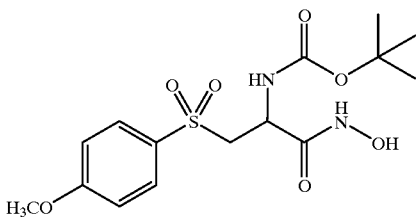

TLC: Rf 0.62 (chloroform:methanol:acetic acid=9:1:1).

Example 19(1)

N-hydroxy-2-[N-[N-(t-butoxycarbonyl)phenylglycyl]amino]-3-(4-methoxyphenylsulfonyl)propionamide

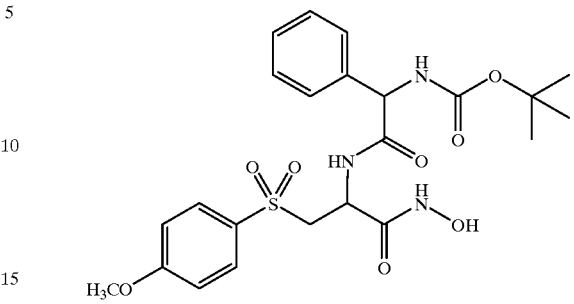

TLC: Rf 0.55 (chloroform:methanol:acetic acid=90:10:1),

NMR (DMSO-d$_6$): δ 10.65 (1H, br), 9.04 and 8.98 (total 1H, each br), 8.59 and 8.57 (total 1H, each d, J=8.2 Hz), 7.77 and 7.66 (total 2H, each d, J=9.0 Hz), 7.32 (6H, m), 7.13 and 7.08 (total 2H, each d, J=9.0 Hz), 5.00 (1H, d, J=8.2 Hz), 4.50 (1H, m), 3.87 (3H, s), 3.59 (2H, m), 1.38 (9H, s).

Example 19(2)

N-hydroxy-2-acetylamino-3-(4-methoxyphenylsulfonyl)propionamide

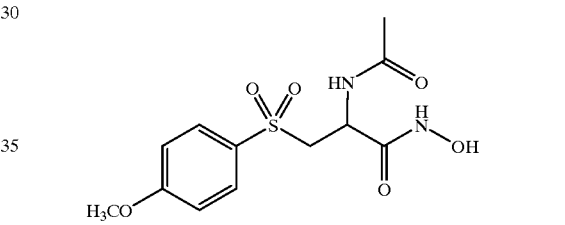

TLC: Rf 0.31 (chloroform:methanol:acetic acid=80:10:1),

NMR (DMSO-d$_6$): δ 11.00–8.60 (2H, br), 8.06 (1H, d, J=8.6 Hz), 7.76 (2H, d, J=8.0 Hz), 7.14 (2H, d, J=8.0 Hz), 4.56 (1H, m), 3.86 (3H, s), 3.55 (2H, m), 1.63 (3H, s).

Example 19(3)

N-hydroxy-2-[N-[N-(t-butoxycarbonyl)glycyl]amino]-3-(4-methoxyphenylsulfonyl)propionamide

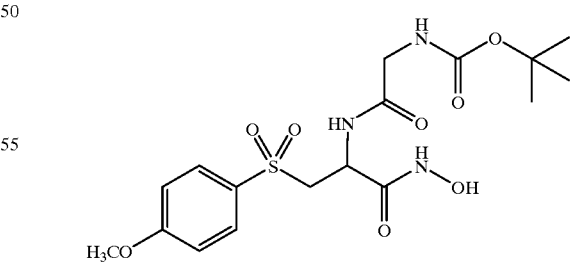

TLC: Rf 0.40 (chloroform:methanol:acetic acid=90:10:1),

NMR (DMSO-d$_6$): δ 10.62 (1H, brs), 8.99 (1H, brs), 8.15 (1H, d, J=8.4 Hz), 7.75 (2H, d, J=8.8 Hz), 7.14 (2H, d, J=8.8 Hz), 6.87 (1H, m), 4.59 (1H, m), 3.87 (3H, s), 3.65–3.24 (4H, m), 1.39 (9H, s).

Example 19(4)

N-hydroxy-2-[N-[N-(t-butoxycarbonyl)phenylglycyl-glycyl]amino]-3-(4-melhoxyphenylsulfonyl)propionamide

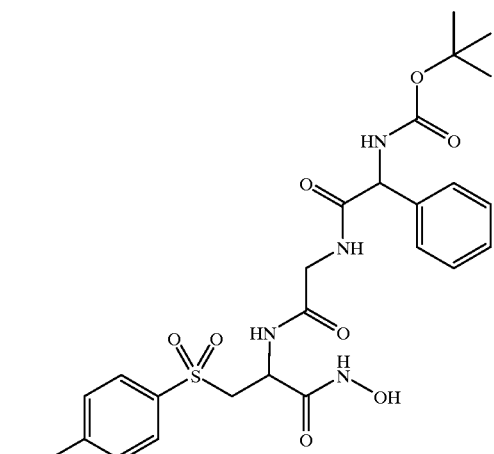

TLC: Rf 0.45 (chloroform:methanol:acetic acid= 90:10:1),

NMR (DMSO-$d_6$): δ 11.00–10.40 (1H, br), 9.20–8.60 (1H, br), 8.23 (2H, m), 7.75 and 7.73 (total 2H, each d, J=8.6 Hz), 7.44–7.29 (6H, m), 7.12 and 7.08 (total 2H, each d, J=8.6 Hz), 5.24 (1H, m), 4.60 (1H, m), 3.83 and 3.80 (total 3H, each s), 3.66–3.33 (4H, m, overlap with H2O in DMSO), 1.38 (9H, s).

Example 19(5)

N-hydroxy-2-[N-(N-acetylglycyl)amino]-3-(4-methoxyphenylsulfonyl)propionamide

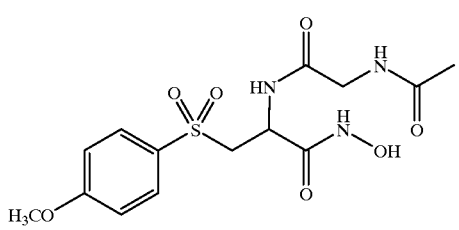

TLC: Rf 0.45 (ethyl acetate:acetic acid:water=3:1:1),

NMR (DMSO-$d_6$+CD$_3$OD): δ 7.76 (2H, m), 7.14 (2H, m), 4.60 (1H, m), 3.87 (3H, s), 3.70–3.30 (4H, m), 1.87 (3H, s).

Example 19(6)

N-hydroxy-2-[N-[N-(benzylcarbonyl)glycyl]amino]-3-(4-methoxyphenylsulfonyl)propionamide

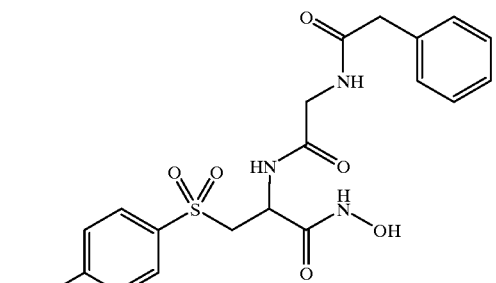

TLC: Rf 0.37 (chloroform:methanol:acetic acid= 90:10:1),

NMR (DMSO-$d_6$+CD$_3$OD): δ 7.78 (2H, m), 7.30 (7H, m), 4.60 (1H, m), 3.90–3.30 (9H, m).

Example 20~20(4)

The following compounds were obtained by the same procedure as Example 8, using the compounds prepared in Example 14, 19, 17, 19(1), 19(4).

Example 20

2-amino-3-(4-methoxyphenylsulfonyl)propionic acid trifluoroacetic acid salt

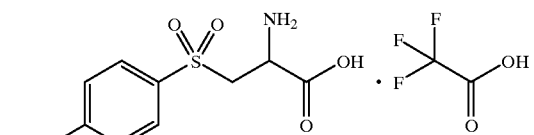

TLC: Rf 0.60 (chloroform:methanol:acetic acid=5:4:1),

NMR (CD$_3$OD): δ 7.94 (2H, d, J=9.2 Hz), 7.18 (2H, d, J=9.2 Hz), 4.43 (1H, dd, J=8.6 Hz, 3.4 Hz), 3.92 (3H, s), 3.89 (1H, dd, J=15.2 Hz, 3.4 Hz), 3.71 (1H, dd, J=15.2 Hz, 8.6 Hz).

Example 20(1)

N-hydroxy-2-amino-3-(4-methoxyphenylsulfonyl)propionamide hydrochloride

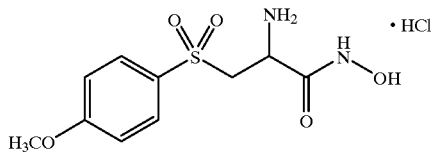

TLC: Rf 0.64 (chloroform:methanol:acetic acid=5:4 1),

NMR (DMSO-$d_6$): δ 11.38 (1H, s), 9.60–9.25 (1H, br), 8.90–8.50 (3H, br), 7.90 (2H, d, J=8.8 Hz), 7.21 (2H, d, J=8.8 Hz), 3.90 (4H, m), 3.75 (2H, m).

Example 20(2)

2-[N-(phenylglycyl)amino]-3-(4-methoxyphenylsulfonyl)propionic acid trifluoroacetic acid salt

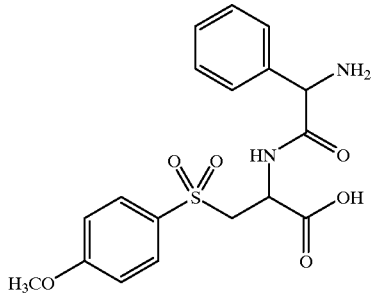

TLC: Rf 0.24 and 0.29 (ethyl acetate:acetic acid:water= 3:1:1),

NMR (CD₃OD) δ 7.83 and 7.67 (total 2H, each d, J=8.8 Hz), 7.48 (5H, m), 7.13 and 7.03 (total 2H, each d, J=8.8 Hz), 4.88 and 4.61 (total 2H, each m, overlap with H₂O in CD₃OD), 3.91 and 3.89 (total 3H, each s), 3.80 and 3.73 (total 1H, each m), 3.62–3.50 (1H, m).

Example 20(3)

N-hydroxy-2-[N-(phenylglycyl)amino]-3-(4-methoxyphenylsulfonyl)propionamide trifluoroacetic acid salt

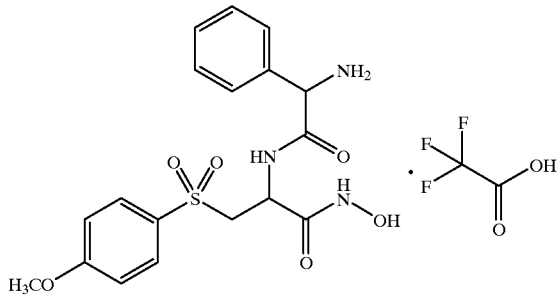

TLC: Rf 0.46 and 0.51 (ethyl acetate:acetic acid:water= 3:1:1),

NMR (DMSO-d₆): δ 10.90 (1H, br), 9.04 (2H, m), 8.58 (3H, br), 7.82 and 7.58 (total 2H, each d, J=8.8 Hz), 7.45 (5H, m), 7.17 and 7.06 (total 2H, each d, J=8.8 Hz), 4.98 and 4.81 (total 1H, each br), 4.50 (1H, m), 3.88 and 3.86 (total 3H, each s), 3.64 (1H, m), 3.40 (1H, m, overlap with H₂O in DMSO).

Example 20(4)

N-hydroxy-2-[N-(phenylglycyl-glycyl)amino]-3-(4-methoxyphenylsulfonyl)propionamide trifluoroacetic acid salt

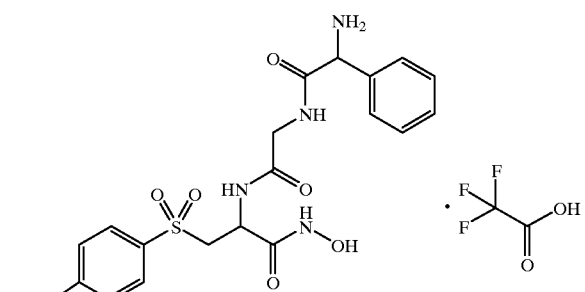

TLC: Rf 0.48 (ethyl acetate:acetic acid:water=3:1:1),

NMR (DMSO-d₆): δ 10.81 (1H, m), 9.00 (1H, m), 8.64 (4H, m), 8.35 (1H, m), 7.77 and 7.74 (total 2H, each d, J=8.8 Hz), 7.53 (2H, m), 7.43 (3H, m), 7.15 and 7.07 (total 2H, each d, J=8.8 Hz), 5.07 (1H, m), 4.61 (1H, m), 3.87 and 3.79 (total 3H, each s), 3.68–3.34 (4H, m, overlap with H₂O in DMSO).

Reference Example 5

S-oxiranecarboxylic acid t-butyl ester

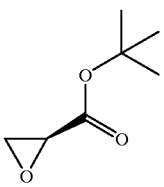

To a solution of S-oxiranecarboxylic acid potassium salt (1.26 g) in dichloromethane (45 ml), pyridinium p-tosylate (1.50 g) and N, N'-diisopropyl-O-t-butylisourea (1.50 g) were added at 0° C. and the reaction solution was stirred for 4 hours at room temperature. The reaction solution was passed through a short silica gel column (n-hexane:ethyl acetate=3:1) to give the title compound (932 mg) having the following physical data.

TLC: Rf 0.70 (ethyl acetate:n-hexane=1:3),

NMR (CDCl₃): δ 3.32 (1H, dd, J=2.8 Hz, 3.7 Hz), 2.94–2.85 (2H, m), 1.50 (9H, s).

Example 21

2R-hydroxy-3-(4-bromophenylsulfonyl)propionic acid t-butyl ester

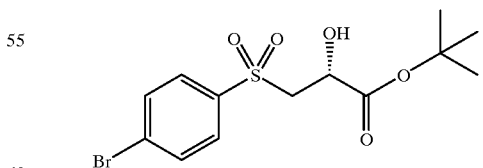

To a mixture solution of the compound prepared in Reference example 5 (565 mg) in water (8.0 ml)+benzene (8.0 ml), poly ethylene glycol 4000 (98 mg) and 4-bromophenylsulfinic acid sodium salt (4.3 g) were added and the reaction solution was refluxed for 7 hours. The reaction solution was added to water and it was extracted with ethyl acetate. The organic layer was washed with a saturated aqueous solution of sodium chloride, dried over anhydrous magnesium sulfate, filtered and concentrated. The residue was purified by silica gel column chromatography (toluene:ethyl acetate=8 1) to give the title compound (490 mg) having the following physical data.

TLC: Rf 0.56 (ethyl acetate:n-hexane=1:2),

NMR (CDCl$_3$): δ 7.28 (2H, d, J=8.8 Hz), 7.70 (2H, d, J=8.8 Hz), 4.55–4.48 (1H, m), 3.63 (1H, dd, J=3.0, 14.7 Hz), 3.44 (1H, dd, J=7.9, 14.7 Hz), 3.08 (1H, d, J=4.1 HZ), 1.51 (9H, s).

Example 22

2R-hydroxy-3-[4-(4-tolylethynyl)phenylsulfonyl]propionic acid

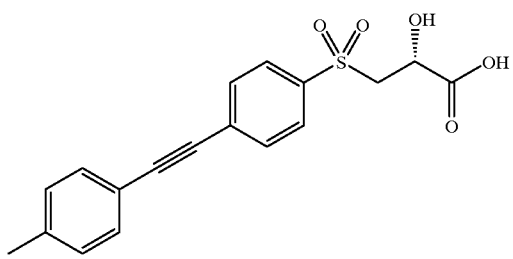

The title compound was obtained by the same procedure as a series of reactions of Example 7→Example 8, using the compound prepared in Example 21.

TLC: Rf 0.23 (chloroform:methanol:acetic acid=8:1:1),

NMR (DMSO-d$_6$3): δ 7.91 (2H, d, J=8.0 Hz), 7.75 (2H, d, J=8.0 Hz), 7.50 (2H, d, J=8.0 Hz), 7.27 (2H, d, J=8.0 Hz), 4.22–4.26 (1H, m), 3.46–3.64 (2H, m), 2.35 (3H, s).

Example 23

2S-hydroxy-3-[4-(4-tolylethynyl)phenylsulfonyl]propionic acid

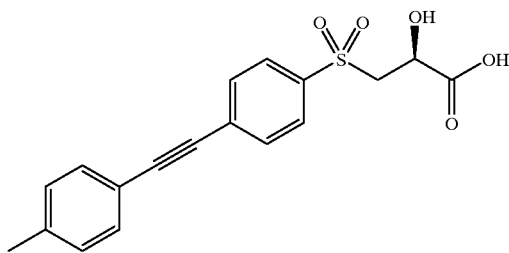

The title compound was obtained by the same procedure as Reference example 5→Example 21→Example 7→Example 8, using the R-oxiranecarboxylic acid potassium salt instead of S-oxiranecarboxylic acid potassium salt in Reference example 5.

TLC: Rf 0.25 (chloroform:methanol:acetic acid=8:1:1),

NMR (DMSO-d$_6$): δ 13.21–12.23 (1H, br.), 7.92 (2H, d, J=8.5 Hz), 7.76 (2H, d, J=8.5 Hz), 7.50 (2H, d, J=8.2 Hz), 7.27 (2H, d, J=8.2 Hz), 4.41–4.35 (1H, m), 3.75–3.56 (2H, m), 2.36 (3H, s).

Example 24

3-[4-(4-tolylethynyl)phenylsulfonyl] butyric acid

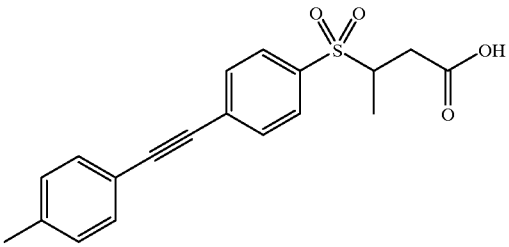

The title compound was obtained by the same procedure as a series of reactions of Example 1→Example 5→Example 7→Example 8, using 2-butenoic acid t-butyl ester and 4-bromothiophenol instead of 2-propenoic acid t-butyl ester and 4-aminothiophenol, respectively, in Example 1

TLC: Rf 0.47 (chloroform:methanol:water=4:1:0.1),

NMR (DMSO-d$_6$) δ 7.92 (2H, d, J=8.6 Hz), 7.81 (2H, d, J=7.8 Hz), 7.52 (2H, d, J=8.6 Hz), 7.29 (2H, d, J=7.8 Hz), 3.71–3.60 (1H, m), 2.76 (1H, dd, J=16.3 Hz, 4.7 Hz), 2.43–2.30 (4H, m), 1.24 (3H, d, J=7.0 Hz).

Example 25

3-[4-(4-tolylcarbonylmethyl)phenylsulfonyl]propionic acid

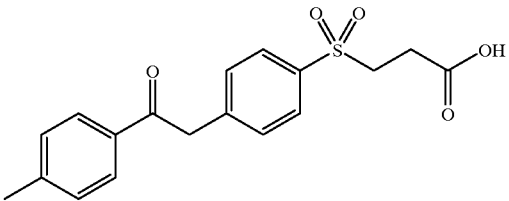

The title compound was obtained by the same procedure as a series of reactions of Example 7→Example 8, using the compound prepared in Example 6.

TLC: Rf 0.46 (ethyl acetate:acetic acid=99:1),

NMR (DMSO-d$_6$): δ 7.96 (2H, d, J=8.2 Hz), 7.84 (2H, d, J=8.2 Hz), 7.54 (2H, d, J=8.2 Hz), 7.36 (2H, d, J=8.2 Hz), 4.54 (2H, s), 3.51 (2H, t, J=7.4 Hz), 2.60–2.45 (2H), 2.39 (3H,s).

Example 26

3-[4-(4-tolylvinyl)phenylsulfonyl]propionic acid

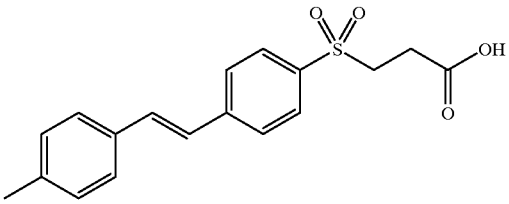

(1) intermediate:
the preparation of 3-[4-[2-hydroxy-2-(4-tolyl)ethyl]phenyl]sulfonylpropionic acid To a solution of the compound prepared in Example 25 (347 mg) in ethanol (20 ml), sodium borohydride (111 mg) was added and the reaction solution was stirred for 1 hour at room temperature. The reaction mixture was concentrated, neutralized by adding 1 N hydrochloric acid and extracted with ethyl acetate. The extract was washed with a saturated aqueous solution of sodium chloride, dried over anhydrous magnesium sulfate, concentrated and washed with ether to give the above intermediate (273 mg) having the following physical data.

TLC: Rf 0.33 (chloroform:methanol:acetic acid=90:10:1),

NMR (CD$_3$OD): δ 7.76 (2H, d, J=8.4 Hz), 7.39 (2H, d, J=8.4 Hz), 7.16 (2H, d, J=8.2 Hz), 7.10 (2H, d, J=8.2 Hz), 4.94–4.78 (1H), 3.45 (2H, t, J=7.0 Hz), 3.20–2.98 (2H,m), 2.61 (2H, t, J=7.0 Hz), 2.29 (3H, s).

(2) title compound:
the preparation of 3-[4-(4-tolylvinyl)phenylsulfonyl]propionic acid To a solution of the above intermediate (273 mg) in toluene (10 ml), p-toluenesulfonic acid 1 hydrate (30 mg) was added and the reaction solution was stirred for 2 hours at 50° C., 2 hours at 70° C., and further 4 hours at 90° C. The reaction mixture was filtered after the temperature of the reaction mixture was cooled to room temperature to give the title compound (221 mg) having the following physical data.

TLC: Rf 0.25 (chloroform:methanol=85:15),

NMR (CDCl$_3$+CD$_3$OD): δ 7.87 (2H, d, J=8.4 Hz), 7.67 (2H, d, J=8.4 Hz), 7.45 (2H, d, J=8.0 Hz), 7.25 (1H, d, J=1 6.2 Hz), 7.20 (2H, d, J=8.2 Hz), 7.08 (1H, d, J=16.2 Hz), 3.44 (2H, t, J=7.2 Hz), 2.73 (2H, t, J=7.2 Hz), 2.38 (3H, s).

Example 27~27(2)

The title compound was obtained by the same procedure as a series of reactions of Example 7→Example 8, using the compound prepared in Reference example 2.

Example 27
2-methyl-3-[4-(1-heptynyl)phenylsulfonyl]propionic acid

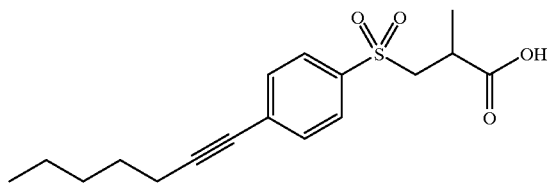

TLC: Rf 0.33 (chloroform:methanol=9:1),

NMR (DMSO-d$_6$): δ 12.53 (1H, br s), 7.82 (2H, d, J=8.4 Hz), 7.61 (2H, d, J=8.4 Hz), 3.61 (1H, dd, J=7.4 Hz, J=14.6 Hz), 3.39 (1H, dd, J=5.3 Hz, J=14.6 Hz), 2.70–2.56 (1H, m), 2.45 (2H, t, J=7.2 Hz), 1.64–1.22 (6H, m), 1.14 (3H, d, J=7.4 Hz), 0.87 (3H, t, J=6.8 Hz).

Example 27(1)
2-methyl-3-[4-(2-benzofuranyl)phenylsulfonyl]propionic acid

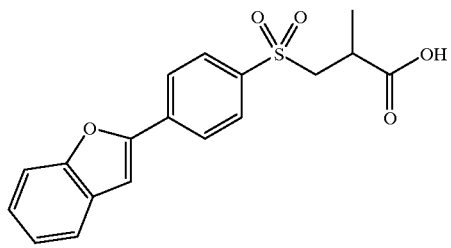

TLC: Rf 0.37 (chloroform methanol 4:1),

NMR (DMS-d$_6$): δ 12.57 (1H, br s), 8.17 (2H, d, J=8.2 Hz), 7.99 (2H, d, J=8.2 Hz), 7.74–7.65 (3H, m), 7.43–7.26 (2H, m), 3.67 (1H, dd, J=7.0 Hz, J=14.7 Hz), 3.45 (1H, dd, J=5.3 Hz, J=14.7 Hz), 2.80–2.63 (1H, m), 1.17 (3H, d, J=7.0 Hz).

Example 27(2)
2-methyl-3-[4-(4-hydroxy-but-1-ynyl)phenylsulfonyl]propionic acid

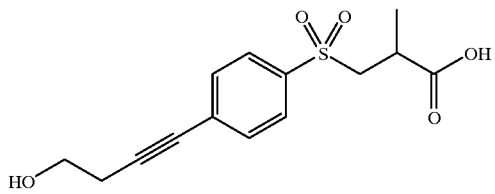

TLC: Rf 0.36 (chloroform:methanol:acetic acid=9:1:0.5),

NMR (DMSO-d$_6$): δ 7.83 (2H, d, J=8.4 Hz), 7.62 (2H, d, J=8.4 Hz), 4.07 (1H, br s), 3.66 (1H, dd, J=7.2 Hz, J=1 4.9 Hz), 3.58 (2H, t, J=6.7 Hz), 3.34–3.25 (2H, m), 2.58 (2H, t, J=6.7 Hz), 1.12 (3H, d, J=7.2 Hz).

Example 28~28(3)

The following compounds were obtained by the same procedure as a series of reactions of Example 9→Example 11, using the compounds prepared in Example 27~27(2), 8(5).

Example 28
N-hydroxy-2-methyl-3-[4-(1-heptynyl)phenylsulfonyl]propionamide

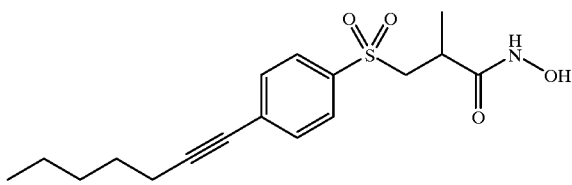

TLC: Rf 0.34 (chloroform:methanol=9:1),

NMR (DMSO-d$_6$): δ 10.54 (1H, br s), 7.82 (2H, d, J=8.6 Hz), 760 (2H, d, J=8.6 Hz), 3.55 (1H, dd, J=7.3 Hz, J=14.3 Hz), 3.28 (1H, dd, J=5.1 Hz, J=14.3 Hz), 2.64–2.39 (3H, m), 1.63–1.21 (6H, m), 1.06 (3H, d, J=7.3 Hz), 0.87 (3H, t, J=7.1 Hz).

Example 28(1)
N-hydroxy-2-methyl-3-[4-(2-benzoluranyl)phenylsulfonyl]propionamide

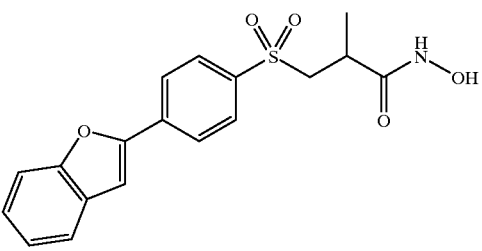

TLC: Rf 0.22 (chloroform:methanol=9:1),

NMR (DMSO-d$_6$): δ 10.57 (1H, br s), 8.80 (1H, br s), 8.16 (2H, d, J=8.6 Hz), 7.98 (2H, d, J=8.6 Hz), 7.74–7.65 (3H, m), 7.43–7.26 (2H, m), 3.61 (1H, dd, J=7.3 Hz, J=14.3 Hz), 3.32 (1H, dd, J=5.2 Hz, J=14.3 Hz), 2.59 (1H, m), 1.09 (3H, d, J=7.3 Hz).

Example 28(2)
N-hydroxy-2-methyl-3-[4-(4-hydroxy-but-1-ynyl)phenylsulfonyl]propionamide

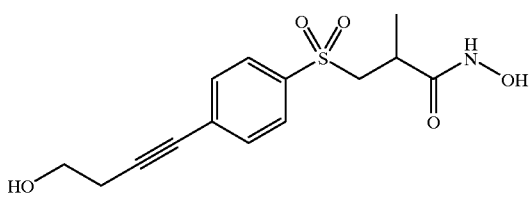

TLC: Rf 0.20 (chloroform:methanol acetic acid 9:1:0.5),

NMR (DMSO-d.): δ 10.54 (1H, br s), 8.79 (1H, s), 7.82 (2H, d, J=8.3 Hz), 7.61 (2H, d, J=8.3 Hz), 3.66–3.48 (3H, m), 3.38–3.20 (1H, m), 2.61–2.50 (3H, m), 1.05 (3H, d, J=7.0 Hz).

Example 28(3)
N-hydroxy-2-methyl-3-[4-(4-tolylethynyl)phenylsulfonyl]propionamide

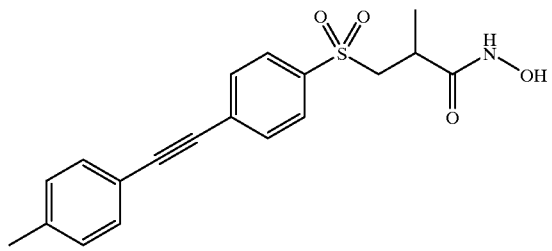

TLC: Rf 0.29 (chloroform:methanol=9:1),

NMR (DMSO-d$_6$) δ 10.56 (1H, br s), 7.89 (2H, d, J=8.8 Hz), 7.76 (2H, d, J=8.8 Hz), 7.48 (2H, d, J=8.0 Hz), 7.25 (2H, d, J=8.0 Hz), 3.59 (1H, dd, J=7.1 Hz, J=14.4 Hz), 3.32 (1H, dd, J=5.0 Hz, J=4.4 Hz), 2.67–2.54 (1H, m), 2.33 (3H, s), 1.07 (3H, d, J=7.1 Hz).

Example 29
3-[4-(phenylethynyl)phenylsulfinyl]propionic acid

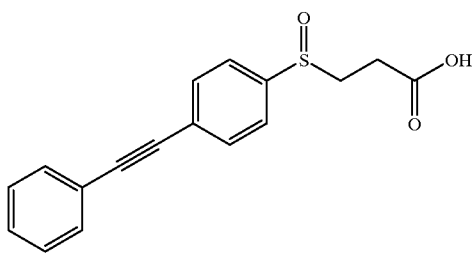

3-[4-(phenylethynyl)phenylsulfinyl]propionic acid t-butyl ester (t-butyl ester of the title compound) was obtained by the same procedure as a series of reactions of Reference example 1→Example 4→Example 7, using the compound prepared in Example 1(1). The title compound having the following physical data was obtained by the same procedure as Example 8, using t-butyl ester.

TLC: Rf 0.37 (chloroform:methanol water=4:1:0.1),

NMR (DMSO-d$_6$) δ 7.79–7.72 (4H, m), 7.63–7.58 (2H, m), 7.48–7.44 (3H, m), 3.37–3.23 (1H, m), 3.07–2.93 (1H, m), 2.69–2.50 (1H, m), 2.42–2.27 (1H, m).

Example 30
3-[4-(phenylethynyl)phenylthio]propionic acid

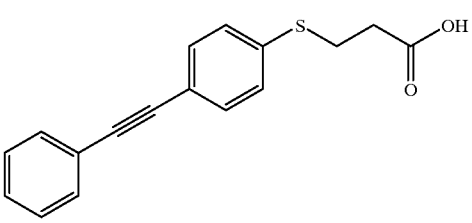

To a solution of the t-butyl ester prepared in the course of Example 29 (46 mg) in THF (2 ml), Lawesson's Reagent (55 mg) was added at 0° C. and the reaction solution was stirred for 15 minutes at 0° C. The oil obtained by concentrating of the reaction solution, was purified by silica gel column chromatography (chloroform:methanol=97:3) to give the title compound (11 mg) having the following physical data.

TLC: Rf 0.49 (chloroform:methanol:water=4:1:0.1),

NMR (CDCl$_3$+CD$_3$OD (2 drops)): δ 7.55–7.29 (9H, m), 3.20 (2H, t, J=7.4 Hz), 2.65(2H, t, J=7.4 Hz).

Example 31
3-[4-(benzoylamino)phenylsulfonyl]-2-propenoic acid

The title compounds having the following physical data were obtained by the same procedure as a series of reactions of Example 1→Example 2→Example 4, followed by the separation procedure of E and Z by passing through a silica gel column, further followed by the same procedure as Example 8, using 2-propynoic acid t-butyl ester instead of 2-propenoic acid t-butyl ester in Example 1.

(1) sis form

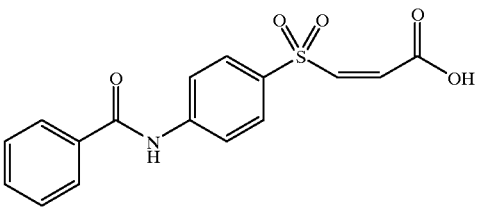

TLC: Rf 0.68 (chloroform:methanol:water=6:4:0.5),

NMR (DMSO-d$_6$): δ 10.72 (1H, s), 8.09 (2H, d, J=8.9 Hz), 8.00 (2H, d, J=7.8 Hz), 7.90 (2H, d, J=8.9 Hz), 7.62–7.56 (3H, m), 6.93 (1H, d, J=12.7 Hz), 6.83 (1H, d, J=12.7 Hz).

(2) trans form

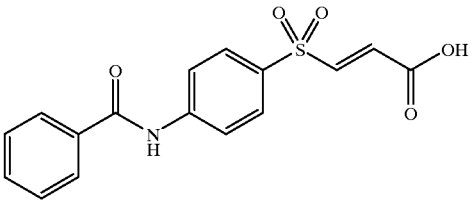

TLC: Rf 0.70 (chloroform:methanol:water=6:4:0.5),

NMR (DMSO-d$_6$): δ 10.73 (1H, s), 8.12 (2H, d, J=9.0 Hz), 8.02–7.92 (4H, m), 7.63–7.57 (3H, m), 7.66 (1H, d, J=13.8 Hz), 6.67 (1H, d, J=13.8 Hz).

Example 32
3-(4-bromophenylsulfonyl)propionic acid

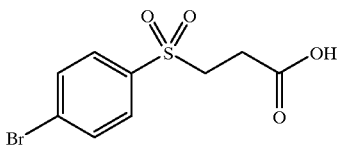

The title compound having the following physical data was obtained by the same procedure as Example 8, using the compound prepared in Example 6.

TLC: Rf 0.41 (chloroform:methanol:acetic acid= 100:10:1),

NMR (CDCl$_3$+CD$_3$OD (3 drops)): δ 7.79 (2H, d, J=9.0 Hz), 7.74 (2H, d, J=9.0 Hz), 3.44 (2H, m), 2.72 (2H, m).

[Formulation example]
Formulation example 1

The following components were admixed in conventional method and punched out to obtain 100 tablets each containing 50 mg of active ingredient.

| | |
|---|---|
| 3-[4-(phenylcarbonylamino)phenylsulfonyl]propionic acid | 5.0 g |
| Carboxymethyl Cellulose calcium (disintegrating agent) | 0.2 g |
| Magnesium stearate (lubricating agent) | 0.1 g |
| Microcrystalline cellulose | 4.7 g |

Formulation example 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| 3-[4-(phenylcarbonylamino)phenylsulfonyl]propionic acid | 2.0 g |
| mannitol | 20 g |
| distilled water | 1000 ml |

What is claimed is:

1. A method of inhibiting matrix metalloproteinase by administering in a pharmaceutically acceptable manner aryl sulfide, aryl sulfoxide, or aryl sulfone of the formula (I)

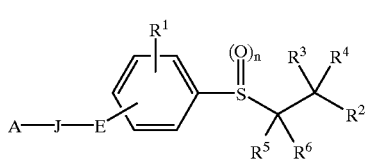

wherein $R^1$ is hydrogen, or C1-4 alkyl; , $R^2$ is —COOR$^7$ or —CONHOR$^8$;

$R^7$ is hydrogen, C1-8 alkyl, phenyl, or C1-4 alkyl substituted by phenyl, —OCOR$^{23}$ wherein R$^{23}$ is C1-4 alkyl, or —CONR$^{24}$R$^{25}$ wherein R$^{24}$ and R$^{25,}$ each independently, is hydrogen or C1-4 alkyl;

$R^8$ is hydrogen, C1-8 alkyl, phenyl, or C1-4 alkyl substituted by phenyl;

E is —CONR$^9$—, —NR$^9$CO, —OCO—, —COO—, —CH$_2$—O—, —CO—CH$_2$—, —(CH$_2$)$_2$—, —CH=CH— or —C≡C— wherein R$^9$ is hydrogen, C1-4 alkyl, phenyl, or C1-4 alkyl substituted by phenyl; with the proviso that the left side of each of the groups is attached to the J group;

J is a bond or C1-8 alkylene;

A is
1) hydrogen,
2) C1-8 alkyl,
3) Ar group which is a carbocyclic ring or heterocyclic ring optionally substituted by 1-3 of
   i) C1-15 alkyl,
   ii) C1-15 alkoxy,
   iii) halogen,
   iv) nitro,
   v) cyano,
   vi) guanidino,
   vii) amidino,
   viii) hydroxy,
   ix) benzyloxy,
   x) NR$^{12}$R$^{13}$ wherein R$^{12}$ and R$^{13}$, each independently, is hydrogen, C1-4 alkyl or —COOR$^{14}$ wherein R$^{14}$ is C1-4 alkyl or benzyloxy,
   xi) —COOR$^{15}$ wherein R$^{15}$ is hydrogen, C1-4 alkyl, phenyl, or C1-4 alkyl substituted by phenyl,
   xii) trifluoromethyl,
   xiii) carbocyclic ring,
   xiv) heterocyclic ring or
   xv) C1-4 alkyl substituted by hydroxy, C1-4 alkoxy, NR$^{12}$R$^{13}$, —COOR$^{15}$, carbocyclic ring or heterocyclic ring, or
4) C1-4 alkyl substituted by hydroxy or C1-4 alkoxy, or A, J and E taken together, represents methyl, halogen, trifluoromethyl, nitro, cyano, formyl, phenyl, hydroxy, NR$^{16}$R$^{17}$ or heterocyclic ring,
   wherein R$^{16}$ and R$^{17}$, each independently, is hydrogen, C1-4 alkyl, —COOR$^{18}$ wherein R$^{18}$ is C1-4 alkyl or benzyl,
   wherein when A, J and E taken together represents heterocyclic ring this heterocyclic ring may be optionally substituted by 1-4 of C1-4 alkyl, C1-4 alkoxy, halogen, trifluoromethyl, hydroxy, carboxyl, C1-8 alkoxycarbonyl, nitro, NR$^{24}$R$^{25}$ or CONR$^{24}$R$^{25}$;

R$^3$ and R$^4$, each independently, is
(1) hydrogen,
(2) C1-8 alkyl wherein one of the carbon atom in C1-8 alkyl may be replaced by a sulfur atom,
(3) —COOR$^{19}$ wherein R$^{19}$ is hydrogen, C1-8 alkyl, phenyl, or C1-4 alkyl substituted by phenyl,
(4) Ar$_1$ group is carbocyclic ring or heterocyclic ring optionally substituted by 1–3 of C1-4 alkyl, C1-4 alkoxy, halogen, hydroxy or trifluoromethyl,
(5) hydroxy,
(6) —N$R^{20}$R$^{21}$ wherein R$^{20}$ and R$^{21}$, each independently, is hydrogen, C1-4 alkyl, —COOR$^{22}$ or —COR$^{22}$ wherein R$^{22}$ is C1-4 alkyl or benzyl,
(7)

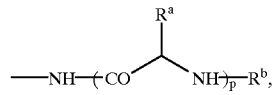

wherein R$^a$ is hydrogen or phenyl, R$^b$ is hydrogen, —COOR$^{22}$ or —COR$^{22}$, p is 1 or 2, or
(8) C1-8 alkyl substituted by substituent selected from the following (a)–(f) wherein one of the carbon atom in C1-8 alkyl may be replaced by a sulfur atom;

(a) —COOR$^{19}$,
(b) C1-4 alkoxy,
(c) hydroxy,
(d) benzyloxy,
(e) —NR$^{20}$R$^{21}$, or
(f) Ar$_1$ group, or
R$^3$ and R$^4$ taken together with the carbon to which they are attached, form C3-7 cycloalkyl; R$^5$ and R$^6$ are hydrogen or methyl, or R$^3$ and R$^5$ taken together, form a bond;

n is 0, 1 or 2;

with the proviso that:
when A, J and E taken together, form phenyl, and R$^2$ is CONHOH, then n is 1 or 2, or non-toxic salts thereof, as active ingredient.

2. Aryl sulfide, aryl sulfoxide, or aryl sulfone derivatives of the formula (I)

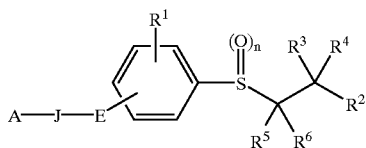

(I)

wherein

R$^1$ is hydrogen, or C1-4 alkyl;

R$^2$ is —COOR$^7$ or —CONHOR$^8$;

R$^7$ is hydrogen, C1-8 alkyl, phenyl, or C1-4 alkyl substituted by phenyl, —OCOR$^{23}$ wherein R$^{23}$ is C1-4 alkyl, or —CONR$^{24}$R$^{25}$ wherein R$^{24}$ and R$^{25}$, each independently, is hydrogen or C1-4 alkyl;

R$^8$ is hydrogen, C1-8 alkyl, phenyl, or C1-4 alkyl substituted by phenyl;

E is —CONR$^9$—, —NR$^9$CO—, —OCO—, —COO—, —CH$_2$—O—, —CO—CH$_2$—, —(CH$_2$)$_2$—, —CH=CH— or —C≡C— wherein R$^9$ is hydrogen, C1-4 alkyl, phenyl, or C1-4 alkyl substituted by phenyl, with the proviso that the left side of each of the groups is attached to the J group;

J is a bond or C1-8 alkylene;

A is
1) hydrogen,
2) C1-8 alkyl,
3) Ar group which is carbocyclic ring or heterocyclic ring optionally substituted by 1-3 of
   i) C1-15 alkyl,
   ii) C1-15 alkoxy,
   iii) halogen,
   iv) nitro,
   v) cyano,
   vi) guanidino,
   vii) amidino,
   viii) hydroxy,
   ix) benzyloxy,
   x) NR$^{12}$R$^{13}$ wherein R$^{12}$ and R$^{13}$, each independently, is hydrogen, C1-4 ayl or —COOR$^{14}$ wherein R$^{14}$ is C1-4 alkyl or benzyloxy,
   xi) —COOR$^{15}$ wherein R$^{15}$ is hydrogen, C1-4 alkyl, phenyl, or C1-4 alkyl substituted by phenyl,
   xii) trifluoromethyl,
   xiii) carbocyclic ring,
   xiv) heterocyclic ring or
   xv) C1-4 alkyl substituted by hydroxy, C1-4 alkoxy, NR$^{12}$R$^{13}$, —COOR$^{15}$ carbocyclic ring or heterocyclic ring, or
4) C1-4 alkyl substituted by hydroxy or C1-4 alkoxy, or
A, J and E taken together, represents methyl, halogen, trifluoromethyl, nitro, cyano, formyl, phenyl, hydroxy, NR$^{16}$R$^{17}$, or heterocyclic ring,
wherein R$^{16}$ and R$^{17}$, each independently, is hydrogen, C1-4 alkyl or —COOR$^{18}$ wherein R$^{18}$ is C1-4 alkyl or benzyl,
wherein when A, J and E taken together are heterocyclic ring this heterocyclic ring may be optionally substituted by 1–4 of C1-4 alkyl, C1-4 alkoxy, halogen, trifluoromethyl, hydroxy, carboxyl, C1-8 alkoxycarbonyl, nitro, NR$^{24}$R$^{25}$ or CONR$^{24}$R$^{25}$;

R$^3$ and R$^4$, each independently, is
(1) hydrogen,
(2) C1-8 alkyl with the proviso that one of the carbon atoms in C1-8 alkyl may be replaced by a sulfur atom,
(3) —COOR$^{19}$ wherein R$^{19}$ is hydrogen, C1-8 alkyl, phenyl, or C1-4 alkyl substituted by phenyl,
(4) Ar, group is carbocyclic ring or heterocyclic ring optionally substituted by 1–3 of C1-4 alkyl, C1-4 alkoxy, halogen, hydroxy or trifluoromethyl,
(5) hydroxy,
(6) —NR$^{20}$R$^{21}$ wherein R$^{20}$ and R$^{21}$, each independently, is hydrogen, C1-4 alkyl, —COOR$^{22}$ or —COR$^{22}$ wherein R$^{22}$ is C1-4 alkyl or benzyl,
(7)

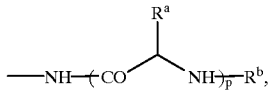

wherein R$^a$ is hydrogen or phenyl, R$^b$ is hydrogen, —COOR$^{22}$ or —COR$^{22}$, p is 1 or 2, or
(8) C1-8 alkyl substituted by substituent selected from the following (a)~(f), wherein one of the carbon atoms in C1-8 alkyl may be replaced by a sulfur atom,
(a) —COOR$^{19}$
(b) C1-4 alkoxy,
(c) hydroxy,
(d) benzyloxy,
(e) —NR$^{20}$R$^{21}$, or
(f) Ar$_1$ group,
or R$^3$ and R$^4$ taken together with the carbon to which they are attached, form C3-7 cycloalkyl;

R$^5$ and R$^6$ is hydrogen or methyl, or R$^3$ and R$^5$ taken together, form a bond;

n is 0, 1 or 2;

with the provisos that:
(a) when A, J and E taken together, form phenyl, and R$^2$ is CONHOH, then n is 1 or 2,
(b) when R$^2$ is —COOR$^7$, R$^7$ is hydrogen, C1-8 alkyl, phenyl or C1-4 alkyl substituted by phenyl, then A, J and E taken together, do not represent methyl, halogen, trifluoromethyl, nitro, cyano, hydroxy, NR$^{16}$R$^{17}$ wherein R$^{16}$ and R$^{17}$, each independently, is hydrogen,
(c) when R$^2$ is —COOR$^7$, R$^7$ is hydrogen, C1-8 alkyl, phenyl or C1-4 alkyl substituted by phenyl, A is hydrogen or C1-8 alkyl, J is a bond or C1-8 alkyl, then E does not represent —CH$_2$—O— or —(CH$_2$)$_2$—,

199

(d) the following (l)-(16) compounds are excluded:
(1) 3-(4-acetylaminophenylsulfonyl)propionic acid methyl ester,
(2) 3-(4-acetylaminophenylsulfonyl)propionic acid ethyl ester,
(3) 3-(4-vinylphenylsulfonyl)propionic acid sodium salt,
(4) 3-(4-carboxyphenylsulfonyl)propionic acid,
(5) 3-(4-formylphenylsulfonyl)propionic acid ethyl ester,
(6) 3-(4biphenylsulfonyl)propionic acid methyl ester,
(7) 4-(2-carboxy-2-methylpropylmercapto)phenyl 2-phenylbutylate,
(8) 4-(2-carboxy-2-methylpropylsulfinyl)phenyl 2-phenylbutylate,
(9) 4-(2-carboxy-2-methylpropylsulfonyl)phenyl 2-phenylbutylate,
(10) 4-(2-carboxy-2-methylpropylmercapto)phenyl 2-(4-methoxyphenyl)isobutylate,
(11) 4-(2-carboxy-2methylpropylmercapto)phenyl 2-(3,4-diethylphenyl)isobutylate,
(12) 4-(2-carboxy-2-methylpropylmercapto)phenyl 2-(1,2,3,4-tetrahydro-6-naphthyl)butyrate,
(13) 4-(2-carboxy-2-methylpropylmercapto)phenyl 2-(1-methyl-2-pyrrole)butyrate,
(14) 4-(2-carboxy-2-methylpropylsulfinyl)phenyl 2-(1-methyl-2-pyrrole)butyrate,
(15) N-t-butoxy-3-(4-bromophenylthio)propionamide,
(16) N-t-butoxy-3-(4biphenylthio)propionamide), or non-toxic salts thereof.

3. A compound according to claim 2, in which $R^2$ is —$COOR^7$.

4. A compound according to claim 2, in which $R^2$ is —$CONHOR^8$.

5. A compound according to claim 3 or claim 4, in which A is hydrogen, C1-8 alkyl, C1-4 alkyl substituted by hydroxy, or A, J and E taken together, represents methyl, halogen, trifluoromethyl, nitro, cyano, formyl, hydroxy, $NR^{16}R^{17}$.

6. A compound according to claim 3 or claim 4, in which A is carbocyclic ring optionally substituted by substituents, or A, J and E taken together, represents phenyl.

7. A compound according to claim 3 or claim 4, in which A is heterocyclic ring optionally substituted by substituents, or A, J and E taken together, represents heterocyclic ring.

8. A compound according to claim 5, which is
(1)
(1)2-benzyl-3-(4-bromophenylthio)propionic acid t-butyl ester,
(2) 2-benzyl-3-(4-bromophenylsulfonyl)propionic acid t-butyl ester,
(3) 3-[4-(1-heptynyl)phenylsulfonyl]propionic acid t-butyl ester,
(4) 3-[4-(1-heptynyl)phenylsulfonyl]propionic acid,
(5) N-t-butoxy-3-(4methoxyphenylthio)propionamide,
(6) N-benzyloxy-3-(4-methoxyphenylthio)propionamide,
(7) N-benzyloxy-3-(4-methoxyphenylsulfonyl)propionamide,
(8) N-hydroxy-3-(4-methoxyphenylthio)propionamide,
(9) N-hydroxy-3-(4-methoxyphenylsulfinyl)propionamide,
(10) N-hydroxy-3-(4-methoxyphenylsulfonyl)propionamide,

200

(11) 2-t-butoxycarbonylamino-3-(4methoxyphenylthio)propionic acid benzyl ester,
(12) 2-t butoxycarbonylamino-(4methoxyphenylsulfonyl)propionic acid benzyl ester,
(13) 2-t-butoxycarbonylamino-3-(4-methoxyphenylsulfonyl)propionic acid,
(14) 2-amino-3(4methoxyphenylsulfonyl)propionic acid benzyl ester hydrochloride,
(15) 2[N-[N-(t-butoxycarbonyl)phenylglycyl]amino]-3-(4-methoxyphenylsulfonyl)propionic acid benzyl ester,
(16) 2-acetylamino-3-(4-methoxyphenylsulfonyl)propionic acid benzyl ester,
(17) (2-[N-[N-(t-butoxycarbonyl)glycyl]amino]-3-(4-methoxyphenylsulfonyl)propionic acid benzyl ester,
(18) 2-[N-[N-(t-butoxycarbonyl)phenylglycyl]amino]-3-(4-methoxyphenylsulfonyl)propionic acid,
(19) 2-acetylamino-3-(4-methoxyphenylsulfonyl)propionic acid,
(20) 2-[N-[N-(t-butoxycarbonyl)glycyl[amino]-3-(4-methoxyphenylsulfonyl)propionic acid,
(21) 2-[N-[N-(t-butoxycarbonyl)phenylglycyl-glycyl]amino]-3-(4-methoxyphenylsulfonyl)propionic acid,
(22) 2-[N-(N-acetylglycyl)amino]-3-4-methoxyphenylsulfonyl)propionic acid,
(23) 2-[N-[N-(benzylcarbonyl)glycyl]amino]-3-(4-methoxyphenylsulfonyl)propionic acid,
(24) N-hydroxy-2-t-butoxycarbonylamino-3-(4-methoxyphenylsulfonyl)propionamide,
(25) N-hydroxy-2-[N-[N-(t-butoxycarbonyl)phenylglycyl]amino]-3-(4-methoxyphenylsulfonyl)propionamide,
(26) N-hydroxy-2-acetylamino-3-(4-methoxyphenylsulfonyl)propionamide,
(28) N-hydroxy-2-[N-[N-(t-butoxycarbonyl)glycyl]amino]-3-(4-methoxyphenylsulfonyl)propionamide,
(28) N-hydroxy-2-[N-N-(t-butoxycarbonyl)phenylglycyl-glycyl]amino]-3-(4-methoxyphenylsulfonyl)propionamide,
(29) N-hydroxy-2-[N-(N-acetylglycyl)amino]-3-(4-methoxyphenylsulfonyl)propionamide,
(30) N-hydroxy-2-[N-[N-(benzylcarbonyl)glycyl]amino]-3-(4-methoxyphenylsulfonyl)propionamide,
(31) 2-amino-3-(4-methoxyphenylsulfonyl)propionic acid trifluoroacetic acid salt,
(32) N-hydroxy-2-amino-3-(4-methoxyphenylsulfonyl)propionamide hydrochloride,
(33) 2-[N(phenylglycyl)amino]-3-4methoxyphenylsulfonyl)propionic acid trifluoroacetic acid salt,
(34) N-hydroxy-2-[N-(phenylglycyl)amino]-3-(4-methoxyphenylsulfonyl)propionamide trifluoroacetic acid salt, or
(35) N-hydroxy-2-[N-(phenylglycyl-glycyl)amino]-3-(4-methoxyphenylsulfonyl)propionamide trifluoroacetic acid salt.

9. A compound according to claim 6, which is
(1) 7(3) 3-[4-(2-pyridylethynyl)phenylsulfonyl]propionic acid t-butyl ester,
(2) 3-[4-(2-pyridylethynyl)phenylsulfonyl]propionic acid,
(3) 2-methyl-3-[4-(2-benzofuranyl)phenylsulfonyl] propionic acid, or (4) N-hydroxy-2-methyl-3-[4-(2-benzofuranyl) phenylsulfonyl]propionamide.

10. A compound according to claim 7, which is
(1) 3-[4-(benzoylamino)phenylthio]propionic acid t-butyl ester,
(2) 3-(4-benzyloxyphenylthio)propionic acid 1-butyl ester,
(3) 3-[4-(benzoylamino)phenylsulfinyl]propionic acid t-butyl ester,
(4) 3-[4-(benzoylamino)phenylsulfonyl]propionic acid t-butyl ester,
(5) 3-[4-(benzyloxy)phenylsulfonyl]propionic acid t-butyl ester,
(6) 2-methyl-3-[4-(4-tolylethynyl)phenylsulfonyl] propionic acid t-butyl ester,
(7) 3-[4-(phenylethynyl)phenylsulfonyl]propionic acid t-butyl ester,
(8) 3-[4-(4- methoxyphenylethynyl)phenylsulfonyl] propionic acid t-butyl ester,
(9) 3-[4-(4-tolylethynyl)phenylsulionyl]propionic acid t-butyl ester,
(10) 3-[4-(benzoylamino)phenylthio]propionic acid,
(11) 3-[4-(benzoylamino)phenylsulfinyl]propionic acid,
(12) 3-[4-(benzoylamino)phenylsulfonyl]propionic acid,
(13) 3-[4-(benzyloxy)phenylsulfonyl]propionic acid,
(14) 2-methyl-3-[4-(4-tolylcarbonyl methyl) phenylsulfonyl]propionic acid,
(15) 2-methyl-3-[4-(4-tolylethynyl)phenylsulfonyl] propionic acid,
(16) 3-[4-(phenylethynyl)phenylsulfonyl]propionic acid,
(17) 3-[4-(4-methoxyphenylethynyl)phenylsulfonyl] propionic acid,
(18) 2-benzyl-3-[4-(4-tolylethynyl)phenylsulfonyl] propionic acid,
(19) 2R-hydroxy-3-(4-bromophenylsulfonyl)propionic acid t-butyl ester,
(20) 2R-hydroxy-3-[4-(4-tolylethynyl)phenyisulfonyl] propionic acid,
(21) 2S-hydroxy-3-[4-(4-tolylethynyl)phenylsulfonyl] propionic acid,
(22) 3-[4-(4-tolylethynyl)phenylsulfonyl]butyric acid,
(23) 3-[4-(4-tolylcarbonylmethyl)phenylsulfonyl] propionic acid,
(24) 3-[4-(4-tolylvinyl)phenylsulfonyl]propionic acid,
(25) 2-methyl-3-[4-(1-heptynyl)phenylsulfonyl]propionic acid,
(26) 2-methyl-3-[4-(4-hydroxy-but-1-ynyl) phenylsulfonyl]propionic acid,
(27) N-hydroxy-2-methyl-3-[4-(1-heptynyl) phenylsulfonyl]propionamide,
(28) N-hydroxy-2-methyl-3-[4-(4-hydroxy-but-1-ynyl) phenylsulfonyl]propionamide,
(29) N-hydroxy-2-methyl-3-[4-(4-tolylethynyl) phenylsuffonyl]propionamide,
(30) 3-[4-(phenylethynyl)phenylsulfinyl]propionic acid,
(31) 3-[4-(phenylethynyl)phenylthio]propionic acid,
(32) cis-3-[4-(benzoylamino)phenylsulfonyl]-2-propenoic acid, or
(33) trans-3-[4-(benzoylamino)phenylsulfonyl]-2-propenoic acid.

\* \* \* \* \*